United States Patent
Hovatta et al.

(10) Patent No.: US 10,889,801 B2
(45) Date of Patent: Jan. 12, 2021

(54) METHODS OF PRODUCING RPE CELLS

(71) Applicant: BioLamina AB, Sundbyberg (SE)

(72) Inventors: Outi Hovatta, Esbo (FI); Karl Tryggvason, Singapore (SG)

(73) Assignee: BioLamina AB, Sundyberg (SE)

( * ) Notice: Subject to any disclaimer, the term of this patent is extended or adjusted under 35 U.S.C. 154(b) by 0 days.

(21) Appl. No.: 14/646,059

(22) PCT Filed: Dec. 3, 2013

(86) PCT No.: PCT/IB2013/003160
§ 371 (c)(1),
(2) Date: May 20, 2015

(87) PCT Pub. No.: WO2014/087244
PCT Pub. Date: Jun. 12, 2014

(65) Prior Publication Data
US 2015/0299653 A1    Oct. 22, 2015

Related U.S. Application Data

(60) Provisional application No. 61/733,314, filed on Dec. 4, 2012, provisional application No. 61/732,764, filed on Dec. 3, 2012.

(51) Int. Cl.
| | |
|---|---|
| *C12N 5/079* | (2010.01) |
| *C12N 5/00* | (2006.01) |
| *A61K 9/00* | (2006.01) |
| *A61K 35/30* | (2015.01) |

(52) U.S. Cl.
CPC .......... *C12N 5/0621* (2013.01); *A61K 9/0019* (2013.01); *A61K 9/0048* (2013.01); *A61K 35/30* (2013.01); *C12N 5/0056* (2013.01); *C12N 2500/92* (2013.01); *C12N 2500/98* (2013.01); *C12N 2501/115* (2013.01); *C12N 2506/02* (2013.01); *C12N 2533/50* (2013.01); *C12N 2533/52* (2013.01)

(58) Field of Classification Search
CPC .. A61K 35/30; C12N 5/0056; C12N 2533/52; C12N 2500/98
See application file for complete search history.

(56) References Cited

U.S. PATENT DOCUMENTS

| | | | |
|---|---|---|---|
| 2010/0203635 A1 | 8/2010 | Tryggvason et al. | |
| 2012/0156782 A1* | 6/2012 | Tryggvason | ........... C07K 14/78 435/402 |
| 2013/0196369 A1 | 8/2013 | Nikita et al. | |

OTHER PUBLICATIONS

International Search Report and Written Opinion dated Jun. 17, 2014 for PCT Application No. PCT/IB2013/003160.
Klimanskaya; Retinal Pigment Epithelium; Methods of Enzymology, vol. 418; pp. 169-194; 2006.
Krohne et al.; Generation of Retinal Pigment Epithelial Cells from Small Molecules and OCT4 Reprogrammed Human Induced Pluripotent Stem Cells; Stem Cells Translation Medicine 2012:1, pp. 96-109; Feb. 6, 2012.
Rodin et al.; Long-term self-renewal of human pluripotent stem cells on human recombinant laminin-511; Nature Biotechnology, vol. 28, No. 6, pp. 611-617; Jun. 2010.
Rowland et al.; Differentiation of human pluripotent stem cells to retinal pigmented epithelium in defined conditions using purified extracellular matrix proteins; Journal of Tissue Engineering and Regenerative Medicine, pp. 642-653; Apr. 18, 2012.
Vaajasaari et al.; Toward the defined and xeno-free differentiation of functional human pluripotent stem cell-derived retinal pigment epithelial cells; Moluecular Vision 2011; 17; pp. 558-575; Feb. 22, 2011.
Zahabi et al.; A New Efficient Protocol for Directed Differentiation of Retinal Pigmented Epithelial Cells from Normal and Retinal Disease Induced Pluripotent Stem Cells; Stem Cells and Development, vol. 21, No. 12; pp. 2262-2272; 2012.
Reyes, Alvaro Plaza et al., Xeno-Free and Defined Human Embryonic Stem Cell-Derived Retinal Pigment Epithelial Cells Functionally Integrate in a Large-Eyed Preclinical Model, Stem Cell Reports, Jan. 12, 2016, pp. 9-17, vol. 6.
Reyes, Alvaro Plaza et al., Xeno-Free and Defined Human Embryonic Stem Cell-Derived Retinal Pigment Epithelial Cells Functionally Integrate in a Large-Eyed Preclinical Model, Supplemental Information, Stem Cell Reports, Jan. 12, 2016, pp. 9-17, vol. 6.

* cited by examiner

*Primary Examiner* — Blaine Lankford
(74) *Attorney, Agent, or Firm* — Fay Sharpe LLP

(57) ABSTRACT

The present disclosure relates to the use of laminin-521 in obtaining retinal pigment epithelium (RPE) cells. Pluripotent human embryonic stem cells are cultured on plates coated with recombinant laminin-521 (laminin-11), in totally defined and xeno-free conditions. A first cell culture medium contains a growth factor, and a second cell culture medium does not contain growth factor. The stem cells are first exposed to the first cell culture medium, then exposed to the second cell culture medium for a longer time period. After a number of weeks, clinical grade RPE cells are obtained from the stem cells.

17 Claims, 16 Drawing Sheets

Specification includes a Sequence Listing.

SEQUENCE LISTING

```
<160> NUMBER OF SEQ ID NOS: 8

<210> SEQ ID NO 1
<211> LENGTH: 3695
<212> TYPE: PRT
<213> ORGANISM: Homo sapiens

<400> SEQUENCE: 1

Met Ala Lys Arg Leu Cys Ala Gly Ser Ala Leu Cys Val Arg Gly Pro
1               5                   10                  15

Arg Gly Pro Ala Pro Leu Leu Leu Val Gly Leu Ala Leu Leu Gly Ala
            20                  25                  30

Ala Arg Ala Arg Glu Glu Ala Gly Gly Gly Phe Ser Leu His Pro Pro
        35                  40                  45

Tyr Phe Asn Leu Ala Glu Gly Ala Arg Ile Ala Ala Ser Ala Thr Cys
    50                  55                  60

Gly Glu Glu Ala Pro Ala Arg Gly Ser Pro Arg Pro Thr Glu Asp Leu
65                  70                  75                  80

Tyr Cys Lys Leu Val Gly Gly Pro Val Ala Gly Gly Asp Pro Asn Gln
                85                  90                  95

Thr Ile Arg Gly Gln Tyr Cys Asp Ile Cys Thr Ala Ala Asn Ser Asn
            100                 105                 110

Lys Ala His Pro Ala Ser Asn Ala Ile Asp Gly Thr Glu Arg Trp Trp
        115                 120                 125
```

-continued

```
Gln Ser Pro Pro Leu Ser Arg Gly Leu Glu Tyr Asn Glu Val Asn Val
    130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
                165                 170                 175

Asp Phe Gly Arg Thr Tyr Gln Pro Trp Gln Phe Phe Ala Ser Ser Lys
            180                 185                 190

Arg Asp Cys Leu Glu Arg Phe Gly Pro Gln Thr Leu Glu Arg Ile Thr
        195                 200                 205

Arg Asp Asp Ala Ala Ile Cys Thr Thr Glu Tyr Ser Arg Ile Val Pro
210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
            260                 265                 270

Leu Met Gly Lys Ala Leu Arg Asp Pro Thr Val Thr Arg Arg Tyr Tyr
        275                 280                 285

Tyr Ser Ile Lys Asp Ile Ser Ile Gly Gly Arg Cys Val Cys His Gly
290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Gly Thr Cys Asp Arg Cys
                325                 330                 335

Cys Pro Gly Phe Asn Gln Gln Pro Trp Lys Pro Ala Thr Ala Asn Ser
            340                 345                 350

Ala Asn Glu Cys Gln Ser Cys Asn Cys Tyr Gly His Ala Thr Asp Cys
        355                 360                 365

Tyr Tyr Asp Pro Glu Val Asp Arg Arg Ala Ser Gln Ser Leu Asp
370                 375                 380

Gly Thr Tyr Gln Gly Gly Gly Val Cys Ile Asp Cys Gln His His Thr
385                 390                 395                 400

Thr Gly Val Asn Cys Glu Arg Cys Leu Pro Gly Phe Tyr Arg Ser Pro
                405                 410                 415

Asn His Pro Leu Asp Ser Pro His Val Cys Arg Arg Cys Asn Cys Glu
            420                 425                 430

Ser Asp Phe Thr Asp Gly Thr Cys Glu Asp Leu Thr Gly Arg Cys Tyr
        435                 440                 445

Cys Arg Pro Asn Phe Ser Gly Glu Arg Cys Asp Val Cys Ala Glu Gly
        450                 455                 460

Phe Thr Gly Phe Pro Ser Cys Tyr Pro Thr Pro Ser Ser Asn Asp
465                 470                 475                 480

Thr Arg Glu Gln Val Leu Pro Ala Gly Gln Ile Val Asn Cys Asp Cys
                485                 490                 495

Ser Ala Ala Gly Thr Gln Gly Asn Ala Cys Arg Lys Asp Pro Arg Val
            500                 505                 510

Gly Arg Cys Leu Cys Lys Pro Asn Phe Gln Gly Thr His Cys Glu Leu
        515                 520                 525

Cys Ala Pro Gly Phe Tyr Gly Pro Gly Cys Gln Pro Cys Gln Cys Ser
        530                 535                 540

Ser Pro Gly Val Ala Asp Asp Arg Cys Asp Pro Asp Thr Gly Gln Cys
```

```
         545                 550                 555                 560
Arg Cys Arg Val Gly Phe Glu Gly Ala Thr Cys Asp Arg Cys Ala Pro
                565                 570                 575
Gly Tyr Phe His Phe Pro Leu Cys Gln Leu Cys Gly Cys Ser Pro Ala
                580                 585                 590
Gly Thr Leu Pro Glu Gly Cys Asp Glu Ala Gly Arg Cys Leu Cys Gln
                595                 600                 605
Pro Glu Phe Ala Gly Pro His Cys Asp Arg Cys Arg Pro Gly Tyr His
                610                 615                 620
Gly Phe Pro Asn Cys Gln Ala Cys Thr Cys Asp Pro Arg Gly Ala Leu
625                 630                 635                 640
Asp Gln Leu Cys Gly Ala Gly Gly Leu Cys Arg Cys Arg Pro Gly Tyr
                645                 650                 655
Thr Gly Thr Ala Cys Gln Glu Cys Ser Pro Gly Phe His Gly Phe Pro
                660                 665                 670
Ser Cys Val Pro Cys His Cys Ser Ala Glu Gly Ser Leu His Ala Ala
                675                 680                 685
Cys Asp Pro Arg Ser Gly Gln Cys Ser Cys Arg Pro Arg Val Thr Gly
                690                 695                 700
Leu Arg Cys Asp Thr Cys Val Pro Gly Ala Tyr Asn Phe Pro Tyr Cys
705                 710                 715                 720
Glu Ala Gly Ser Cys His Pro Ala Gly Leu Ala Pro Val Asp Pro Ala
                725                 730                 735
Leu Pro Glu Ala Gln Val Pro Cys Met Cys Arg Ala His Val Glu Gly
                740                 745                 750
Pro Ser Cys Asp Arg Cys Lys Pro Gly Phe Trp Gly Leu Ser Pro Ser
                755                 760                 765
Asn Pro Glu Gly Cys Thr Arg Cys Ser Cys Asp Leu Arg Gly Thr Leu
                770                 775                 780
Gly Gly Val Ala Glu Cys Gln Pro Gly Thr Gly Gln Cys Phe Cys Lys
785                 790                 795                 800
Pro His Val Cys Gly Gln Ala Cys Ala Ser Cys Lys Asp Gly Phe Phe
                805                 810                 815
Gly Leu Asp Gln Ala Asp Tyr Phe Gly Cys Arg Ser Cys Arg Cys Asp
                820                 825                 830
Ile Gly Gly Ala Leu Gly Gln Ser Cys Glu Pro Arg Thr Gly Val Cys
                835                 840                 845
Arg Cys Arg Pro Asn Thr Gln Gly Pro Thr Cys Ser Glu Pro Ala Arg
850                 855                 860
Asp His Tyr Leu Pro Asp Leu His His Leu Arg Leu Glu Leu Glu Glu
865                 870                 875                 880
Ala Ala Thr Pro Glu Gly His Ala Val Arg Phe Gly Phe Asn Pro Leu
                885                 890                 895
Glu Phe Glu Asn Phe Ser Trp Arg Gly Tyr Ala Gln Met Ala Pro Val
                900                 905                 910
Gln Pro Arg Ile Val Ala Arg Leu Asn Leu Thr Ser Pro Asp Leu Phe
                915                 920                 925
Trp Leu Val Phe Arg Tyr Val Asn Arg Gly Ala Met Ser Val Ser Gly
                930                 935                 940
Arg Val Ser Val Arg Glu Glu Gly Arg Ser Ala Thr Cys Ala Asn Cys
945                 950                 955                 960
Thr Ala Gln Ser Gln Pro Val Ala Phe Pro Pro Ser Thr Glu Pro Ala
                965                 970                 975
```

```
Phe Ile Thr Val Pro Gln Arg Gly Phe Gly Glu Pro Phe Val Leu Asn
                980                 985                 990

Pro Gly Thr Trp Ala Leu Arg Val  Glu Ala Glu Gly Val  Leu Leu Asp
                995                 1000                1005

Tyr Val Val Leu Leu Pro Ser  Ala Tyr Tyr Glu Ala  Ala Leu Leu
        1010                1015                1020

Gln Leu Arg Val Thr Glu Ala  Cys Thr Tyr Arg Pro  Ser Ala Gln
        1025                1030                1035

Gln Ser Gly Asp Asn Cys Leu  Leu Tyr Thr His Leu  Pro Leu Asp
        1040                1045                1050

Gly Phe Pro Ser Ala Ala Gly  Leu Glu Ala Leu Cys  Arg Gln Asp
        1055                1060                1065

Asn Ser Leu Pro Arg Pro Cys  Pro Thr Glu Gln Leu  Ser Pro Ser
        1070                1075                1080

His Pro Pro Leu Ile Thr Cys  Thr Gly Ser Asp Val  Asp Val Gln
        1085                1090                1095

Leu Gln Val Ala Val Pro Gln  Pro Gly Arg Tyr Ala  Leu Val Val
        1100                1105                1110

Glu Tyr Ala Asn Glu Asp Ala  Arg Gln Glu Val Gly  Val Ala Val
        1115                1120                1125

His Thr Pro Gln Arg Ala Pro  Gln Gln Gly Leu Leu  Ser Leu His
        1130                1135                1140

Pro Cys Leu Tyr Ser Thr Leu  Cys Arg Gly Thr Ala  Arg Asp Thr
        1145                1150                1155

Gln Asp His Leu Ala Val Phe  His Leu Asp Ser Glu  Ala Ser Val
        1160                1165                1170

Arg Leu Thr Ala Glu Gln Ala  Arg Phe Phe Leu His  Gly Val Thr
        1175                1180                1185

Leu Val Pro Ile Glu Glu Phe  Ser Pro Glu Phe Val  Glu Pro Arg
        1190                1195                1200

Val Ser Cys Ile Ser Ser His  Gly Ala Phe Gly Pro  Asn Ser Ala
        1205                1210                1215

Ala Cys Leu Pro Ser Arg Phe  Pro Lys Pro Pro Gln  Pro Ile Ile
        1220                1225                1230

Leu Arg Asp Cys Gln Val Ile  Pro Leu Pro Pro Gly  Leu Pro Leu
        1235                1240                1245

Thr His Ala Gln Asp Leu Thr  Pro Ala Met Ser Pro  Ala Gly Pro
        1250                1255                1260

Arg Pro Arg Pro Pro Thr Ala  Val Asp Pro Asp Ala  Glu Pro Thr
        1265                1270                1275

Leu Leu Arg Glu Pro Gln Ala  Thr Val Val Phe Thr  Thr His Val
        1280                1285                1290

Pro Thr Leu Gly Arg Tyr Ala  Phe Leu Leu His Gly  Tyr Gln Pro
        1295                1300                1305

Ala His Pro Thr Phe Pro Val  Glu Val Leu Ile Asn  Ala Gly Arg
        1310                1315                1320

Val Trp Gln Gly His Ala Asn  Ala Ser Phe Cys Pro  His Gly Tyr
        1325                1330                1335

Gly Cys Arg Thr Leu Val Val  Cys Glu Gly Gln Ala  Leu Leu Asp
        1340                1345                1350

Val Thr His Ser Glu Leu Thr  Val Thr Val Arg Val  Pro Lys Gly
        1355                1360                1365
```

-continued

Arg Trp Leu Trp Leu Asp Tyr Val Leu Val Val Pro Glu Asn Val
1370                1375                1380

Tyr Ser Phe Gly Tyr Leu Arg Glu Glu Pro Leu Asp Lys Ser Tyr
1385                1390                1395

Asp Phe Ile Ser His Cys Ala Ala Gln Gly Tyr His Ile Ser Pro
1400                1405                1410

Ser Ser Ser Ser Leu Phe Cys Arg Asn Ala Ala Ala Ser Leu Ser
1415                1420                1425

Leu Phe Tyr Asn Asn Gly Ala Arg Pro Cys Gly Cys His Glu Val
1430                1435                1440

Gly Ala Thr Gly Pro Thr Cys Glu Pro Phe Gly Gly Gln Cys Pro
1445                1450                1455

Cys His Ala His Val Ile Gly Arg Asp Cys Ser Arg Cys Ala Thr
1460                1465                1470

Gly Tyr Trp Gly Phe Pro Asn Cys Arg Pro Cys Asp Cys Gly Ala
1475                1480                1485

Arg Leu Cys Asp Glu Leu Thr Gly Gln Cys Ile Cys Pro Pro Arg
1490                1495                1500

Thr Ile Pro Pro Asp Cys Leu Leu Cys Gln Pro Gln Thr Phe Gly
1505                1510                1515

Cys His Pro Leu Val Gly Cys Glu Glu Cys Asn Cys Ser Gly Pro
1520                1525                1530

Gly Ile Gln Glu Leu Thr Asp Pro Thr Cys Asp Thr Asp Ser Gly
1535                1540                1545

Gln Cys Lys Cys Arg Pro Asn Val Thr Gly Arg Arg Cys Asp Thr
1550                1555                1560

Cys Ser Pro Gly Phe His Gly Tyr Pro Arg Cys Arg Pro Cys Asp
1565                1570                1575

Cys His Glu Ala Gly Thr Ala Pro Gly Val Cys Asp Pro Leu Thr
1580                1585                1590

Gly Gln Cys Tyr Cys Lys Glu Asn Val Gln Gly Pro Lys Cys Asp
1595                1600                1605

Gln Cys Ser Leu Gly Thr Phe Ser Leu Asp Ala Ala Asn Pro Lys
1610                1615                1620

Gly Cys Thr Arg Cys Phe Cys Phe Gly Ala Thr Glu Arg Cys Arg
1625                1630                1635

Ser Ser Ser Tyr Thr Arg Gln Glu Phe Val Asp Met Glu Gly Trp
1640                1645                1650

Val Leu Leu Ser Thr Asp Arg Gln Val Val Pro His Glu Arg Gln
1655                1660                1665

Pro Gly Thr Glu Met Leu Arg Ala Asp Leu Arg His Val Pro Glu
1670                1675                1680

Ala Val Pro Glu Ala Phe Pro Glu Leu Tyr Trp Gln Ala Pro Pro
1685                1690                1695

Ser Tyr Leu Gly Asp Arg Val Ser Ser Tyr Gly Gly Thr Leu Arg
1700                1705                1710

Tyr Glu Leu His Ser Glu Thr Gln Arg Gly Asp Val Phe Val Pro
1715                1720                1725

Met Glu Ser Arg Pro Asp Val Val Leu Gln Gly Asn Gln Met Ser
1730                1735                1740

Ile Thr Phe Leu Glu Pro Ala Tyr Pro Thr Pro Gly His Val His
1745                1750                1755

Arg Gly Gln Leu Gln Leu Val Glu Gly Asn Phe Arg His Thr Glu

-continued

```
          1760                1765                1770
Thr Arg Asn Thr Val Ser Arg Glu Glu Leu Met Met Val Leu Ala
          1775                1780                1785
Ser Leu Glu Gln Leu Gln Ile Arg Ala Leu Phe Ser Gln Ile Ser
          1790                1795                1800
Ser Ala Val Phe Leu Arg Arg Val Ala Leu Glu Val Ala Ser Pro
          1805                1810                1815
Ala Gly Gln Gly Ala Leu Ala Ser Asn Val Glu Leu Cys Leu Cys
          1820                1825                1830
Pro Ala Ser Tyr Arg Gly Asp Ser Cys Gln Glu Cys Ala Pro Gly
          1835                1840                1845
Phe Tyr Arg Asp Val Lys Gly Leu Phe Leu Gly Arg Cys Val Pro
          1850                1855                1860
Cys Gln Cys His Gly His Ser Asp Arg Cys Leu Pro Gly Ser Gly
          1865                1870                1875
Val Cys Val Asp Cys Gln His Asn Thr Glu Gly Ala His Cys Glu
          1880                1885                1890
Arg Cys Gln Ala Gly Phe Val Ser Ser Arg Asp Asp Pro Ser Ala
          1895                1900                1905
Pro Cys Val Ser Cys Pro Cys Pro Leu Ser Val Pro Ser Asn Asn
          1910                1915                1920
Phe Ala Glu Gly Cys Val Leu Arg Gly Gly Arg Thr Gln Cys Leu
          1925                1930                1935
Cys Lys Pro Gly Tyr Ala Gly Ala Ser Cys Glu Arg Cys Ala Pro
          1940                1945                1950
Gly Phe Phe Gly Asn Pro Leu Val Leu Gly Ser Ser Cys Gln Pro
          1955                1960                1965
Cys Asp Cys Ser Gly Asn Gly Asp Pro Asn Leu Leu Phe Ser Asp
          1970                1975                1980
Cys Asp Pro Leu Thr Gly Ala Cys Arg Gly Cys Leu Arg His Thr
          1985                1990                1995
Thr Gly Pro Arg Cys Glu Ile Cys Ala Pro Gly Phe Tyr Gly Asn
          2000                2005                2010
Ala Leu Leu Pro Gly Asn Cys Thr Arg Cys Asp Cys Thr Pro Cys
          2015                2020                2025
Gly Thr Glu Ala Cys Asp Pro His Ser Gly His Cys Leu Cys Lys
          2030                2035                2040
Ala Gly Val Thr Gly Arg Arg Cys Asp Arg Cys Gln Glu Gly His
          2045                2050                2055
Phe Gly Phe Asp Gly Cys Gly Gly Cys Arg Pro Cys Ala Cys Gly
          2060                2065                2070
Pro Ala Ala Glu Gly Ser Glu Cys His Pro Gln Ser Gly Gln Cys
          2075                2080                2085
His Cys Arg Pro Gly Thr Met Gly Pro Gln Cys Arg Glu Cys Ala
          2090                2095                2100
Pro Gly Tyr Trp Gly Leu Pro Glu Gln Gly Cys Arg Arg Cys Gln
          2105                2110                2115
Cys Pro Gly Gly Arg Cys Asp Pro His Thr Gly Arg Cys Asn Cys
          2120                2125                2130
Pro Pro Gly Leu Ser Gly Glu Arg Cys Asp Thr Cys Ser Gln Gln
          2135                2140                2145
His Gln Val Pro Val Pro Gly Gly Pro Val Gly His Ser Ile His
          2150                2155                2160
```

-continued

Cys Glu Val Cys Asp His Cys Val Val Leu Leu Leu Asp Asp Leu
2165              2170                    2175

Glu Arg Ala Gly Ala Leu Leu Pro Ala Ile His Glu Gln Leu Arg
2180              2185                    2190

Gly Ile Asn Ala Ser Ser Met Ala Trp Ala Arg Leu His Arg Leu
2195              2200                    2205

Asn Ala Ser Ile Ala Asp Leu Gln Ser Gln Leu Arg Ser Pro Leu
2210              2215                    2220

Gly Pro Arg His Glu Thr Ala Gln Gln Leu Glu Val Leu Glu Gln
2225              2230                    2235

Gln Ser Thr Ser Leu Gly Gln Asp Ala Arg Arg Leu Gly Gly Gln
2240              2245                    2250

Ala Val Gly Thr Arg Asp Gln Ala Ser Gln Leu Leu Ala Gly Thr
2255              2260                    2265

Glu Ala Thr Leu Gly His Ala Lys Thr Leu Leu Ala Ala Ile Arg
2270              2275                    2280

Ala Val Asp Arg Thr Leu Ser Glu Leu Met Ser Gln Thr Gly His
2285              2290                    2295

Leu Gly Leu Ala Asn Ala Ser Ala Pro Ser Gly Glu Gln Leu Leu
2300              2305                    2310

Arg Thr Leu Ala Glu Val Glu Arg Leu Leu Trp Glu Met Arg Ala
2315              2320                    2325

Arg Asp Leu Gly Ala Pro Gln Ala Ala Ala Glu Ala Glu Leu Ala
2330              2335                    2340

Ala Ala Gln Arg Leu Leu Ala Arg Val Gln Glu Gln Leu Ser Ser
2345              2350                    2355

Leu Trp Glu Glu Asn Gln Ala Leu Ala Thr Gln Thr Arg Asp Arg
2360              2365                    2370

Leu Ala Gln His Glu Ala Gly Leu Met Asp Leu Arg Glu Ala Leu
2375              2380                    2385

Asn Arg Ala Val Asp Ala Thr Arg Glu Ala Gln Glu Leu Asn Ser
2390              2395                    2400

Arg Asn Gln Glu Arg Leu Glu Glu Ala Leu Gln Arg Lys Gln Glu
2405              2410                    2415

Leu Ser Arg Asp Asn Ala Thr Leu Gln Ala Thr Leu His Ala Ala
2420              2425                    2430

Arg Asp Thr Leu Ala Ser Val Phe Arg Leu Leu His Ser Leu Asp
2435              2440                    2445

Gln Ala Lys Glu Glu Leu Glu Arg Leu Ala Ala Ser Leu Asp Gly
2450              2455                    2460

Ala Arg Thr Pro Leu Leu Gln Arg Met Gln Thr Phe Ser Pro Ala
2465              2470                    2475

Gly Ser Lys Leu Arg Leu Val Glu Ala Ala Glu Ala His Ala Gln
2480              2485                    2490

Gln Leu Gly Gln Leu Ala Leu Asn Leu Ser Ser Ile Ile Leu Asp
2495              2500                    2505

Val Asn Gln Asp Arg Leu Thr Gln Arg Ala Ile Glu Ala Ser Asn
2510              2515                    2520

Ala Tyr Ser Arg Ile Leu Gln Ala Val Gln Ala Ala Glu Asp Ala
2525              2530                    2535

Ala Gly Gln Ala Leu Gln Gln Ala Asp His Thr Trp Ala Thr Val
2540              2545                    2550

```
Val Arg Gln Gly Leu Val Asp Arg Ala Gln Gln Leu Leu Ala Asn
2555                2560                2565

Ser Thr Ala Leu Glu Glu Ala Met Leu Gln Glu Gln Gln Arg Leu
2570                2575                2580

Gly Leu Val Trp Ala Ala Leu Gln Gly Ala Arg Thr Gln Leu Arg
2585                2590                2595

Asp Val Arg Ala Lys Lys Asp Gln Leu Glu Ala His Ile Gln Ala
2600                2605                2610

Ala Gln Ala Met Leu Ala Met Asp Thr Asp Glu Thr Ser Lys Lys
2615                2620                2625

Ile Ala His Ala Lys Ala Val Ala Ala Glu Ala Gln Asp Thr Ala
2630                2635                2640

Thr Arg Val Gln Ser Gln Leu Gln Ala Met Gln Glu Asn Val Glu
2645                2650                2655

Arg Trp Gln Gly Gln Tyr Glu Gly Leu Arg Gly Gln Asp Leu Gly
2660                2665                2670

Gln Ala Val Leu Asp Ala Gly His Ser Val Ser Thr Leu Glu Lys
2675                2680                2685

Thr Leu Pro Gln Leu Leu Ala Lys Leu Ser Ile Leu Glu Asn Arg
2690                2695                2700

Gly Val His Asn Ala Ser Leu Ala Leu Ser Ala Ser Ile Gly Arg
2705                2710                2715

Val Arg Glu Leu Ile Ala Gln Ala Arg Gly Ala Ala Ser Lys Val
2720                2725                2730

Lys Val Pro Met Lys Phe Asn Gly Arg Ser Gly Val Gln Leu Arg
2735                2740                2745

Thr Pro Arg Asp Leu Ala Asp Leu Ala Ala Tyr Thr Ala Leu Lys
2750                2755                2760

Phe Tyr Leu Gln Gly Pro Glu Pro Glu Pro Gly Gln Gly Thr Glu
2765                2770                2775

Asp Arg Phe Val Met Tyr Met Gly Ser Arg Gln Ala Thr Gly Asp
2780                2785                2790

Tyr Met Gly Val Ser Leu Arg Asp Lys Lys Val His Trp Val Tyr
2795                2800                2805

Gln Leu Gly Glu Ala Gly Pro Ala Val Leu Ser Ile Asp Glu Asp
2810                2815                2820

Ile Gly Glu Gln Phe Ala Ala Val Ser Leu Asp Arg Thr Leu Gln
2825                2830                2835

Phe Gly His Met Ser Val Thr Val Glu Arg Gln Met Ile Gln Glu
2840                2845                2850

Thr Lys Gly Asp Thr Val Ala Pro Gly Ala Glu Gly Leu Leu Asn
2855                2860                2865

Leu Arg Pro Asp Asp Phe Val Phe Tyr Val Gly Gly Tyr Pro Ser
2870                2875                2880

Thr Phe Thr Pro Pro Pro Leu Leu Arg Phe Pro Gly Tyr Arg Gly
2885                2890                2895

Cys Ile Glu Met Asp Thr Leu Asn Glu Glu Val Val Ser Leu Tyr
2900                2905                2910

Asn Phe Glu Arg Thr Phe Gln Leu Asp Thr Ala Val Asp Arg Pro
2915                2920                2925

Cys Ala Arg Ser Lys Ser Thr Gly Asp Pro Trp Leu Thr Asp Gly
2930                2935                2940

Ser Tyr Leu Asp Gly Thr Gly Phe Ala Arg Ile Ser Phe Asp Ser
```

```
                2945                2950                2955
Gln Ile Ser Thr Thr Lys Arg Phe Glu Gln Glu Leu Arg Leu Val
    2960                2965                2970
Ser Tyr Ser Gly Val Leu Phe Phe Leu Lys Gln Gln Ser Gln Phe
    2975                2980                2985
Leu Cys Leu Ala Val Gln Glu Gly Ser Leu Val Leu Leu Tyr Asp
    2990                2995                3000
Phe Gly Ala Gly Leu Lys Lys Ala Val Pro Leu Gln Pro Pro Pro
    3005                3010                3015
Pro Leu Thr Ser Ala Ser Lys Ala Ile Gln Val Phe Leu Leu Gly
    3020                3025                3030
Gly Ser Arg Lys Arg Val Leu Val Arg Val Glu Arg Ala Thr Val
    3035                3040                3045
Tyr Ser Val Glu Gln Asp Asn Asp Leu Glu Leu Ala Asp Ala Tyr
    3050                3055                3060
Tyr Leu Gly Gly Val Pro Pro Asp Gln Leu Pro Pro Ser Leu Arg
    3065                3070                3075
Arg Leu Phe Pro Thr Gly Gly Ser Val Arg Gly Cys Val Lys Gly
    3080                3085                3090
Ile Lys Ala Leu Gly Lys Tyr Val Asp Leu Lys Arg Leu Asn Thr
    3095                3100                3105
Thr Gly Val Ser Ala Gly Cys Thr Ala Asp Leu Leu Val Gly Arg
    3110                3115                3120
Ala Met Thr Phe His Gly His Gly Phe Leu Arg Leu Ala Leu Ser
    3125                3130                3135
Asn Val Ala Pro Leu Thr Gly Asn Val Tyr Ser Gly Phe Gly Phe
    3140                3145                3150
His Ser Ala Gln Asp Ser Ala Leu Leu Tyr Tyr Arg Ala Ser Pro
    3155                3160                3165
Asp Gly Leu Cys Gln Val Ser Leu Gln Gln Gly Arg Val Ser Leu
    3170                3175                3180
Gln Leu Leu Arg Thr Glu Val Lys Thr Gln Ala Gly Phe Ala Asp
    3185                3190                3195
Gly Ala Pro His Tyr Val Ala Phe Tyr Ser Asn Ala Thr Gly Val
    3200                3205                3210
Trp Leu Tyr Val Asp Asp Gln Leu Gln Gln Met Lys Pro His Arg
    3215                3220                3225
Gly Pro Pro Pro Glu Leu Gln Pro Gln Pro Glu Gly Pro Pro Arg
    3230                3235                3240
Leu Leu Leu Gly Gly Leu Pro Glu Ser Gly Thr Ile Tyr Asn Phe
    3245                3250                3255
Ser Gly Cys Ile Ser Asn Val Phe Val Gln Arg Leu Leu Gly Pro
    3260                3265                3270
Gln Arg Val Phe Asp Leu Gln Gln Asn Leu Gly Ser Val Asn Val
    3275                3280                3285
Ser Thr Gly Cys Ala Pro Ala Leu Gln Ala Gln Thr Pro Gly Leu
    3290                3295                3300
Gly Pro Arg Gly Leu Gln Ala Thr Ala Arg Lys Ala Ser Arg Arg
    3305                3310                3315
Ser Arg Gln Pro Ala Arg His Pro Ala Cys Met Leu Pro Pro His
    3320                3325                3330
Leu Arg Thr Thr Arg Asp Ser Tyr Gln Phe Gly Gly Ser Leu Ser
    3335                3340                3345
```

Ser His Leu Glu Phe Val Gly Ile Leu Ala Arg His Arg Asn Trp
3350                3355                3360

Pro Ser Leu Ser Met His Val Leu Pro Arg Ser Ser Arg Gly Leu
3365                3370                3375

Leu Leu Phe Thr Ala Arg Leu Arg Pro Gly Ser Pro Ser Leu Ala
3380                3385                3390

Leu Phe Leu Ser Asn Gly His Phe Val Ala Gln Met Glu Gly Leu
3395                3400                3405

Gly Thr Arg Leu Arg Ala Gln Ser Arg Gln Arg Ser Arg Pro Gly
3410                3415                3420

Arg Trp His Lys Val Ser Val Arg Trp Glu Lys Asn Arg Ile Leu
3425                3430                3435

Leu Val Thr Asp Gly Ala Arg Ala Trp Ser Gln Glu Gly Pro His
3440                3445                3450

Arg Gln His Gln Gly Ala Glu His Pro Gln Pro His Thr Leu Phe
3455                3460                3465

Val Gly Gly Leu Pro Ala Ser Ser His Ser Ser Lys Leu Pro Val
3470                3475                3480

Thr Val Gly Phe Ser Gly Cys Val Lys Arg Leu Arg Leu His Gly
3485                3490                3495

Arg Pro Leu Gly Ala Pro Thr Arg Met Ala Gly Val Thr Pro Cys
3500                3505                3510

Ile Leu Gly Pro Leu Glu Ala Gly Leu Phe Phe Pro Gly Ser Gly
3515                3520                3525

Gly Val Ile Thr Leu Asp Leu Pro Gly Ala Thr Leu Pro Asp Val
3530                3535                3540

Gly Leu Glu Leu Glu Val Arg Pro Leu Ala Val Thr Gly Leu Ile
3545                3550                3555

Phe His Leu Gly Gln Ala Arg Thr Pro Pro Tyr Leu Gln Leu Gln
3560                3565                3570

Val Thr Glu Lys Gln Val Leu Leu Arg Ala Asp Asp Gly Ala Gly
3575                3580                3585

Glu Phe Ser Thr Ser Val Thr Arg Pro Ser Val Leu Cys Asp Gly
3590                3595                3600

Gln Trp His Arg Leu Ala Val Met Lys Ser Gly Asn Val Leu Arg
3605                3610                3615

Leu Glu Val Asp Ala Gln Ser Asn His Thr Val Gly Pro Leu Leu
3620                3625                3630

Ala Ala Ala Ala Gly Ala Pro Ala Pro Leu Tyr Leu Gly Gly Leu
3635                3640                3645

Pro Glu Pro Met Ala Val Gln Pro Trp Pro Ala Tyr Cys Gly
3650                3655                3660

Cys Met Arg Arg Leu Ala Val Asn Arg Ser Pro Val Ala Met Thr
3665                3670                3675

Arg Ser Val Glu Val His Gly Ala Val Gly Ala Ser Gly Cys Pro
3680                3685                3690

Ala Ala
3695

<210> SEQ ID NO 2
<211> LENGTH: 1811
<212> TYPE: PRT
<213> ORGANISM: Homo sapiens

```
<400> SEQUENCE: 2

Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
            20                  25                  30

Gln Ala Pro Ala Pro Asp Val Pro Gly Cys Ser Arg Gly Ser Cys Tyr
        35                  40                  45

Pro Ala Thr Gly Asp Leu Leu Val Gly Arg Ala Asp Arg Leu Thr Ala
    50                  55                  60

Ser Ser Thr Cys Gly Leu Asn Gly Pro Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Ser His Arg Ile Gln Asn Val Val
            100                 105                 110

Thr Ser Phe Ala Pro Gln Arg Arg Ala Ala Trp Trp Gln Ser Glu Asn
        115                 120                 125

Gly Ile Pro Ala Val Thr Ile Gln Leu Asp Leu Glu Ala Glu Phe His
    130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
            180                 185                 190

Pro Pro Arg His Trp Asp Asp Val Val Cys Glu Ser Arg Tyr Ser Glu
        195                 200                 205

Ile Glu Pro Ser Thr Glu Gly Glu Val Ile Tyr Arg Val Leu Asp Pro
    210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
                245                 250                 255

Asp Asn Leu Leu Asp Pro Arg Arg Glu Ile Arg Glu Lys Tyr Tyr Tyr
            260                 265                 270

Ala Leu Tyr Glu Leu Val Val Arg Gly Asn Cys Phe Cys Tyr Gly His
        275                 280                 285

Ala Ser Glu Cys Ala Pro Ala Pro Gly Ala Pro Ala His Ala Glu Gly
    290                 295                 300

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
                325                 330                 335

Glu Asp Gly His Ser His Ala Cys Arg Lys Cys Glu Cys His Gly His
            340                 345                 350

Thr His Ser Cys His Phe Asp Met Ala Val Tyr Leu Ala Ser Gly Asn
        355                 360                 365

Val Ser Gly Gly Val Cys Asp Gly Cys Gln His Asn Thr Ala Gly Arg
    370                 375                 380

His Cys Glu Leu Cys Arg Pro Phe Phe Tyr Arg Asp Pro Thr Lys Asp
385                 390                 395                 400

Leu Arg Asp Pro Ala Val Cys Arg Ser Cys Asp Cys Asp Pro Met Gly
                405                 410                 415
```

```
Ser Gln Asp Gly Gly Arg Cys Asp Ser His Asp Asp Pro Ala Leu Gly
            420                 425                 430

Leu Val Ser Gly Gln Cys Arg Cys Lys Glu His Val Gly Thr Arg
            435                 440                 445

Cys Gln Gln Cys Arg Asp Gly Phe Phe Gly Leu Ser Ile Ser Asp Arg
            450                 455                 460

Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
                    485                 490                 495

Val Thr Gly Arg Gly Cys Asp Arg Cys Leu Pro Gly His Trp Gly Leu
                500                 505                 510

Ser His Asp Leu Leu Gly Cys Arg Pro Cys Asp Cys Asp Val Gly Gly
            515                 520                 525

Ala Leu Asp Pro Gln Cys Asp Glu Gly Thr Gly Gln Cys His Cys Arg
            530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                    565                 570                 575

Gln Val Leu Asp Val Val Glu Arg Leu Val Thr Pro Gly Glu Thr Pro
                580                 585                 590

Ser Trp Thr Gly Ser Gly Phe Val Arg Leu Gln Glu Gly Gln Thr Leu
            595                 600                 605

Glu Phe Leu Val Ala Ser Val Pro Lys Ala Met Asp Tyr Asp Leu Leu
            610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                    645                 650                 655

Leu Val Pro Lys Asp Asp Arg Ile Gln Gly Thr Leu Gln Pro His Ala
                660                 665                 670

Arg Tyr Leu Ile Phe Pro Asn Pro Val Cys Leu Glu Pro Gly Ile Ser
            675                 680                 685

Tyr Lys Leu His Leu Lys Leu Val Arg Thr Gly Gly Ser Ala Gln Pro
            690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                    725                 730                 735

Ala Leu Glu Arg Gln Ala Thr Phe Glu Arg Tyr Gln Cys His Glu Glu
                740                 745                 750

Gly Leu Val Pro Ser Lys Thr Ser Pro Ser Glu Ala Cys Ala Pro Leu
            755                 760                 765

Leu Ile Ser Leu Ser Thr Leu Ile Tyr Asn Gly Ala Leu Pro Cys Gln
            770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Leu Cys
                    805                 810                 815

Ala Pro Gly Tyr Tyr Gly Phe Gly Pro Thr Gly Cys Gln Ala Cys Gln
                820                 825                 830
```

-continued

```
Cys Ser His Glu Gly Ala Leu Ser Leu Cys Glu Lys Thr Ser Gly
            835                 840                 845

Gln Cys Leu Cys Arg Thr Gly Ala Phe Gly Leu Arg Cys Asp Arg Cys
850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                885                 890                 895

Arg Asp His Thr Gly Gly Glu His Cys Glu Arg Cys Ile Ala Gly Phe
            900                 905                 910

His Gly Asp Pro Arg Leu Pro Tyr Gly Gly Gln Cys Arg Pro Cys Pro
            915                 920                 925

Cys Pro Glu Gly Pro Gly Ser Gln Arg His Phe Ala Thr Ser Cys His
        930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly His Phe Gly Asp Pro
                965                 970                 975

Ser Arg Pro Gly Gly Arg Cys Gln Leu Cys Glu Cys Ser Gly Asn Ile
            980                 985                 990

Asp Pro Met Asp Pro Asp Ala Cys Asp Pro His Thr Gly Gln Cys Leu
        995                 1000                1005

Arg Cys Leu His His Thr Glu Gly Pro His Cys Ala His Cys Lys
1010                1015                1020

Pro Gly Phe His Gly Gln Ala Arg Gln Ser Cys His Arg Cys
    1025                1030                1035

Thr Cys Asn Leu Leu Gly Thr Asn Pro Gln Gln Cys Pro Ser Pro
    1040                1045                1050

Asp Gln Cys His Cys Asp Pro Ser Ser Gly Gln Cys Pro Cys Leu
    1055                1060                1065

Pro Asn Val Gln Gly Pro Ser Cys Asp Arg Cys Ala Pro Asn Phe
    1070                1075                1080

Trp Asn Leu Thr Ser Gly His Gly Cys Gln Pro Cys Ala Cys His
    1085                1090                1095

Pro Ser Arg Ala Arg Gly Pro Thr Cys Asn Glu Phe Thr Gly Gln
    1100                1105                1110

Cys His Cys Arg Ala Gly Phe Gly Gly Arg Thr Cys Ser Glu Cys
    1115                1120                1125

Gln Glu Leu His Trp Gly Asp Pro Gly Leu Gln Cys His Ala Cys
    1130                1135                1140

Asp Cys Asp Ser Arg Gly Ile Asp Thr Pro Gln Cys His Arg Phe
    1145                1150                1155

Thr Gly His Cys Ser Cys Arg Pro Gly Val Ser Gly Val Arg Cys
    1160                1165                1170

Asp Gln Cys Ala Arg Gly Phe Ser Gly Ile Phe Pro Ala Cys His
    1175                1180                1185

Pro Cys His Ala Cys Phe Gly Asp Trp Asp Arg Val Val Gln Asp
    1190                1195                1200

Leu Ala Ala Arg Thr Gln Arg Leu Glu Gln Arg Ala Gln Glu Leu
    1205                1210                1215

Gln Gln Thr Gly Val Leu Gly Ala Phe Glu Ser Ser Phe Trp His
    1220                1225                1230

Met Gln Glu Lys Leu Gly Ile Val Gln Gly Ile Val Gly Ala Arg
```

```
              1235                1240                1245

Asn Thr Ser Ala Ala Ser Thr Ala Gln Leu Val Glu Ala Thr Glu
            1250                1255                1260

Glu Leu Arg Arg Glu Ile Gly Glu Ala Thr His Leu Thr Gln
            1265                1270                1275

Leu Glu Ala Asp Leu Thr Asp Val Gln Asp Glu Asn Phe Asn Ala
            1280                1285                1290

Asn His Ala Leu Ser Gly Leu Glu Arg Asp Arg Leu Ala Leu Asn
            1295                1300                1305

Leu Thr Leu Arg Gln Leu Asp Gln His Leu Asp Leu Leu Lys His
            1310                1315                1320

Ser Asn Phe Leu Gly Ala Tyr Asp Ser Ile Arg His Ala His Ser
            1325                1330                1335

Gln Ser Ala Glu Ala Glu Arg Arg Ala Asn Thr Ser Ala Leu Ala
            1340                1345                1350

Val Pro Ser Pro Val Ser Asn Ser Ala Ser Ala Arg His Arg Thr
            1355                1360                1365

Glu Ala Leu Met Asp Ala Gln Lys Glu Asp Phe Asn Ser Lys His
            1370                1375                1380

Met Ala Asn Gln Arg Ala Leu Gly Lys Leu Ser Ala His Thr His
            1385                1390                1395

Thr Leu Ser Leu Thr Asp Ile Asn Glu Leu Val Cys Gly Ala Pro
            1400                1405                1410

Gly Asp Ala Pro Cys Ala Thr Ser Pro Cys Gly Ala Gly Cys
            1415                1420                1425

Arg Asp Glu Asp Gly Gln Pro Arg Cys Gly Gly Leu Ser Cys Asn
            1430                1435                1440

Gly Ala Ala Thr Ala Asp Leu Ala Leu Gly Arg Ala Arg His
            1445                1450                1455

Thr Gln Ala Glu Leu Gln Arg Ala Leu Ala Glu Gly Gly Ser Ile
            1460                1465                1470

Leu Ser Arg Val Ala Glu Thr Arg Arg Gln Ala Ser Glu Ala Gln
            1475                1480                1485

Gln Arg Ala Gln Ala Ala Leu Asp Lys Ala Asn Ala Ser Arg Gly
            1490                1495                1500

Gln Val Glu Gln Ala Asn Gln Glu Leu Gln Glu Leu Ile Gln Ser
            1505                1510                1515

Val Lys Asp Phe Leu Asn Gln Glu Gly Ala Asp Pro Asp Ser Ile
            1520                1525                1530

Glu Met Val Ala Thr Arg Val Leu Glu Leu Ser Ile Pro Ala Ser
            1535                1540                1545

Ala Glu Gln Ile Gln His Leu Ala Gly Ala Ile Ala Glu Arg Val
            1550                1555                1560

Arg Ser Leu Ala Asp Val Asp Ala Ile Leu Ala Arg Thr Val Gly
            1565                1570                1575

Asp Val Arg Arg Ala Glu Gln Leu Leu Gln Asp Ala Arg Arg Ala
            1580                1585                1590

Arg Ser Trp Ala Glu Asp Glu Lys Gln Lys Ala Glu Thr Val Gln
            1595                1600                1605

Ala Ala Leu Glu Glu Ala Gln Arg Ala Gln Gly Ile Ala Gln Gly
            1610                1615                1620

Ala Ile Arg Gly Ala Val Ala Asp Thr Arg Asp Thr Glu Gln Thr
            1625                1630                1635
```

```
Leu Tyr Gln Val Gln Glu Arg Met Ala Gly Ala Glu Arg Ala Leu
    1640                1645                1650

Ser Ser Ala Gly Glu Arg Ala Arg Gln Leu Asp Ala Leu Leu Glu
    1655                1660                1665

Ala Leu Lys Leu Lys Arg Ala Gly Asn Ser Leu Ala Ala Ser Thr
    1670                1675                1680

Ala Glu Glu Thr Ala Gly Ser Ala Gln Gly Arg Ala Gln Glu Ala
    1685                1690                1695

Glu Gln Leu Leu Arg Gly Pro Leu Gly Asp Gln Tyr Gln Thr Val
    1700                1705                1710

Lys Ala Leu Ala Glu Arg Lys Ala Gln Gly Val Leu Ala Ala Gln
    1715                1720                1725

Ala Arg Ala Glu Gln Leu Arg Asp Glu Ala Arg Asp Leu Leu Gln
    1730                1735                1740

Ala Ala Gln Asp Lys Leu Gln Arg Leu Gln Glu Leu Glu Gly Thr
    1745                1750                1755

Tyr Glu Glu Asn Glu Arg Ala Leu Glu Ser Lys Ala Ala Gln Leu
    1760                1765                1770

Asp Gly Leu Glu Ala Arg Met Arg Ser Val Leu Gln Ala Ile Asn
    1775                1780                1785

Leu Gln Val Gln Ile Tyr Asn Thr Cys Gln Lys Ser Ser Trp Pro
    1790                1795                1800

Gly Arg Ala Pro Asn Lys Pro Val
    1805                1810

<210> SEQ ID NO 3
<211> LENGTH: 1609
<212> TYPE: PRT
<213> ORGANISM: Homo sapiens

<400> SEQUENCE: 3

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
                20                  25                  30

Ala Gln Ala Ala Met Asp Glu Cys Thr Asp Glu Gly Gly Arg Pro Gln
            35                  40                  45

Arg Cys Met Pro Glu Phe Val Asn Ala Ala Phe Asn Val Thr Val Val
    50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
                85                  90                  95

Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
        115                 120                 125

Tyr Pro Ser Ser Ile Asn Leu Thr Leu His Leu Gly Lys Ala Phe Asp
    130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
```

```
                180                 185                 190
Phe Ile Arg Thr Gly Gly Asp Glu Gln Gln Ala Leu Cys Thr Asp Glu
            195                 200                 205

Phe Ser Asp Ile Ser Pro Leu Thr Gly Gly Asn Val Ala Phe Ser Thr
210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                245                 250                 255

Asn Thr Phe Gly Asp Glu Val Phe Asn Asp Pro Lys Val Leu Lys Ser
            260                 265                 270

Tyr Tyr Tyr Ala Ile Ser Asp Phe Ala Val Gly Gly Arg Cys Lys Cys
        275                 280                 285

Asn Gly His Ala Ser Glu Cys Met Lys Asn Glu Phe Asp Lys Leu Val
        290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                325                 330                 335

Ser Glu Cys Leu Pro Cys Asp Cys Asn Gly Arg Ser Gln Glu Cys Tyr
            340                 345                 350

Phe Asp Pro Glu Leu Tyr Arg Ser Thr Gly His Gly Gly His Cys Thr
        355                 360                 365

Asn Cys Gln Asp Asn Thr Asp Gly Ala His Cys Glu Arg Cys Arg Glu
    370                 375                 380

Asn Phe Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
                405                 410                 415

Ser Cys Lys Pro Gly Val Met Gly Asp Lys Cys Asp Arg Cys Gln Pro
            420                 425                 430

Gly Phe His Ser Leu Thr Glu Ala Gly Cys Arg Pro Cys Ser Cys Asp
        435                 440                 445

Pro Ser Gly Ser Ile Asp Glu Cys Asn Ile Glu Thr Gly Arg Cys Val
    450                 455                 460

Cys Lys Asp Asn Val Glu Gly Phe Asn Cys Glu Arg Cys Lys Pro Gly
465                 470                 475                 480

Phe Phe Asn Leu Glu Ser Ser Asn Pro Arg Gly Cys Thr Pro Cys Phe
                485                 490                 495

Cys Phe Gly His Ser Ser Val Cys Thr Asn Ala Val Gly Tyr Ser Val
            500                 505                 510

Tyr Ser Ile Ser Ser Thr Phe Gln Ile Asp Glu Asp Gly Trp Arg Ala
        515                 520                 525

Glu Gln Arg Asp Gly Ser Glu Ala Ser Leu Glu Trp Ser Ser Glu Arg
    530                 535                 540

Gln Asp Ile Ala Val Ile Ser Asp Ser Tyr Phe Pro Arg Tyr Phe Ile
545                 550                 555                 560

Ala Pro Ala Lys Phe Leu Gly Lys Gln Val Leu Ser Tyr Gly Gln Asn
                565                 570                 575

Leu Ser Phe Ser Phe Arg Val Asp Arg Arg Asp Thr Arg Leu Ser Ala
            580                 585                 590

Glu Asp Leu Val Leu Glu Gly Ala Gly Leu Arg Val Ser Val Pro Leu
        595                 600                 605
```

```
Ile Ala Gln Gly Asn Ser Tyr Pro Ser Glu Thr Thr Val Lys Tyr Val
610             615                 620

Phe Arg Leu His Glu Ala Thr Asp Tyr Pro Trp Arg Pro Ala Leu Thr
625                 630                 635                 640

Pro Phe Glu Phe Gln Lys Leu Leu Asn Asn Leu Thr Ser Ile Lys Ile
            645                 650                 655

Arg Gly Thr Tyr Ser Glu Arg Ser Ala Gly Tyr Leu Asp Asp Val Thr
                660                 665                 670

Leu Ala Ser Ala Arg Pro Gly Pro Gly Val Pro Ala Thr Trp Val Glu
            675                 680                 685

Ser Cys Thr Cys Pro Val Gly Tyr Gly Gly Gln Phe Cys Glu Met Cys
690                 695                 700

Leu Ser Gly Tyr Arg Arg Glu Thr Pro Asn Leu Gly Pro Tyr Ser Pro
705                 710                 715                 720

Cys Val Leu Cys Ala Cys Asn Gly His Ser Glu Thr Cys Asp Pro Glu
                725                 730                 735

Thr Gly Val Cys Asn Cys Arg Asp Asn Thr Ala Gly Pro His Cys Glu
                740                 745                 750

Lys Cys Ser Asp Gly Tyr Tyr Gly Asp Ser Thr Ala Gly Thr Ser Ser
            755                 760                 765

Asp Cys Gln Pro Cys Pro Cys Pro Gly Gly Ser Ser Cys Ala Val Val
            770                 775                 780

Pro Lys Thr Lys Glu Val Val Cys Thr Asn Cys Pro Thr Gly Thr Thr
785                 790                 795                 800

Gly Lys Arg Cys Glu Leu Cys Asp Asp Gly Tyr Phe Gly Asp Pro Leu
                805                 810                 815

Gly Arg Asn Gly Pro Val Arg Leu Cys Arg Leu Cys Gln Cys Ser Asp
            820                 825                 830

Asn Ile Asp Pro Asn Ala Val Gly Asn Cys Asn Arg Leu Thr Gly Glu
835                 840                 845

Cys Leu Lys Cys Ile Tyr Asn Thr Ala Gly Phe Tyr Cys Asp Arg Cys
850                 855                 860

Lys Asp Gly Phe Phe Gly Asn Pro Leu Ala Pro Asn Pro Ala Asp Lys
865                 870                 875                 880

Cys Lys Ala Cys Asn Cys Asn Leu Tyr Gly Thr Met Lys Gln Gln Ser
            885                 890                 895

Ser Cys Asn Pro Val Thr Gly Gln Cys Glu Cys Leu Pro His Val Thr
            900                 905                 910

Gly Gln Asp Cys Gly Ala Cys Asp Pro Gly Phe Tyr Asn Leu Gln Ser
            915                 920                 925

Gly Gln Gly Cys Glu Arg Cys Asp Cys His Ala Leu Gly Ser Thr Asn
930                 935                 940

Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
                965                 970                 975

Pro Glu Gly Cys Lys Pro Cys Asp Cys His Pro Glu Gly Ser Leu Ser
            980                 985                 990

Leu Gln Cys Lys Asp Asp Gly Arg  Cys Glu Cys Arg Glu Gly Phe Val
        995             1000                1005

Gly Asn Arg Cys Asp Gln Cys  Glu Glu Asn Tyr Phe  Tyr Asn Arg
    1010            1015                1020
```

-continued

| | | | | | | | | | | | | |
|---|---|---|---|---|---|---|---|---|---|---|---|---|
| Ser | Trp | Pro | Gly | Cys | Gln | Glu | Cys | Pro | Ala | Cys | Tyr | Arg Leu Val |
| | 1025 | | | | 1030 | | | | 1035 | | | |
| Lys | Asp | Lys | Val | Ala | Asp | His | Arg | Val | Lys | Leu | Gln | Glu Leu Glu |
| | 1040 | | | | 1045 | | | | 1050 | | | |
| Ser | Leu | Ile | Ala | Asn | Leu | Gly | Thr | Gly | Asp | Glu | Met | Val Thr Asp |
| | 1055 | | | | 1060 | | | | 1065 | | | |
| Gln | Ala | Phe | Glu | Asp | Arg | Leu | Lys | Glu | Ala | Glu | Arg | Glu Val Met |
| | 1070 | | | | 1075 | | | | 1080 | | | |
| Asp | Leu | Leu | Arg | Glu | Ala | Gln | Asp | Val | Lys | Asp | Val | Asp Gln Asn |
| | 1085 | | | | 1090 | | | | 1095 | | | |
| Leu | Met | Asp | Arg | Leu | Gln | Arg | Val | Asn | Asn | Thr | Leu | Ser Ser Gln |
| | 1100 | | | | 1105 | | | | 1110 | | | |
| Ile | Ser | Arg | Leu | Gln | Asn | Ile | Arg | Asn | Thr | Ile | Glu | Glu Thr Gly |
| | 1115 | | | | 1120 | | | | 1125 | | | |
| Asn | Leu | Ala | Glu | Gln | Ala | Arg | Ala | His | Val | Glu | Asn | Thr Glu Arg |
| | 1130 | | | | 1135 | | | | 1140 | | | |
| Leu | Ile | Glu | Ile | Ala | Ser | Arg | Glu | Leu | Glu | Lys | Ala | Lys Val Ala |
| | 1145 | | | | 1150 | | | | 1155 | | | |
| Ala | Ala | Asn | Val | Ser | Val | Thr | Gln | Pro | Glu | Ser | Thr | Gly Asp Pro |
| | 1160 | | | | 1165 | | | | 1170 | | | |
| Asn | Asn | Met | Thr | Leu | Leu | Ala | Glu | Glu | Ala | Arg | Lys | Leu Ala Glu |
| | 1175 | | | | 1180 | | | | 1185 | | | |
| Arg | His | Lys | Gln | Glu | Ala | Asp | Asp | Ile | Val | Arg | Val | Ala Lys Thr |
| | 1190 | | | | 1195 | | | | 1200 | | | |
| Ala | Asn | Asp | Thr | Ser | Thr | Glu | Ala | Tyr | Asn | Leu | Leu | Leu Arg Thr |
| | 1205 | | | | 1210 | | | | 1215 | | | |
| Leu | Ala | Gly | Glu | Asn | Gln | Thr | Ala | Phe | Glu | Ile | Glu | Glu Leu Asn |
| | 1220 | | | | 1225 | | | | 1230 | | | |
| Arg | Lys | Tyr | Glu | Gln | Ala | Lys | Asn | Ile | Ser | Gln | Asp | Leu Glu Lys |
| | 1235 | | | | 1240 | | | | 1245 | | | |
| Gln | Ala | Ala | Arg | Val | His | Glu | Glu | Ala | Lys | Arg | Ala | Gly Asp Lys |
| | 1250 | | | | 1255 | | | | 1260 | | | |
| Ala | Val | Glu | Ile | Tyr | Ala | Ser | Val | Ala | Gln | Leu | Ser | Pro Leu Asp |
| | 1265 | | | | 1270 | | | | 1275 | | | |
| Ser | Glu | Thr | Leu | Glu | Asn | Glu | Ala | Asn | Asn | Ile | Lys | Met Glu Ala |
| | 1280 | | | | 1285 | | | | 1290 | | | |
| Glu | Asn | Leu | Glu | Gln | Leu | Ile | Asp | Gln | Lys | Leu | Lys | Asp Tyr Glu |
| | 1295 | | | | 1300 | | | | 1305 | | | |
| Asp | Leu | Arg | Glu | Asp | Met | Arg | Gly | Lys | Glu | Leu | Glu | Val Lys Asn |
| | 1310 | | | | 1315 | | | | 1320 | | | |
| Leu | Leu | Glu | Lys | Gly | Lys | Thr | Glu | Gln | Gln | Thr | Ala | Asp Gln Leu |
| | 1325 | | | | 1330 | | | | 1335 | | | |
| Leu | Ala | Arg | Ala | Asp | Ala | Ala | Lys | Ala | Leu | Ala | Glu | Glu Ala Ala |
| | 1340 | | | | 1345 | | | | 1350 | | | |
| Lys | Lys | Gly | Arg | Asp | Thr | Leu | Gln | Glu | Ala | Asn | Asp | Ile Leu Asn |
| | 1355 | | | | 1360 | | | | 1365 | | | |
| Asn | Leu | Lys | Asp | Phe | Asp | Arg | Arg | Val | Asn | Asp | Asn | Lys Thr Ala |
| | 1370 | | | | 1375 | | | | 1380 | | | |
| Ala | Glu | Glu | Ala | Leu | Arg | Lys | Ile | Pro | Ala | Ile | Asn | Gln Thr Ile |
| | 1385 | | | | 1390 | | | | 1395 | | | |
| Thr | Glu | Ala | Asn | Glu | Lys | Thr | Arg | Glu | Ala | Gln | Gln | Ala Leu Gly |
| | 1400 | | | | 1405 | | | | 1410 | | | |
| Ser | Ala | Ala | Ala | Asp | Ala | Thr | Glu | Ala | Lys | Asn | Lys | Ala His Glu |

| | | | | | | | | | | | |
|---|---|---|---|---|---|---|---|---|---|---|---|
| | 1415 | | | 1420 | | | | 1425 | | | |
| Ala | Glu | Arg | Ile | Ala | Ser | Ala | Val | Gln | Lys | Asn | Ala | Thr | Ser | Thr |
| | 1430 | | | | 1435 | | | | 1440 | | |
| Lys | Ala | Glu | Ala | Glu | Arg | Thr | Phe | Ala | Glu | Val | Thr | Asp | Leu | Asp |
| | 1445 | | | | 1450 | | | | 1455 | | |
| Asn | Glu | Val | Asn | Asn | Met | Leu | Lys | Gln | Leu | Gln | Glu | Ala | Glu | Lys |
| | 1460 | | | | 1465 | | | | 1470 | | |
| Glu | Leu | Lys | Arg | Lys | Gln | Asp | Asp | Ala | Asp | Gln | Asp | Met | Met | Met |
| | 1475 | | | | 1480 | | | | 1485 | | |
| Ala | Gly | Met | Ala | Ser | Gln | Ala | Ala | Gln | Glu | Ala | Glu | Ile | Asn | Ala |
| | 1490 | | | | 1495 | | | | 1500 | | |
| Arg | Lys | Ala | Lys | Asn | Ser | Val | Thr | Ser | Leu | Leu | Ser | Ile | Ile | Asn |
| | 1505 | | | | 1510 | | | | 1515 | | |
| Asp | Leu | Leu | Glu | Gln | Leu | Gly | Gln | Leu | Asp | Thr | Val | Asp | Leu | Asn |
| | 1520 | | | | 1525 | | | | 1530 | | |
| Lys | Leu | Asn | Glu | Ile | Glu | Gly | Thr | Leu | Asn | Lys | Ala | Lys | Asp | Glu |
| | 1535 | | | | 1540 | | | | 1545 | | |
| Met | Lys | Val | Ser | Asp | Leu | Asp | Arg | Lys | Val | Ser | Asp | Leu | Glu | Asn |
| | 1550 | | | | 1555 | | | | 1560 | | |
| Glu | Ala | Lys | Lys | Gln | Glu | Ala | Ala | Ile | Met | Asp | Tyr | Asn | Arg | Asp |
| | 1565 | | | | 1570 | | | | 1575 | | |
| Ile | Glu | Glu | Ile | Met | Lys | Asp | Ile | Arg | Asn | Leu | Glu | Asp | Ile | Arg |
| | 1580 | | | | 1585 | | | | 1590 | | |
| Lys | Thr | Leu | Pro | Ser | Gly | Cys | Phe | Asn | Thr | Pro | Ser | Ile | Glu | Lys |
| | 1595 | | | | 1600 | | | | 1605 | | |

Pro

<210> SEQ ID NO 4
<211> LENGTH: 5518
<212> TYPE: DNA
<213> ORGANISM: Homo sapiens

<400> SEQUENCE: 4

| | | | | | |
|---|---|---|---|---|---|
| atggagctga | cctcaaggga | aagagggagg | ggacagcctc | tgccctggga | acttcgactg | 60 |
| ggcctactgc | taagcgtgct | ggctgccaca | ctggcacagg | cccctgcccc | ggatgtgcct | 120 |
| ggctgttcca | ggggaagctg | ctaccccgcc | acgggcgacc | tgctggtggg | ccagagctga | 180 |
| agactgactg | cctcatccac | ttgtggcctg | aatggccccc | agccctactg | catcgtcagt | 240 |
| cacctgcagg | acgaaaagaa | gtgcttcctt | tgtgactccc | ggcgcccctt | ctctgctaga | 300 |
| gacaacccac | acagccatcg | catccagaat | gtagtcacca | gctttgcacc | acagcggcgg | 360 |
| gcagcctggt | ggcagtcaga | gaatggtatc | cctgcggtca | ccatccagct | ggacctggag | 420 |
| gctgagtttc | atttcacaca | cctcattatg | accttcaaga | catttcgccc | tgctgccatg | 480 |
| ctggtggaac | gctcagcaga | ctttggccgc | acctggcatg | tgtaccgata | tttctcctat | 540 |
| gactgtgggg | ctgacttccc | aggagtccca | ctagcacccc | cacggcactg | ggatgatgta | 600 |
| gtctgtgagt | cccgctactc | agagattgag | ccatccactg | aaggcgaggt | catctatcgt | 660 |
| gtgctggacc | ctgccatccc | tatcccagac | ccctacagct | cacggattca | gaacctgttg | 720 |
| aagatcacca | acctacgggt | gaacctgact | cgtctacaca | cgttgggaga | caacctactc | 780 |
| gacccacgga | gggagatccg | agagaagtac | tactatgccc | tctatgagct | ggttgtacgt | 840 |
| ggcaactgct | tctgctacgg | acacgcctca | gagtgtgcac | ccgccccagg | gcaccagcc | 900 |
| catgctgagg | gcatggtgca | cggagcttgc | atctgcaaac | acaacacacg | tggcctcaac | 960 |

```
tgcgagcagt gtcaggattt ctatcgtgac ctgccctggc gtccggctga ggacggccat    1020
agtcatgcct gtaggaagtg tgagtgccat gggcacaccc acagctgcca cttcgacatg    1080
gccgtatacc tggcatctgg caatgtgagt ggaggtgtgt gtgatggatg tcagcataac    1140
acagctgggc gccactgtga gctctgtcgg cccttcttct accgtgaccc aaccaaggac    1200
ctgcgggatc cggctgtgtg ccgctcctgt gattgtgacc ccatgggttc tcaagacggt    1260
ggtcgctgtg attcccatga tgaccctgca ctgggactgg tctccggcca gtgtcgctgc    1320
aaagaacatg tggtgggcac tcgctgccag caatgccgtg atggcttctt tgggctcagc    1380
atcagtgacc gtctgggctg ccggcgatgt caatgtaatg cacggggcac agtgcctggg    1440
agcactcctt gtgaccccaa cagtggatcc tgttactgca aacgtctagt gactggacgt    1500
ggatgtgacc gctgcctgcc tggccactgg ggcctgagcc acgacctgct cggctgccgc    1560
ccctgtgact gcgacgtggg tggtgctttg gatccccagt gtgatgaggg cacaggtcaa    1620
tgccactgcc gccagcacat ggttgggcga cgctgtgagc aggtgcaacc tggctacttc    1680 cggccccttcc tggaccacct aatttgggag gctgaggaca cccgagggca ggtgctcgat    1740
gtggtggagc gcctggtgac ccccggggaa actccatcct ggactggctc aggcttcgtg    1800
cggctacagg aaggtcagac cctggagttc ctggtggcct ctgtgccgaa ggctatggac    1860
tatgacctgc tgctgcgctt agagccccag gtccctgagc aatgggcaga gttggaactg    1920
attgtgcagc gtccagggcc tgtgcctgcc cacagcctgt gtgggcattt ggtgcccaag    1980
gatgatcgca tccaagggac tctgcaacca catgccaggt acttgatatt tcctaatcct    2040
gtctgccttg agcctggtat tcctacaag ctgcatctga gctggtacg gacaggggga    2100 agtgcccagc ctgagactcc ctactctgga cctggcctgc tcattgactc gctggtgctg    2160
ctgccccgtg tcctggtgct agagatgttt agtgggggtg atgctgctgc cctggagcgc    2220
caggccacct ttgaacgcta ccaatgccat gaggagggtc tggtgcccag caagacttct    2280
ccctctgagg cctgcgcacc cctcctcatc agcctgtcca ccctcatcta caatggtgcc    2340
ctgccatgtc agtgcaaccc tcaaggttca ctgagttctg agtgcaaccc tcatggtggt    2400
cagtgcctgt gcaagcctgg agtggttggg cgccgctgtg acctctgtgc ccctggctac    2460
tatggctttg cccccacagg ctgtcaagcc tgccagtgca gccacgaggg ggcactcagc    2520
agtctctgtg aaaagaccag tgggcaatgt ctctgtcgaa ctggtgcctt gggcttcgc    2580 tgtgaccgct gccagcgtgg ccagtgggga ttccctagct gccggccatg tgtctgcaat    2640
gggcatgcag atgagtgcaa cacccacaca ggcgcttgcc tgggctgccg tgatcacaca    2700
gggggtgagc actgtgaaag gtgcattgct ggtttccacg gggacccacg gctgccatat    2760
gggggccagt gccggccctg tccctgtcct gaaggccctg ggagccaacg gcactttgct    2820
acttcttgcc accaggatga atattcccag cagattgtgt gccactgccg ggcaggctat    2880
acggggctgc gatgtgaagc ttgtgcccct ggcactttg ggacccatc aaggccaggt    2940 ggccggtgcc aactgtgtga gtgcagtggg aacattgacc caatggatcc tgatgcctgt    3000
gacccccaca cggggcaatg cctgcgctgt ttacaccaca cagagggtcc acactgtgcc    3060
cactgcaagc ctggcttcca tgggcaggct gcccgacaga gctgtcaccg ctgcacatgc    3120
aacctgctgg gcacaaatcc gcagcagtgc cactcctg accagtgcca ctgtgatcca    3180
agcagtggcc agtgcccatg cctccccaat gtccagggcc ctagctgtga ccgctgtgcc    3240
cccaacttct ggaacctcac cagtggccat ggttgccagc cttgtgcctg ccacccaagc    3300
```

-continued

| | |
|---|---|
| cgggccagag gccccacctg caacgagttc acagggcagt gccactgccg tgccggcttt | 3360 |
| ggagggcgga cttgttctga gtgccaagag ctccactggg gagaccctgg gttgcagtgc | 3420 |
| catgcctgtg attgtgactc tcgtggaata gatacacctc agtgtcaccg cttcacaggt | 3480 |
| cactgcagct gccgcccagg ggtgtctggt gtgcgctgtg accagtgtgc ccgtggcttc | 3540 |
| tcaggaatct ttcctgcctg ccatccctgc catgcatgct tcggggattg ggaccgagtg | 3600 |
| gtgcaggact tggcagcccg tacacagcgc ctagagcagc gggcgcagga gttgcaacag | 3660 |
| acgggtgtgc tgggtgcctt tgagagcagc ttctggcaca tgcaggagaa gctgggcatt | 3720 |
| gtgcagggca tcgtaggtgc ccgcaacacc tcagccgcct ccactgcaca gcttgtggag | 3780 |
| gccacagagg agctgcggcg tgaaattggg gaggccactg agcacctgac tcagctcgag | 3840 |
| gcagacctga cagatgtgca agatgagaac ttcaatgcca accatgcact aagtggtctg | 3900 |
| gagcgagata ggcttgcact taatctcaca ctgcggcagc tcgaccagca tcttgacttg | 3960 |
| ctcaaacatt caaacttcct gggtgcctat gacagcatcc ggcatgccca tagccagtct | 4020 |
| gcagaggcag aacgtcgtgc caatacctca gccctggcag tacctagccc tgtgagcaac | 4080 |
| tcggcaagtg ctcggcatcg gacagaggca ctgatggatg ctcagaagga ggacttcaac | 4140 |
| agcaaacaca tggccaacca gcgggcactt ggcaagctct ctgcccatac ccacaccctg | 4200 |
| agcctgacag acataaatga gctggtgtgt ggggcaccag gggatgcacc ctgtgctaca | 4260 |
| agcccttgtg ggggtgccgg ctgtcgagat gaggatgggc agccgcgctg tgggggcctc | 4320 |
| agctgcaatg gggcagcggc tacagcagac ctagcactgg gccgggcccg gcacacacag | 4380 |
| gcagagctgc agcgggcact ggcagaaggt ggtagcatcc tcagcagagt ggctgagact | 4440 |
| cgtcggcagg caagcgaggc acagcagcgg gcccaggcag ccctggacaa ggctaatgct | 4500 |
| tccaggggac aggtggaaca ggccaaccag gaacttcaag aacttatcca gagtgtgaag | 4560 |
| gacttcctca accaggaggg ggctgatcct gatagcattg aaatggtggc cacacgggtg | 4620 |
| ctagagctct ccatcccagc ttcagctgag cagatccagc acctggcggg tgcgattgca | 4680 |
| gagcgagtcc ggagcctggc agatgtggat gcgatcctgg cacgtactgt aggagatgtg | 4740 |
| cgtcgtgccg agcagctact gcaggatgca cggcgggcaa ggagctgggc tgaggatgag | 4800 |
| aaacagaagg cagagacagt acaggcagca ctggaggagg cccagcgggc acagggtatt | 4860 |
| gcccagggtg ccatccgggg ggcagtggct gacacacggg acacagagca gaccctgtac | 4920 |
| caggtacagg agaggatggc aggtgcagag cgggcactga gctctgcagg tgaaagggct | 4980 |
| cggcagttgg atgctctcct ggaggctctg aaattgaaac gggcaggaaa tagtctggca | 5040 |
| gcctctacag cagaagaaac ggcaggcagt gcccagggtc gtgcccagga ggctgagcag | 5100 |
| ctgctacgcg gtcctctggg tgatcagtac cagacggtga aggccctagc tgagcgcaag | 5160 |
| gcccaaggtg tgctggctgc acaggcaagg gcagaacaac tgcgggatga ggctcgggac | 5220 |
| ctgttgcaag ccgctcagga caagctgcag cggctacagg aattggaagg cacctatgag | 5280 |
| gaaaatgagc gggcactgga gagtaaggca gcccagttgg acgggttgga ggccaggatg | 5340 |
| cgcagcgtgc ttcaagccat caacttgcag gtgcagatct acaacacctg ccagtgaccc | 5400 |
| ctgcccaagg cctaccccag ttcctagcac tgccccacat gcatgtctgc ctatgcactg | 5460 |
| aagagctctt ggcccggcag ggcccccaat aaaccagtgt gaacccccaa aaaaaaaa | 5518 |

<210> SEQ ID NO 5
<211> LENGTH: 11426
<212> TYPE: DNA
<213> ORGANISM: Homo sapiens

<400> SEQUENCE: 5

```
agacccgccg ggctcccgcc gcgcgcgctg tccctggagc tcggggacgc ggcccggagc    60
cgggaagatg gcgaagcggc tctgcgcggg gagcgcactg tgtgttcgcg gcccccgggg   120
ccccgcgccg ctgctgctgg tcgggctggc gctgctgggc gcggcgcggg cgcgggagga   180
ggcgggcggc ggcttcagcc tgcacccgcc ctacttcaac ctggccgagg gcgcccgcat   240
cgccgcctcc gcgacctgcg gagaggaggc cccggcgcgc ggctcccgc gccccaccga   300
ggacctttac tgcaagctgg taggggggccc cgtggccggc ggcgacccca accagaccat   360
ccggggccag tactgtgaca tctgcacggc tgccaacagc aacaaggcac accccgcgag   420
caatgccatc gatggcacgg agcgctggtg gcagagtcca ccgctgtccc gcggcctgga   480
gtacaacgag gtcaacgtca ccctggacct gggccaggtc ttccacgtgg cctacgtcct   540
catcaagttt gccaactcac cccggccgga cctctgggtg ctggagcggt ccatggactt   600
cggccgcacc taccagccct ggcagttctt tgcctcctcc aagagggact gtctggagcg   660
gttcgggcca cagacgctgg agcgcatcac acgggacgac gcggccatct gcaccaccga   720
gtactcacgc atcgtgcccc tggagaacgg agagatcgtg gtgtccctgg tgaacggacg   780
tccgggcgcc atgaatttct cctactcgcc gctgctacgt gagttcacca aggccaccaa   840
cgtccgcctg cgcttcctgc gtaccaacac gctgctgggc catctcatgg ggaaggcgct   900
gcgggacccc acggtcaccc gccggtatta ttacagcatc aaggatatca gcatcggagg   960
ccgctgtgtc tgccacggcc acgcggatgc ctgcgatgcc aaagaccca cggacccgtt  1020
caggctgcag tgcacctgcc agcacaacac ctgcggggc acctgcgacc gctgctgccc  1080
cggcttcaat cagcagccgt ggaagcctgc gactgccaac agtgccaacg agtgccagtc  1140
ctgtaactgc tacggccatg ccaccgactg ttactacgac cctgaggtgg accggcgccg  1200
cgccagccag agcctggatg gcacctatca gggtgggggt gtctgtatcg actgccagca  1260
ccacaccacc ggcgtcaact gtgagcgctg cctgcccggc ttctaccgct ctcccaacca  1320
ccctctcgac tcgccccacg tctgccgccg ctgcaactgc gagtccgact tcacggatgg  1380
cacctgcgag gacctgacgg tcgatgcta ctgccggccc aacttctctg gggagcggtg  1440
tgacgtgtgt gccgagggct tcacgggctt cccaagctgc tacccgacgc cctcgtcctc  1500
caatgacacc agggagcagg tgctgccagc cggccagatt gtgaattgtg actgcagcgc  1560
ggcagggacc cagggcaacg cctgccgaa ggacccaagg gtgggacgct gtctgtgcaa  1620
acccaacttc caaggcaccc attgtgagct ctgcgcgcca gggttctacg gccccggctg  1680
ccagccctgc cagtgttcca gccctggagt ggccgatgac cgctgtgacc ctgacacagg  1740
ccagtgcagg tgccgagtgg gcttcgaggg gccacatgt gatcgctgtg cccccggcta  1800
cttccacttc cctctctgcc agttgtgtgg ctgcagccct gcaggaacct tgcccgaggg  1860
ctgcgatgag gccggccgct gcctatgcca gcctgagttt gctggacctc attgtgaccg  1920
gtgccgccct ggctaccatg gtttccccaa ctgccaagca tgcacctgcg accctcgggg  1980
agccctggac cagctctgtg gggcgggagg tttgtgccgc tgccgccccg gctacacagg  2040
cactgcctgc caggaatgca gccccggctt tcacggcttc cccagctgtg tccctgcca  2100
ctgctctgct gaaggctccc tgcacgcagc ctgtgacccc ggagtgggc agtgcagctg  2160
ccggccccgt gtgacgggc tgcggtgtga cacatgtgtg cccggtgcct acaacttccc  2220
ctactgcgaa gctggctctt gccacccctgc cggtctggcc ccagtggatc ctgcccttcc  2280
```

```
tgaggcacag gttccctgta tgtgccgggc tcacgtggag gggccgagct gtgaccgctg   2340
caaacctggg ttctggggac tgagcccag caaccccgag ggctgtaccc gctgcagctg   2400
cgacctcagg ggcacactgg gtggagttgc tgagtgccag ccgggcaccg gccagtgctt   2460
ctgcaagccc cacgtgtgcg ccaggcctg cgcgtcctgc aaggatggct tctttggact   2520
ggatcaggct gactattttg gctgccgcag ctgccggtgt gacattggcg gtgcactggg   2580
ccagagctgt gaaccgagga cgggcgtctg ccggtgccgc cccaacaccc agggccccac   2640
ctgcagcgag cctgcgaggg accactacct cccggacctg caccacctgc gcctggagct   2700
ggaggaggct gccacacctg agggtcacgc cgtgcgcttt ggcttcaacc ccctcgagtt   2760
cgagaacttc agctggaggg gctacgcgca gatggcacct gtccagccca ggatcgtggc   2820
caggctgaac ctgacctccc ctgaccttttt ctggctcgtc ttccgatacg tcaaccgggg   2880
ggccatgagt gtgagcgggc gggtctctgt gcgagaggag ggcaggtcgg ccacctgcgc   2940
caactgcaca gcacagagtc agcccgtggc cttcccaccc agcacggagc ctgccttcat   3000
caccgtgccc cagaggggct tcggagagcc ctttgtgctg aaccctggca cctgggccct   3060
gcgtgtggag gccgaagggg tgctcctgga ctacgtggtt ctgctgccta gcgcatacta   3120
cgaggcggcg ctcctgcagc tgcgggtgac tgaggcctgc acataccgtc cctctgccca   3180
gcagtctggc gacaactgcc tcctctacac acacctcccc ctggatggct cccctcggc   3240 cgccgggctg gaggccctgt gtcgccagga caacagcctg ccccggccct gccccacgga   3300
gcagctcagc ccgtcgcacc cgccactgat cacctgcacg ggcagtgatg tggacgtcca   3360
gcttcaagtg gcagtgccac agccaggccg ctatgcccta gtggtggagt acgccaatga   3420
ggatgcccgc caggaggtgg gcgtggccgt gcacacccca cagcgggccc cccagcaggg   3480
gctgctctcc ctgcaccccct gcctgtacag caccctgtgc cggggcactg cccgggatac   3540
ccaggaccac ctggctgtct tccacctgga ctcggaggcc agcgtgaggc tcacagccga   3600
acaggcacgc ttcttcctgc acggggtcac tctggtgccc attgaggagt tcagcccgga   3660
gttcgtggag ccccgggtca gctgcatcag cagccacggc gcctttggcc ccaacagtgc   3720
cgcctgtctg ccctcgcgct tcccaaagcc gccccagccc atcatcctca gggactgcca   3780
ggtgatcccg ctgccgcccg gcctcccgct gacccacgcg caggatctca ctccagccat   3840
gtccccagct ggaccccgac ctcggccccc caccgctgtg gacctgatg cagagcccac   3900 cctgctgcgt gagcccagg ccaccgtggt cttcaccacc catgtgccca cgctgggccg   3960
ctatgccttc ctgctgcacg gctaccagcc agcccacccc accttccccg tggaagtcct   4020
catcaacgcc ggccgcgtgt ggcagggcca cgccaacgcc agcttctgtc cacatggcta   4080
cggctgccgc accctggtgg tgtgtgaggg ccaggcccctg ctggacgtga cccacagcga   4140
gctcactgtg accgtgcgtg tgcccaaggg ccggtggctc tggctggatt atgtactcgt   4200
ggtccctgag aacgtctaca gctttggcta cctccgggag gagcccctgg ataaatccta   4260
tgacttcatc agccactgcg cagcccaggg ctaccacatc agcccagca gctcatccct   4320 gttctgccga aacgctgctg cttccctctc cctcttctat aacaacggag cccgtccatg   4380
tggctgccac gaagtaggtg ctacaggccc acgtgtgag cccttcgggg gccagtgtcc   4440
ctgccatgcc catgtcattg gcgtgactg ctcccgctgt gccaccggat actgggcctt   4500 cccccaactgc aggccctgtg actgcggtgc ccgcctctgt gacgagctca cgggccagtg   4560
catctgcccg ccacgcacca tcccgcccga ctgcctgctg tgcagccccc agacctttgg   4620
ctgccacccc ctggtcggct gtgaggagtg taactgctca gggcccggca tccaggagct   4680
```

```
cacagaccct acctgtgaca cagacagcgg ccagtgcaag tgcagaccca acgtgactgg    4740
gcgccgctgt gatacctgct ctccgggctt ccatggctac ccccgctgcc gccctgtga    4800 ctgtcacgag gcgggcactg cgcctggcgt gtgtgacccc ctcacagggc agtgctactg    4860
taaggagaac gtgcagggcc ccaaatgtga ccagtgcagc cttgggacct tctcactgga    4920
tgctgccaac cccaaaggtt gcacccgctg cttctgcttt ggggccacgg agcgctgccg    4980
gagctcgtcc tacacccgcc aggagttcgt ggatatggag ggatgggtgc tgctgagcac    5040
tgaccggcag gtggtgcccc acgagcggca gccagggacg gagatgctcc gtgcagacct    5100
gcggcacgtg cctgaggctg tgcccgaggc tttccccgag ctgtactggc aggcccacc     5160 ctcctacctg ggggaccggg tgtcatccta cggtgggacc ctccgttatg aactgcactc    5220
agagacccag cggggagatg tctttgtccc catggagagc aggccggatg tggtgctgca    5280
gggcaaccag atgagcatca cattcctgga gccggcatac cccacgcctg ccacgttca     5340 ccgtgtgggcag ctgcagctgg tggaggggaa cttccggcat acggagacgc gcaacactgt  5400
gtcccgcgag gagctcatga tggtgctggc cagcctggag cagctgcaga tccgtgccct    5460
cttctcacag atctcctcgg ctgtcttcct gcgcagggtg gcactggagg tggccagccc    5520
agcaggccag ggggccctgg ccagcaatgt ggagctgtgc ctgtgccccg ccagctaccg    5580
gggggactca tgccaggaat gtgccccgg cttctatcgg gacgtcaaag gtctcttcct     5640
gggccgatgt gtcccttgtc agtgccatgg acactcagac cgctgcctcc ctggctctgg    5700
cgtctgtgtg gactgccagc acaacaccga aggggcccac tgtgagcgct gccaggctgg    5760
cttcgtgagc agcagggacg accccagcgc ccctgtgtc agctgcccct gccccctctc     5820
agtgccttcc aacaacttcg ccgagggctg tgtcctgcga ggcggccgca cccagtgcct    5880
ctgcaaacct ggttatgcag gtgcctcctg cgagcggtgt gcgcccggat tctttgggaa    5940
cccactggtg ctgggcagct cctgccagcc atgcgactgc agcggcaacg gtgaccccaa    6000
cttgctcttc agcgactgcg accccctgac gggcgcctgc cgtggctgcc tgcgccacac    6060
cactgggccc cgctgcgaga tctgtgcccc cggcttctac ggcaacgccc tgctgcccgg    6120
caactgcacc cggtgcgact gtaccccatg tgggacagag gcctgcgacc ccacagcgg     6180 gcactgcctg tgcaaggcgg gcgtgactgg gcggcgctgt gaccgctgcc aggagggaca    6240
ttttggtttc gatggctgcg ggggctgccg cccgtgtgct tgtggaccgg ccgccgaggg    6300
ctccgagtgc caccccagagcggacagtg ccactgccga ccagggacca tgggacccca    6360
gtgccgcgag tgtgccccctg gctactgggg gctccctgag cagggctgca ggcgctgcca    6420
gtgccctggg ggccgctgtg accctcacac gggccgctgc aactgccccc cggggctcag    6480
cggggagcgc tgcgacacct gcagccagca gcatcaggtg cctgttccag gcgggcctgt    6540
gggccacagc atccactgtg aagtgtgtga ccactgtgtg gtcctgctcc tggatgacct    6600
ggaacgggcc ggcgccctcc tccccgccat tcacgagcaa ctgcgtggca tcaatgccag    6660
ctccatggcc tgggcccgtc tgcacaggct gaacgcctcc atcgctgacc tgcagagcca    6720
gctccggagc cccctgggcc cccgccatga cacggcacag cagctggagg tgctggagca    6780
gcagagcaca agcctcgggc aggacgcacg gcggctaggc ggccaggccg tggggaccccg   6840 agaccaggcg agccaattgc tggccggcac cgaggccaca ctgggccatg cgaagacgct    6900
gttggcggca atccggggctg tggaccgcac cctgagcgag ctcatgtccc agacgggcca    6960
cctggggctg gccaatgcct cggctccatc aggtgagcag ctgctccgga cactggccga    7020
```

```
ggtggagcgg ctgctctggg agatgcgggc ccgggacctg ggggccccgc aggcagcagc      7080
tgaggctgag ttggctgcag cacagagatt gctggcccgg gtgcaggagc agctgagcag      7140
cctctgggag gagaaccagg cactggccac acaaacccgc gaccggctgg cccagcacga      7200
ggccggcctc atggacctgc gagaggcttt gaacgggca gtggacgcca cacgggaggc       7260
ccaggagctc aacagccgca accaggagcg cctggaggaa gccctgcaaa ggaagcagga      7320
gctgtcccgg gacaatgcca ccctgcaggc cactctgcat gcggctaggg acaccctggc      7380
cagcgtcttc agattgctgc acagcctgga ccaggctaag gaggagctgg agcgcctcgc      7440
cgccagcctg gatggggctc ggaccccact gctgcagagg atgcagacct tctccccggc      7500
gggcagcaag ctgcgtctag tggaggccgc cgaggcccac gcacagcagc tgggccagct      7560
ggcactcaat ctgtccagca tcatcctgga cgtcaaccag gaccgcctca cccagagggc      7620
catcgaggcc tccaacgcct acagccgcat cctgcaggcc gtgcaggctg ccgaggatgc      7680
tgctggccag gccctgcagc aggcggacca cacgtgggcg acggtggtgc ggcagggcct      7740
ggtggaccga gcccagcagc tcctggccaa cagcactgca ctagaagagg ccatgctcca      7800
ggaacagcag aggctgggcc ttgtgtgggc tgccctccag ggtgccagga cccagctccg      7860
agatgtccgg gccaagaagg accagctgga ggcgcacatc caggcggcgc aggccatgct      7920
tgccatggac acagacgaga caagcaagaa gatcgcacat gccaaggctg tggctgctga      7980
agcccaggac accgccaccc gtgtgcagtc ccagctgcag gccatgcagg agaatgtgga      8040
gcggtggcag ggccagtacg agggcctgcg gggccaggac ctgggccagg cagtgcttga      8100
cgcaggccac tcagtgtcca ccctggagaa gacgctgccc cagctgctgg ccaagctgag      8160
catcctggag aaccgtgggg tgcacaacgc cagcctggcc ctgtccgcca gcattggccg      8220
cgtgcgagag ctcattgccc aggcccgggg ggctgccagt aaggtcaagg tgcccatgaa      8280
gttcaacggg cgctcagggg tgcagctgcg caccccacgg gatcttgccg accttgctgc      8340
ctacactgcc ctcaagttct acctgcaggg cccagagcct gagcctgggc agggtaccga      8400
ggatcgcttt gtgatgtaca tgggcagccg ccaggccact ggggactaca tgggtgtgtc      8460
tctgcgtgac aagaaggtgc actgggtgta tcagctgggt gaggcgggcc ctgcagtcct      8520
aagcatcgat gaggacattg gggagcagtt cgcagctgtc agcctggaca ggactctcca      8580
gtttggccac atgtccgtca cagtggagag acagatgatc caggaaacca gggtgacac      8640
ggtggcccct gggcagagg ggctgctcaa cctgcggcca gacgacttcg tcttctacgt       8700
cgggggtac cccagtacct tcacgcccc tcccctgctt cgcttcccg gctaccgggg        8760
ctgcatcgag atggacacgc tgaatgagga ggtggtcagc ctctacaact tcgagaggac      8820
cttccagctg gacacggctg tggacaggcc ttgtgcccgc tccaagtcga ccggggaccc      8880
gtggctcacg gacggctcct acctggacgg caccggcttc gcccgcatca gcttcgacag      8940
tcagatcagc accaccaagc gcttcgagca ggagctgcgg ctcgtgtcct acagcgggt       9000
gctcttcttc ctgaagcagc agagccagtt cctgtgcttg gccgtgcaag aaggcagcct      9060
cgtgctgttg tatgacttg gggctggcct gaaaaaggcc gtcccactgc agccccacc       9120
gcccctgacc tcgccagca aggcgatcca gtgttcctg ctgggggca gccgcaagcg        9180
tgtgctggtg cgtgtggagc gggccacggt gtacagcgtg gagcaggaca atgatctgga      9240
gctggccgac gcctactacc tggggggcgt gccgcccgac cagctgcccc cgagcctgcg      9300
acggctcttc cccaccggag gctcagtccg tggctgcgtc aaaggcatca aggccctggg      9360
caagtatgtg gacctcaagc ggctgaacac gacaggcgtg agcgccggct gcaccgccga     9420
```
cctgctggtg gggcgcgcca tgactttcca tggccacggc ttccttcgcc tggcgctctc    9480
gaacgtggca ccgctcactg gcaacgtcta ctccggcttc ggcttccaca gcgcccagga    9540
cagtgccctg ctctactacc gggcgtcccc ggatgggcta tgccaggtgt ccctgcagca    9600
gggccgtgtg agcctacagc tcctgaggac tgaagtgaaa actcaagcgg cttcgccga    9660 tggtgccccc cattacgtcg ccttctacag caatgccacg ggagtctggc tgtatgtcga    9720
tgaccagctc cagcagatga agccccaccg gggaccaccc cccgagctcc agccgcagcc    9780
tgaggggccc ccgaggctcc tcctgggagg cctgcctgag tctggcacca tttacaactt    9840
cagtggctgc atcagcaacg tcttcgtgca gcggctcctg ggcccacagc gcgtatttga    9900
tctgcagcag aacctgggca gcgtcaatgt gagcacgggc tgtgcacccg ccctgcaagc    9960
ccagaccccg ggcctggggc ctagaggact gcaggccacc gcccggaagg cctcccgccg   10020
cagccgtcag cccgcccggc atcctgcctg catgctgccc ccacacctca ggaccacccg   10080
agactcctac cagtttgggg gttccctgtc cagtcacctg gagtttgtgg catcctggc    10140 ccgacatagg aactggccca gtctctccat gcacgtcctc ccgcgaagct cccgaggcct   10200
cctcctcttc actgcccgtc tgaggcccgg cagcccctcc ctggcgctct tcctgagcaa   10260
tggccacttc gttgcacaga tggaaggcct cgggactcgg ctccgcgccc agagccgcca   10320
gcgctcccgg cctggccgct ggcacaaggt ctccgtgcgc tgggagaaga accggatcct   10380
gctggtgacg gacggggccc gggcctggag ccaggagggg ccgcaccggc agcaccaggg   10440
ggcagagcac ccccagcccc acaccctctt tgtgggcggc ctcccggcca gcagccacag   10500
ctccaaactt ccggtgaccg tcgggttcag cggctgtgtg aagagactga ggctgcacgg   10560
gaggcccctg ggggccccca cacggatggc aggggtcaca ccctgcatct tgggcccct    10620 ggaggcgggc ctgttcttcc caggcagcgg gggagttatc actttagacc tcccaggagc   10680
tacactgcct gatgtgggcc tggaactgga ggtgcggccc ctgcagtca ccggactgat    10740 cttccacttg gccaggcccc ggacgccccc ctacttgcag ttgcaggtga ccgagaagca   10800
agtcctgctg cgggcggatg acggagcagg ggagttctcc acgtcagtga cccgcccctc   10860
agtgctgtgt gatggccagt ggcaccggct agcggtgatg aaaagcggga atgtgctccg   10920
gctggaggtg gacgcgcaga gcaaccacac cgtgggcccc ttgctggcgg ctgcagctgg   10980
tgccccagcc cctctgtacc tcgggggcct gcctgagccc atggccgtgc agccctggcc   11040
ccccgcctac tgcggctgca tgaggaggct ggcggtgaac cggtccccg tcgccatgac    11100 tcgctctgtg gaggtccacg gggcagtggg ggccagtggc tgcccagccg cctaggacac   11160
agccaacccc ggcccctggt caggccctg cagctgcctc acaccgcccc ttgtgctcgc    11220
ctcataggtg tctatttga ctctaagctc tacgggtgac agatcttgtt tctgaagatg    11280
gtttaagtta tagcttctta aacgaaagaa taaaatactg caaaatgttt ttatatttgg   11340
cccttccacc cattttaat tgtgagagat ttgtcaccaa tcatcactgg ttcctcctta    11400
aaaattaaaa agtaacttct gtgtaa                                        11426

<210> SEQ ID NO 6
<211> LENGTH: 7632
<212> TYPE: DNA
<213> ORGANISM: Homo sapiens

<400> SEQUENCE: 6
atgagaggga gccatcgggc cgcgccggcc ctgcggcccc gggggcggct ctggcccgtg        60

-continued

| | | |
|---|---|---|
| ctggccgtgc tggcggcggc cgccgcggcg ggctgtgccc aggcagccat ggacgagtgc | 120 | |
| acggacgagg gcgggcggcc gcagcgctgc atgcccgagt tcgtcaacgc cgccttcaac | 180 | |
| gtgactgtgg tggccaccaa cacgtgtggg actccgcccg aggaatactg tgtgcagacc | 240 | |
| ggggtgaccg gggtcaccaa gtcctgtcac ctgtgcgacg ccgggcagcc ccacctgcag | 300 | |
| cacgggcag ccttcctgac cgactacaac aaccaggccg acaccacctg gtggcaaagc | 360 | |
| cagaccatgc tggccggggt gcagtacccc agctccatca acctcacgct gcacctggga | 420 | |
| aaagcttttg acatcaccta tgtgcgtctc aagttccaca ccagccgccc ggagagcttt | 480 | |
| gccatttaca agcgcacacg ggaagacggg ccctggattc cttaccagta ctacagtggt | 540 | |
| tcctgtgaga cacctactc caaggcaaac cgcggcttca tcaggacagg aggggacgag | 600 | |
| cagcaggcct tgtgtactga tgaattcagt gacatttctc ccctcactgg gggcaacgtg | 660 | |
| gccttttcta ccctggaagg aaggcccagc gcctataact ttgacaatag ccctgtgctg | 720 | |
| caggaatggg taactgccac tgacatcaga gtaactctta atcgcctgaa cacttttgga | 780 | |
| gatgaagtgt ttaacgatcc caaagttctc aagtcctatt attatgccat ctctgattt | 840 | |
| gctgtaggtg gcagatgtaa atgtaatgga cacgcaagcg agtgtatgaa gaacgaattt | 900 | |
| gataagctgt tgtgtaattg caaacataac acatatggaa tagactgtga aaagtgtctt | 960 | |
| cctttcttca atgaccggcc gtggaggagg gcaactgcgg aaagtgccag tgaatgcctg | 1020 | |
| ccctgtgatt gcaatggtcg atcccaggaa tgctacttcg accctgaact ctatcgttcc | 1080 | |
| actggccatg ggggccactg taccaactgc caggataaca cagatggcgc ccactgtgag | 1140 | |
| aggtgccgag agaacttctt ccgccttggc aacaatgaag cctgctcttc atgccactgt | 1200 | |
| agtcctgtgg gctctctaag cacacagtgt gatagttacg gcagatgcag ctgtaagcca | 1260 | |
| ggagtgatgg gggacaaatg tgaccgttgc cagcctggat tccattctct cactgaagca | 1320 | |
| ggatgcaggc catgctcttg tgatccctct ggcagcatag atgaatgtaa tattgaaaca | 1380 | |
| ggaagatgtg tttgcaaaga caatgtcgaa ggcttcaatt gtgaaagatg caaacctgga | 1440 | |
| ttttttaatc tggaatcatc taatcctcgg ggttgcacac cctgcttctg ctttgggcat | 1500 | |
| tcttctgtct gtacaaacgc tgttggctac agtgtttatt ctatctcctc taccttcag | 1560 | |
| attgatgagg atgggtggcg tgcggaacag agagatggct ctgaagcatc tctcgagtgg | 1620 | |
| tcctctgaga ggcaagatat cgccgtgatc tcagacagct actttcctcg gtacttcatt | 1680 | |
| gctcctgcaa agttcttggg caagcaggtg ttgagttatg gtcagaacct ctccttctcc | 1740 | |
| tttcgagtgg acaggcgaga tactcgcctc tctgcagaag accttgtgct gagggagct | 1800 | |
| ggcttaagag tatctgtacc cttgatcgct cagggcaatt cctatccaag tgagaccact | 1860 | |
| gtgaagtatg tcttcaggct ccatgaagca acagattacc cttggaggcc tgctcttacc | 1920 | |
| ccttttgaat ttcagaagct cctaaacaac ttgacctcta tcaagatacg tgggacatac | 1980 | |
| agtgagagaa gtgctggata tttggatgat gtcaccctgg caagtgctcg tcctgggcct | 2040 | |
| ggagtccctg caacttgggt ggagtcctgc acctgtcctg tgggatatgg agggcagttt | 2100 | |
| tgtgagatgt gcctctcagg ttacagaaga gaaactccta atcttggacc atacagtcca | 2160 | |
| tgtgtgcttt gcgcctgcaa tggacacagc gagacctgtg atcctgagac aggtgtttgt | 2220 | |
| aactgcagag acaatacggc tggcccgcac tgtgagaagt gcagtgatgg gtactatgga | 2280 | |
| gattcaactg caggcacctc ctccgattgc caaccctgtc cgtgtcctgg aggttcaagt | 2340 | |
| tgtgctgttg ttcccaagac aaaggaggtg gtgtgcacca actgtcctac tggcaccact | 2400 | |
| ggtaagagat gtgagctctg tgatgatggc tactttggag acccctgggg tagaaacggc | 2460 | |

```
cctgtgagac tttgccgcct gtgccagtgc agtgacaaca tcgatcccaa tgcagttgga    2520
aattgcaatc gcttgacggg agaatgcctg aagtgcatct ataacactgc tggcttctat    2580
tgtgaccggt gcaaagacgg attttttgga aatcccctgg ctcccaatcc agcagacaaa    2640
tgcaaagcct gcaattgcaa tctgtatggg accatgaagc agcagagcag ctgtaacccc    2700
gtgacgggc agtgtgaatg tttgcctcac gtgactggcc aggactgtgg tgcttgtgac     2760
cctggattct acaatctgca gagtgggcaa ggctgtgaga ggtgtgactg ccatgccttg    2820
ggctccacca atgggcagtg tgacatccgc accggccagt gtgagtgcca gcccggcatc    2880
actggtcagc actgtgagcg ctgtgaggtc aaccactttg ggtttggacc tgaaggctgc    2940
aaaccctgtg actgtcatcc tgagggatct ctttcacttc agtgcaaaga tgatggtcgc    3000
tgtgaatgca gagaaggctt tgtgggaaat cgctgtgacc agtgtgaaga aaactatttc    3060
tacaatcggt cttggcctgg ctgccaggaa tgtccagctt gttaccggct ggtaaaggat    3120
aaggttgctg atcatagagt gaagctccag gaattagaga gtctcatagc aaaccttgga    3180
actggggatg agatggtgac agatcaagcc ttcgaggata gactaaagga agcagagagg    3240
gaagttatgg acctccttcg tgaggcccag gatgtcaaag atgttgacca gaatttgatg    3300
gatcgcctac agagagtgaa taacactctg tccagccaaa ttagccgttt acagaatatc    3360
cggaatacca ttgaagagac tggaaacttg gctgaacaag cgcgtgccca tgtagagaac    3420
acagagcggt tgattgaaat cgcatccaga gaacttgaga agcaaaagt cgctgctgcc     3480
aatgtgtcag tcactcagcc agaatctaca ggggacccaa acaacatgac tcttttggca    3540
gaagaggctc gaaagcttgc tgaacgtcat aaacaggaag ctgatgacat tgttcgagtg    3600
gcaaagacag ccaatgatac gtcaactgag gcatacaacc tgcttctgag gacactggca    3660
ggagaaaatc aaacagcatt tgagattgaa gagcttaata ggaagtatga acaagcgaag    3720
aacatctcac aggatctgga aaaacaagct gcccgagtac atgaggaggc caaaagggcc    3780
ggtgacaaag ctgtggagat ctatgccagc gtggctcagc tgagccctt ggactctgag     3840
acactggaga tgaagcaaa taacataaag atggaagctg agaatctgga caactgatt     3900
gaccagaaat taaagatta tgaggacctc agagaagata tgagagggaa ggaacttgaa    3960
gtcaagaacc ttctggagaa aggcaagact gaacagcaga ccgcagacca actcctagcc    4020
cgagctgatg ctgccaaggc cctcgctgaa gaagctgcaa agagggacg ggatacctta    4080
caagaagcta atgacattct caacaacctg aaagattttg ataggcgtgt gaacgataac    4140
aagacggccg cagaggaggc actaaggaag attcctgcca tcaaccagac catcactgaa    4200
gccaatgaaa agaccagaga agcccagcag gccctgggca gtgctgcggc ggatgccaca    4260
gaggccaaga caaggccca tgaggcgag aggatcgcga gcgctgtcca aaagaatgcc      4320
accagcacca aggcagaagc tgaaagaact tttgcagaag ttacagatct ggataatgag    4380
gtgaacaata tgttgaagca actgcaggaa gcagaaaaag agctaaagag aaaacaagat    4440
gacgctgacc aggacatgat gatggcaggg atggcttcac aggctgctca agaagccgag    4500
atcaatgcca gaaaagccaa aaactctgtt actagcctcc tcagcattat taatgacctc    4560
ttggagcagc tggggcagct ggatacagtg acctgaata agctaaacga gattgaaggc    4620
accctaaaca aagccaaaga tgaaatgaag gtcagcgatc ttgataggaa agtgtctgac    4680
ctggagaatg aagccaagaa gcaggaggct gccatcatgg actataaccg agatatcgag    4740
gagatcatga aggacattcg caatctggag gacatcagga agaccttacc atctggctgc    4800
```

```
ttcaacaccc cgtccattga aaagccctag tgtctttagg gctggaaggc agcatccctc    4860
tgacagggggg gcagttgtga ggccacagag tgccttgaca caaagattac atttttcaga   4920
cccccactcc tctgctgctg tccatgactg tccttttgaa ccaggaaaag tcacagagtt    4980
taaagagaag caaattaaac atcctgaatc gggaacaaag ggttttatct aataaagtgt    5040
ctcttccatt cacgttgcta ccttacccac actttccctt ctgatttgcg tgaggacgtg    5100
gcatcctacg ttactgtaca gtggcataag cacatcgtgt gagcccatgt atgctggggt    5160
agagcaagta gccctcccct gtctcatcga taccagcaga acctcctcag tctcagtact    5220
cttgtttcta tgaaggaaaa gtttggctac taacagtagc attgtgatgg ccagtatatc    5280
cagtccatgg ataaagaaaa tgcatctgca tctcctaccc ctcttccttc taagcaaaag    5340
gaaataaaca tcctgtgcca aaggtattgg tcatttagaa tgtcggtagc catccatcag    5400
tgcttttagt tattatgagt gtaggacact gagccatccg tgggtcagga tgcaattatt    5460
tataaaagtc tccaggtgaa catggctgaa gatttttcta gtatattaat aattgactag    5520
gaagatgaac tttttttcag atctttgggc agctgataat ttaaatctgg atgggcagct    5580
tgcactcacc aatagaccaa aagacatctt ttgatattct tataaatgga acttacacag    5640
aagaaatagg gatatgataa ccactaaaat tttgttttca aaatcaaact aattcttaca    5700
gctttttttat tagttagtct tggaactagt gttaagtatc tggcagagaa cagttaatcc    5760
ctaaggtctt gacaaaacag aagaaaaaca agcctcctcg tcctagtctt ttctagcaaa    5820
gggataaaac ttagatggca gcttgtactg tcagaatccc gtgtatccat ttgttcttct    5880
gttggagaga tgagacattt gacccttagc tccagttttc ttctgatgtt tccatcttcc    5940
agaatccctc aaaaaacatt gtttgccaaa tcctggtggc aaatacttgc actcagtatt    6000
tcacacagct gccaacgcta tcgagttcct gcactttgtg atttaaatcc actctaaacc    6060
ttccctctaa gtgtagaggg aagacccttta cgtggagttt cctagtgggc ttctcaactt    6120
ttgatcctca gctctgtggt tttaagacca cagtgtgaca gttccctgcc acacaccccc    6180
ttcctcctac caacccacct ttgagattca tatatagcct ttaacactat gcaactttgt    6240
actttgcgta gcagggggcgg ggtgggggga aagaaactat tatctgacac actggtgcta    6300
ttaattattt caaatttata ttttttgtgtg aatgttttgt gttttgttta tcatgattat    6360
agaataagga atttatgtaa atatacttag tcctatttct agaatgacac tctgttcact    6420
ttgctcaatt tttcctcttc actggcacaa tgtatctgaa tacctccttc cctcccttct    6480
agaattcttt ggattgtact ccaaagaatt gtgccttgtg tttgcagcat ctccattctc    6540
taaaattaat ataattgctt tcctccacac ccagccactg taaagaggta acttgggtcc    6600
tcttccattg cagtcctgat gatcctaacc tgcagcacgg tggttttaca atgttccaga   6660
gcaggaacgc caggttgaca agctatggta ggattaggaa agtttgctga agaggatctt    6720
tgacgccaca gtgggactag ccaggaatga gggagaaatg ccctttctgg caattgttgg    6780
agctggatag gtaagtttta taagggagta cattttgact gagcacttag gcatcagga     6840
acagtgctac ttactgatgg gtagactggg agaggtggtg taacttagtt cttgatgatc    6900
ccacttcctg tttccatctg cttgggatat accagagttt accacaagtg ttttgacgat    6960
atactcctga gctttcactc tgctgcttct cccaggcctc ttctactatg gcaggagatg    7020
tggcgtgctg ttgcaaagtt ttcacgtcat tgtttcctgg ctagttcatt tcattaagtg    7080
gctacatcct aacatatgca tttggtcaag gttgcagaag aggactgaag attgactgcc    7140
aagctagttt gggtgaagtt cactccagca agtctcaggc cacaatgggg tggtttggtt    7200
```

```
tggtttcctt ttaactttct ttttgttatt tgcttttctc ctccacctgt gtggtatatt    7260
ttttaagcag aattttattt tttaaaataa aaggttcttt acaagatgat accttaatta    7320
cactcccgca acacagccat tattttattg tctagctcca gttatctgta ttttatgtaa    7380
tgtaattgac aggatggctg ctgcagaatg ctggttgaca cagggattat tatactgcta    7440
tttttccctg aattttttc ctttgaattc caactgtgga cctttatat gtgccttcac     7500 tttagctgtt tgccttaatc tctacagcct tgctctccgg ggtggttaat aaaatgcaac    7560
acttggcatt tttatgtttt aagaaaaaca gtattttatt tataataaaa tctgaatatt    7620
tgtaaccctt ta                                                        7632

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
gtggtaccca caggcagagt tgac                                              24

<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8
gctctagagc tcttcagtgc ataggc                                            26
```

METHODS OF PRODUCING RPE CELLS

This application claims priority from U.S. Provisional Patent Application Ser. No. 61/732,764, filed Dec. 3, 2012, and from U.S. Provisional Patent Application Ser. No. 61/733,314, filed Dec. 4, 2012. The entireties of those provisional applications are fully incorporated by reference herein.

BACKGROUND

This application relates to cell biology, cell differentiation, cell therapy, molecular biology, proteins, recombinant human proteins, nucleic acids, and laminins.

Basal laminae (basement membranes) are sheet-like, cell-associated extracellular matrices that play a central role in cell growth, cellular differentiation, cell phenotype maintenance, tissue development, and tissue maintenance. They are present in virtually all tissues, and appear in the earliest stages of embryonic development.

Basal laminae are central to a variety of architectural and cell-interactive functions. For example:

1. They serve as architectural supports for tissues, providing adhesive substrata for cells.
2. They create perm-selective barriers between tissue compartments that impede the migration of cells and passively regulate the exchange of macromolecules. These properties are illustrated by the kidney glomerular basement membrane, which functions as an important filtration structure, creating an effective blood-tissue barrier that is not permeable to most proteins and cells.
3. Basal laminae create highly interactive surfaces that can promote cell migration and cell elongation during embryogenesis and wound repair. Following an injury, they provide a surface upon which cells regenerate to restore normal tissue function.
4. Basal laminae present information encoded in their structure to contacting cells that is important for cellular differentiation, prevention of apoptosis, and tissue maintenance. This information is communicated to the cells through various receptors that include the integrins, dystroglycan, and cell surface proteoglycans. Signaling is dependent not only on the presence of matrix ligands and corresponding receptors that interact with sufficient affinities, but also on such topographical factors as ligand density in a three-dimensional matrix "landscape", and on the ability of basal lamina components to cluster receptors. Because these matrix proteins can be long-lived, basal laminae create a "surface memory" in the basal lamina for resident and transient cells.

The basal lamina is largely composed of laminin and type IV collagen heterotrimers that in turn become organized into complex polymeric structures. Additional components include proteoglycans such as agrin and perlecan and nidogens (entactins). To date, six type IV collagen polypeptide chains and at least twelve laminin subunit chains have been identified. These chains possess shared and unique functions and are expressed with specific temporal (developmental) and spatial (tissue-site specific) patterns.

Laminins are a family of heterotrimeric glycoproteins that reside primarily in the basal lamina. They function via binding interactions with neighboring cell receptors on the one side, and by binding to other laminin molecules or other matrix proteins such as collagens, nidogens or proteoglycans. The laminin molecules are also important signaling molecules that can strongly influence cellular behavior and function. Laminins are important in both maintaining cell/tissue phenotype, as well as in promoting cell growth and differentiation in tissue repair and development.

Laminins are large, multi-domain proteins, with a common structural organization. The laminin molecule integrates various matrix and cell interactive functions into one molecule.

A laminin protein molecule comprises one α-chain subunit, one β-chain subunit, and one γ-chain subunit, all joined together in a trimer through a coiled-coil domain. FIG. 1 depicts the resulting structure of the laminin molecule. The twelve known laminin subunit chains can form at least 15 trimeric laminin types in native tissues. Within the trimeric laminin structures are identifiable domains that possess binding activity towards other laminin and basal lamina molecules, and membrane-bound receptors. FIG. 2 shows the three laminin chain subunits separately. For example, domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

There exist five different alpha chains, three beta chains and three gamma chains that in human tissues have been found in at least fifteen different combinations. These molecules are termed laminin-1 to laminin-15 based on their historical discovery, but an alternative nomenclature describes the isoforms based on their chain composition, e.g. laminin-111 (laminin-1) that contains alpha-1, beta-1 and gamma-1 chains. Four structurally defined family groups of laminins have been identified. The first group of five identified laminin molecules all share the β1 and β1 chains, and vary by their α-chain composition (α1 to α5 chain). The second group of five identified laminin molecules, including laminin-521, all share the β2 and α1 chain, and again vary by their α-chain composition. The third group of identified laminin molecules has one identified member, laminin-332, with a chain composition of α3β3γ2. The fourth group of identified laminin molecules has one identified member, laminin-213, with the newly identified γ3 chain (α2β1γ3).

Human embryonic stem (hES) cells hold promise for the development of regenerative medicine for a variety of diseases, such as spinal cord and cardiac injuries, type I diabetes and neurodegenerative disorders like Parkinson's disease. A stem cell is an undifferentiated cell from which specialized cells are subsequently derived. Embryonic stem cells possess extensive self-renewal capacity and pluripotency with the potential to differentiate into cells of all three germ layers. They are useful for therapeutic purposes and may provide unlimited sources of cells for tissue replacement therapies, drug screening, functional genomics and proteomics.

One of the main problems with large-scale propagation of hES cells is that they poorly survive replating after dissociation into single cell suspension. This, in turn, makes passaging tedious and large-scale automated expansions impossible. However, hES cells released into single cell suspension using trypsin treatment in the presence of a rho-kinase (ROCK) inhibitor[10] or blebbistatin[11] can be plated and expanded from single clones, but the molecules are not components of the natural stem cell niche, and they affect the actin cytoskeleton and thus can cause cell damage. Therefore, the use of the ROCK inhibitor may not be a preferred solution for long-term expansion of hES cells aimed for cell therapy purposes.

For the purposes of regenerative medicine, there is a desire to develop methods that allow derivation and long-term cultures of pluripotent stem cells under chemically defined, xeno-free, pathogen-free, and stable batch-to-batch conditions. Moreover, such methods should allow fast and economically efficient scale-up to acquire large quantities of pluripotent hES/hiPS cells in a short period of time. Preferably, the methods should also allow clonal survival of human ES cells in media containing no synthetic inhibitor of apoptosis, that could facilitate scientific and clinical applications involving cell sorting or gene knock-out in the cells.

BRIEF DESCRIPTION

The present disclosure provides methods for culturing stem cells to obtain retinal pigment epethilum (RPE) cells.

Disclosed in various embodiments herein are methods of obtaining retinal pigment epithelium (RPE) cells, comprising: culturing one or more stem cells on a substrate comprising a laminin, wherein the laminin is an intact protein or a protein fragment; exposing the stem cells to a first cell culture medium that contains a growth factor, the first cell culture medium being completely chemically defined and xeno-free; after a first time period, removing the first cell culture medium and exposing the stem cells to a second cell culture medium that does not contain the growth factor, the second cell culture medium being completely chemically defined and xeno-free; and periodically changing the second cell culture medium to obtain the RPE cells.

The laminin can be laminin-521 or laminin-511. The laminin may be an effective recombinant laminin.

In some embodiments, the substrate further comprises a cadherin. The cadherin may be e-cadherin. The weight ratio of the laminin to the cadherin can be from about 5:1 to about 15:1. Sometimes, the laminin is laminin-521 and the cadherin is e-cadherin. The weight ratio of laminin-521 to e-cadherin may be from about 5:1 to about 15:1.

The first cell culture medium can be TeSR2 medium or Nutristem medium. The first cell culture medium can contain basic fibroblast growth factor (FGF2) in an amount of greater than zero to 3.9 ng/ml.

The second cell culture medium can be TeSR2 medium or Nutristem medium, the second cell culture medium having no FGF2.

The substrate, the first cell culture medium, and the second cell culture medium do not contain any substances of animal origin.

The first time period may be about one week.

The periodic changing of the second cell culture medium may occur every week, with the RPE cells being obtained after a total of about eight weeks.

Also disclosed herein in different embodiments are methods of treating a patient having macular degeneration, comprising: injecting retinal pigment epithelium (RPE) cells into an eye of the patient; wherein the RPE cells have been obtained under completely chemically defined and xeno-free conditions. The RPE cells may be obtained according to the methods described above.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

In FIG. 4, the cells were cultured without ROCK inhibitor. In FIG. 5, the cells were cultured with ROCK inhibitor Y-27632.

DETAILED DESCRIPTION

Figure 1:
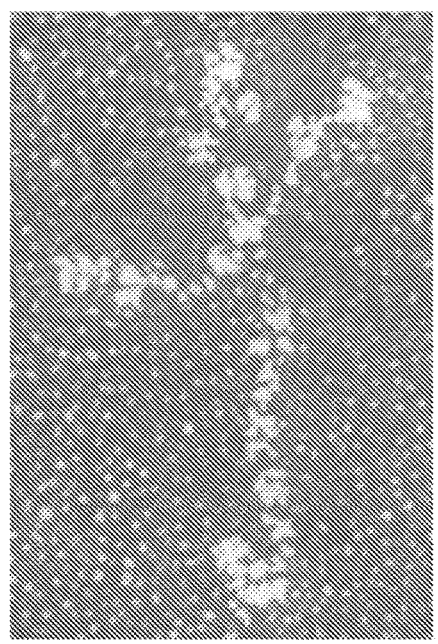
FIG. 1 is a rotary shadowing electron microscope picture of a recombinant laminin molecule.
Figure 2:
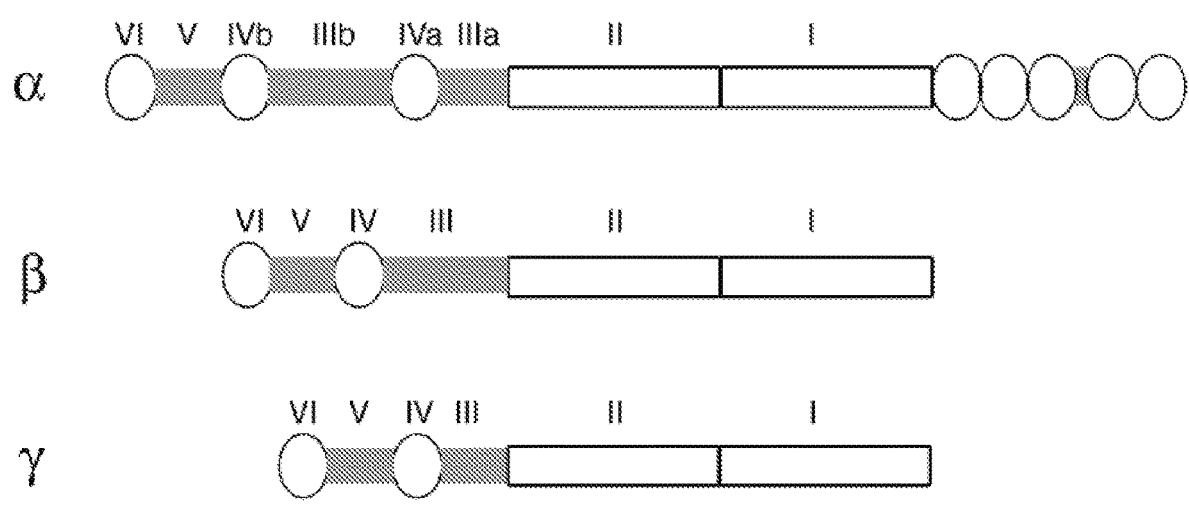
FIG. 2 shows the structural motifs of laminin α, β, and γ chains. The N-terminal, internal, and C-terminal globular domains are depicted as white ovals. The coiled-coil forming domains (I and II) are shown as white rectangles. The rod-like structures (domains V, IIIb, and IIIa) are depicted as grey rectangles.

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

All publications, patents, and patent applications discussed herein are hereby incorporated by reference in their entirety.

Unless otherwise stated, the techniques utilized in this application may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, Second Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), or the Ambion 1998 Catalog (Ambion, Austin, Tex.).

As used herein, the term "isolated nucleic acid sequence" refers to a nucleic acid sequence that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). The "isolated" sequence may, however, be linked to other nucleotide sequences that do not naturally flank the recited sequence, such as a heterologous promoter sequence, or other vector sequences. It is not necessary for the isolated nucleic acid sequence to be free of other cellular material to be considered "isolated", as a nucleic acid sequence according to the disclosure may be part of an expression vector that is used to transfect host cells (see below).

The present disclosure provides recombinant expression vectors comprising a full length laminin β2 chain nucleic acid sequence (SEQ ID NO: 4) of the human laminin β2 chain. In some embodiments, the expression vectors comprise a nucleic acid encoded by SEQ ID NO: 4, operatively linked to a heterologous promoter (i.e. is not the naturally occurring promoter for the given β2 laminin chain). A promoter and a laminin β2 chain nucleic acid sequence are "operatively linked" when the promoter is capable of driving expression of the laminin β2 chain DNA into RNA.

As used herein, the term "vector" refers to a nucleic acid molecule capable of transporting another nucleic acid to which it has been linked. One type of vector is a "plasmid", which refers to a circular double stranded DNA into which additional DNA segments may be cloned. Another type of vector is a viral vector, wherein additional DNA segments may be cloned into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors), are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In the present disclosure, the expression of the laminin polypeptide sequence is directed by the promoter sequences of the disclosure, by operatively linking the promoter sequences of the disclosure to the gene to be expressed. In general, expression vectors of utility in recombinant DNA techniques are often in the form of plasmids. In the present specification, "plasmid" and "vector" may be used interchangeably, as the plasmid is the most commonly used form of vector. However, the disclosure is intended to include other forms of expression vectors, such as viral vectors (e.g., replication defective retroviruses, adenoviruses and adeno-associated viruses), which serve equivalent functions.

The vector may also contain additional sequences, such as a polylinker for subcloning of additional nucleic acid sequences, or a polyadenylation signal to effect proper polyadenylation of the transcript. The nature of the polyadenylation signal is not believed to be crucial to the successful practice of the methods of the disclosure, and any such sequence may be employed, including but not limited to the SV40 and bovine growth hormone poly-A sites. Also contemplated as an element of the vector is a termination sequence, which can serve to enhance message levels and to minimize readthrough from the construct into other sequences. Additionally, expression vectors typically have selectable markers, often in the form of antibiotic resistance genes, that permit selection of cells that carry these vectors.

In further embodiments, the present disclosure provides host cells transfected with the laminin β2 chain-expressing recombinant expression vectors disclosed herein. As used herein, the term "host cell" is intended to refer to a cell into which a nucleic acid of the present disclosure, such as a recombinant expression vector, has been introduced. Such cells may be prokaryotic, which can be used, for example, to rapidly produce a large amount of the expression vectors of the disclosure, or may be eukaryotic, for functional studies.

The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The host cells can be transiently or stably transfected with one or more of the expression vectors of the disclosure. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2.sup.nd Ed. (R. I. Freshney. 1987. Liss, Inc. New York, N.Y.).

In another aspect, the present disclosure provides an isolated full length human laminin β2 chain polypeptide consisting of the amino acid sequence of SEQ ID NO: 2.

As used herein, an "isolated polypeptide" refers to a polypeptide that is substantially free of other proteins, including other laminin chains, and gel agents, such as polyacrylamide and agarose. In preferred embodiments, the isolated laminin polypeptide is free of detectable contaminating laminin chains. Thus, the protein can either be isolated from natural sources, or recombinant protein can be isolated from the transfected host cells disclosed above.

In another aspect, the present disclosure provides isolated laminin-521. As used herein, the term "laminin-521" refers to the protein formed by joining α5, β2 and γ1 chains together. The term should be construed as encompassing both recombinant laminin-521 and heterotrimeric laminin-521 from naturally occurring sources. In preferred embodiments, the laminin-521 comprises recombinant laminin-521 (or "r-laminin-521"). The term "recombinant" indicates that the protein is artificially produced in cells that do not normally express such proteins.

As used herein, the term "r-laminin-521" refers to recombinant heterotrimeric laminin-521, expressed by a host cell that has been transfected with one or more expression vectors comprising at least one nucleic acid sequence encoding a laminin-521 chain selected from the α5, β2 and γ1 chains, or processed or secreted forms thereof. Such r-laminin-521 can thus comprise α5, β2, and γ1 sequences from a single organism, or from different organisms. Various laminin-521 chain DNA sequences are known in the art, and the use of any such sequence to prepare the r-laminin-521 of the disclosure is contemplated. (See, for example, Pouliot, N. et al., Experimental Cell Research 261(2):360-71, (2000); Kikkawa, Y. et al., Journal of Cell Science 113 (Pt 5):869-76, (2000); Church, H J. et al., Biochemical Journal 332 (Pt 2):491-8, (1998); Sorokin, L M. et al., Developmental Biology 189(2):285-300, (1997); Miner, J H. et al., Journal of Biological Chemistry 270(48):28523-6, (1995); Sorokin, L. et al., European Journal of Biochemistry 223(2):603-10, (1994)). In preferred embodiments, the r-laminin-521 is formed from recombinant human α5, β2, and γ1 polypeptide chains.

The disclosure encompasses those laminin molecules wherein only one or two chains that make up the recombinant heterotrimeric laminin-521 are encoded by endogenous laminin-521 chains. In preferred embodiments, each of the α5, β2, and γ1 polypeptide chains are expressed recombinantly.

The laminin-521 is an intact protein. The term "intact" refers to the protein being composed of all of the domains of the α-chain, β-chain, and γ-chain, with the three chains being joined together to form the heterotrimeric structure. The protein is not broken down into separate chains, fragments, or functional domains. The term "chain" refers to the entirety of the alpha, beta, or gamma chain of the laminin protein. The term "fragment" refers to any protein fragment which contains one, two, or three functional domains that possesses binding activity to another molecule or receptor. However, a chain should not be considered a fragment because each chain possesses more than three such domains. Similarly, an intact laminin protein should not be considered a fragment. Examples of functional domains include Domains I, II, III, IV, V, VI, and the G domain.

Laminin-521 is a secreted protein, which is capable of being directed to the endoplasmic reticulum (ER), secretory vesicles, and the extracellular space as a result of a signal sequence. If the secreted protein is released into the extracellular space, the secreted protein can undergo extracellular processing to produce a "mature" protein. Such processing events can be variable, and thus may yield different versions of the final "mature protein". For example, the lengths of the α5, β2, and γ1 chains may vary between proteins. However, the final mature protein still has the same functionality, even though the chain lengths vary. The isolated laminin-521 of the present disclosure includes heterotrimers comprising both the full length polypeptide chains and any such naturally processed laminin-521 polypeptide chains.

As used herein, a laminin-521 polypeptide chain refers to a polypeptide chain according to one or more of the following:

(a) a polypeptide chain that comprises a polypeptide structure selected from the group consisting of: R1-R2-R3, R1-R2-R4, R3, R4, R1-R3, R1-R4, R2-R3, and R2-R4, wherein R1 is an amino terminal methionine; R2 is a signal sequence that is capable of directing secretion of the polypeptide, wherein the signal sequence may be the natural signal sequence for the particular laminin chain, that of another secreted protein, or an artificial sequence; R3 is a secreted laminin chain selected from the group consisting of a α5 chain, a β2 chain, and a γ1 chain; and R4 is a secreted α5, β2, or γ1 laminin chain that further comprises an epitope tag (such as those described below), which can be placed at any position within the laminin chain amino acid sequence; or (b) a polypeptide chain that is encoded by a polynucleotide that hybridizes under high or low stringency conditions to the coding regions, or portions thereof, of one or more of the recombinant laminin-521 chain DNA sequences disclosed herein (SEQ ID NO: 4, SEQ ID NO: 5, SEQ ID NO: 6), or complementary sequences thereof; or (c) a polypeptide chain that has at least 70% identity to one or more of the disclosed laminin-521 polypeptide chain amino acid sequences (SEQ ID NO: 1, SEQ ID NO: 2, SEQ ID NO: 3), preferably at least 80% identity, and most preferably at least about 90% identity.

"Stringency of hybridization" is used herein to refer to washing conditions under which nucleic acid hybrids are stable. The disclosure also includes nucleic acids that hybridize under high stringency conditions (as defined herein) to all or a portion of the coding sequences of the laminin chain polynucleotides disclosed herein, or their complements. The hybridizing portion of the hybridizing nucleic acids is typically at least 50 nucleotides in length. As known to those of ordinary skill in the art, the stability of hybrids is reflected in the melting temperature ($T_M$) of the hybrids. $T_M$ decreases approximately 1-1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. As used herein, high stringency refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are laminin-521-encoding nucleic acid sequences that hybridize to the polynucleotides of the present disclosure at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As used herein, "percent identity" of two amino acids or of two nucleic acids is determined using the algorithm of Karlin and Altschul (Proc. Natl. Acad. Sci. USA 87:2264.2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score 100, wordlength=12, to determine nucleotide sequences identity to the nucleic acid molecules of the disclosure. BLAST protein searches are performed with the XBLAST program, score=50, wordlength=3, to determine an amino acid sequence identity to a polypeptide of the disclosure. To obtain gapped alignments for comparison purposes, Gapped BLAST is utilized as described in Altschul et al. (Nucleic Acids. Res. 25:3389-3402, 1997). When utilizing BLAST and Gapped BLAST programs, the default parameters of the respective programs (e.g., XBLAST and NBLAST) are used.

Further embodiments of the present disclosure include polynucleotides encoding laminin-521 chain polypeptides having at least 70% identity, preferably at least 80% identity, and most preferably at least 90% identity to one or more of the polypeptide sequences contained in SEQ ID NO: 4, SEQ ID NO: 5, and SEQ ID NO: 6.

As used herein, "α5 polynucleotide" refers to polynucleotides encoding a laminin α5 chain. Such polynucleotides can be characterized by one or more of the following: (a) polynucleotides that encode polypeptides which share at least 70% identity, preferably 80% identity, and most preferably at least 90% identity with a sequence selected of SEQ ID NO: 5; (b) polynucleotides that hybridize under low or high stringency conditions to the coding sequence of SEQ ID NO: 5 or complementary sequences thereof; or (c) polynucleotides encoding a laminin α5 chain polypeptide with a general structure selected from the group consisting of R1-R2-R3, R1-R2-R4, R3, R4, R1-R3, R1-R4, R2-R3, and R2-R4, wherein R1 and R2 are as described above, R3 is a secreted α5 chain, and R4 is a secreted α5 chain that comprises an epitope tag.

As used herein, "β2 polynucleotides" refers to polynucleotides encoding a β2 laminin chain of the same name. Such polynucleotides can be characterized by one or more of the following: (a) polynucleotides that encode polypeptides which share at least 70% identity, preferably at least 80%, and most preferably at least 90% identity with the sequence of SEQ ID NO: 4; (b) polynucleotides that hybridize under low or high stringency conditions to the coding sequences of SEQ ID NO: 4, or complementary sequences thereof; or (c) polynucleotides encoding a polypeptide with a general structure selected from R1-R2-R3, R1-R2-R4, R3, R4, R1-R3, R1-R4, R2-R3, and R2-R4, wherein R1 and R2 are as described above, R3 is a secreted β2 chain, and R4 is a secreted β2 chain that comprises an epitope tag.

As used herein, "γ1 polynucleotides" refers to polynucleotides encoding a γ1 laminin chain of the same name. Such polynucleotides can be characterized by one or more of the following: (a) polynucleotides that encode polypeptides which share at least 70% identity, preferably at least 80%, and most preferably at least 90% identity with the sequence of SEQ ID NO: 6; (b) polynucleotides that hybridize under low or high stringency conditions to the coding sequence of SEQ ID NO: 6 or complementary sequences thereof; or (c) polynucleotides that encode a polypeptide with a general structure selected from R1-R2-R3, R1-R2-R4, R3, R4, R1-R3, R1-R4, R2-R3, and R2-R4, wherein R1 and R2 are as described above, R3 is a secreted γ1 chain, and R4 is a secreted γ1 chain that comprises an epitope tag.

As used herein, the term "epitope tag" refers to a polypeptide sequence that is expressed as part of a chimeric protein, where the epitope tag serves as a recognition site for binding of antibodies generated against the epitope tag, or for binding of other molecules that can be used for affinity purification of sequences containing the tag.

In preferred embodiments, cDNAs encoding the laminin γ5, β2 and γ1 chains, or fragments thereof, are subcloned into an expression vector. Alternatively, laminin α5, β2 and/or γ1 gene sequences, including one or more introns, can be used for subcloning into an expression vector.

In other aspects, the present disclosure provides laminin-521 expressing-cells that have been transfected with an expression vector containing promoter sequences that are operatively linked to nucleic acid sequences encoding at least one polypeptide sequence comprising a sequence selected from the group consisting of the α5, β2 and γ1 chains of laminin-521, wherein the transfected cells secrete heterotrimeric laminin-521 containing the recombinant laminin chain. In preferred embodiments, the cells are systematically transfected with recombinant expression vectors containing promoter sequences that are operatively linked to nucleic acid sequences encoding polypeptide sequences comprising the α5, β2 and γ1 chains of laminin-521, which are even more preferably all human chains. After the multiple transfections, the cells express recombinant laminin-521 chains, which form the heterotrimeric r-laminin-521.

Transfection of the expression vectors into eukaryotic cells can be accomplished via any technique known in the art, including but not limited to calcium phosphate co-precipitation, electroporation, or liposome mediated-, DEAE dextran mediated-, polycationic mediated-, or viral mediated transfection. Transfection of bacterial cells can be done by standard methods.

In preferred embodiments, the cells are stably transfected. Methods for stable transfection and selection of appropriate transfected cells are known in the art. In other preferred embodiments, a CMV promoter driven expression vector is used in a human kidney embryonic 293 cell line.

Any cell capable of expressing and secreting the r-laminin-521 can be used. Preferably, eukaryotic cells are used, and most preferably mammalian cells are used, including but not limited to kidney and epithelial cell lines. The promoter sequence used to drive expression of the individual chains or r-laminin-521 may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). Carbohydrate and disulfide post-translational modifications are believed to be required for laminin-521 protein folding and function. This makes the use of eukaryotic cells preferable for producing functional r-laminin-521, although other systems are useful for obtaining, for example, antigens for antibody production. In most preferred embodiments, the mammalian cells do not express the laminin β2 chain endogenously. In other preferred embodiments, the cells do not express all of the laminin-521 chains endogenously.

The protein may comprise additional sequences useful for promoting purification of the protein, such as epitope tags and transport signals. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals). Examples of such transport signals include, but are not limited to, export signals, secretory signals, nuclear localization signals, and plasma membrane localization signals.

In some embodiments, at least one of the laminin chain polypeptide sequences, or fragments thereof, is operatively linked to a nucleic acid sequence encoding an "epitope tag", so that at least one of the chains is expressed as a fusion protein with an expressed epitope tag. The epitope tag may be expressed as the amino terminus, the carboxy terminus, or internal to any of the polypeptide chains comprising r-laminin-521, so long as the resulting r-laminin-521 remains functional.

In other embodiments, one of the r-laminin-521 chains is expressed as a fusion protein with a first epitope tag, and at least one other r-laminin chain is expressed as a fusion protein with a second different epitope tag. This permits multiple rounds of purification to be carried out. Alternatively, the same epitope tag can be used to create fusion proteins with more than one of the r-laminin chains.

In further embodiments, the epitope tag can be engineered to be cleavable from the r-laminin-521 chain(s). Alternatively, no epitope tag is fused to any of the r-laminin-521 chains, and the r-laminin-521 is isolated by standard techniques, including but not limited to affinity chromatography using laminin-521 specific antibodies or other laminin-521 binding molecules.

Media from cells transfected with a single laminin chain are initially analyzed on Western blots using laminin chain-specific antibodies. The expression of single laminin chains following transfection is generally intracellular. Clones showing reactivity against individual transfected chain(s) are verified by any appropriate method, such as PCR, reverse transcription-PCR, or nucleic acid hybridization, to confirm incorporation of the transfected gene. Preferably, analysis of genomic DNA preparations from such clones is done by PCR using laminin chain-specific primer pairs. Media from transfected clones producing all three chains are further analyzed for r-laminin-521 secretion and/or activity, by any appropriate method, including Western blot analysis and cell binding assays.

In preferred embodiments, purification of r-laminin-521 is accomplished by passing media from the transfected cells through an antibody affinity column. In some embodiments, antibodies against a peptide epitope expressed on at least one of the recombinant chains are attached to an affinity column, and bind the r-laminin-521 that has been secreted into the media. The r-laminin-521 is removed from the column by passing excess peptide over the column. Eluted fractions are analyzed by any appropriate method, including gel electrophoresis and Western blot analysis. In further embodiments, the peptide epitope can be cleaved after purification. In other embodiments, two or three separate r-laminin chains are expressed as fusion proteins, each with a different epitope tag, permitting two or three rounds of purification and a doubly or triply isolated r-laminin-521. The epitope tag can be engineered so as to be cleavable from the r-laminin-521 chain(s) after purification. Alternatively, no epitope tag is fused to any of the r-laminin-521 chains, and the r-laminin-521 is isolated by standard techniques, including but not limited to affinity chromatography using laminin-521 specific antibodies or other laminin-521 binding molecules.

In other embodiments, purification of r-laminin-521 is accomplished by passing media from the transfected cells through a gel-filtration chromatography column. Eluted fractions are analyzed by any appropriate method, including gel electrophoresis and Western blot analysis. Fractions containing r-laminin-521 are collected and purity of the specimen is evaluated by any appropriate method, including gel electrophoresis and Western blot analysis. In some embodiments, the protein solution can be passed through a gel-filtration chromatography column again to gain higher purity of the protein. In some embodiments, to achieve higher purity of r-laminin-521 solution, the media or r-laminin-521 solution from the previous purification steps can be passed through an ion-exchange column. Eluted fractions are analyzed by any appropriate method, including gel electrophoresis and Western blot analysis. Fractions containing r-laminin-521 are collected and purity of the specimen is evaluated by any appropriate method, including mentioned above.

The laminin-521 polypeptide chains of the present disclosure also include (i) substitutions with one or more of the non-conserved amino acid residues, where the substituted amino acid residues may or may not be one encoded by the genetic code, or (ii) substitution with one or more amino acid residues having substituent groups, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

In particular embodiments, the isolated laminin-521 comprises three chains. The first chain comprises a polypeptide with at least 80% identity to a polypeptide sequence of SEQ ID NO: 1 (i.e. the α5 laminin chain). The second chain comprises a polypeptide with at least 70% identity to a polypeptide sequence of SEQ ID NO: 2 (i.e. the β2 laminin chain). The third chain comprises a polypeptide with at least 70% identity to a polypeptide sequence of SEQ ID NO: 3 (i.e. the γ1 laminin chain). These first, second, and third chains are assembled into recombinant laminin-521.

In more specific embodiments, the polypeptide of the first chain has at least 80% identity to the polypeptide sequence of SEQ ID NO: 1, the polypeptide of the second chain has at least 80% identity to the polypeptide sequence of SEQ ID NO: 2, and the polypeptide of the third chain has at least 80% identity to the polypeptide sequence of SEQ ID NO: 3.

In more specific embodiments, the polypeptide of the first chain has at least 90% identity to the polypeptide sequence of SEQ ID NO: 1, the polypeptide of the second chain has at least 90% identity to the polypeptide sequence of SEQ ID NO: 2, and the polypeptide of the third chain has at least 90% identity to the polypeptide sequence of SEQ ID NO: 3.

In particular embodiments, the first chain comprises the polypeptide sequence of SEQ ID NO: 1, the second chain comprises the polypeptide sequence of SEQ ID NO: 2, and the third chain comprises the polypeptide sequence of SEQ ID NO: 3.

In particular embodiments, the first chain is the polypeptide sequence of SEQ ID NO: 1, the second chain is the polypeptide sequence of SEQ ID NO: 2, and the third chain is the polypeptide sequence of SEQ ID NO: 3.

In other aspects, the present disclosure provides a new material, isolated laminin-521, which permits human embryonic stem cell survival after dissociation into single cell suspension. The stem cells were dissociated into single cell suspension by Trypsin-EDTA treatment, pelleted by centrifugation, resuspended into O3 medium, filtered through a 40 μm sieve, and plated at a density of 30 Kcells/cm$^2$ on cell culture dishes precoated by either isolated laminin-521, laminin-511, or Matrigel. After one day in culture, the cells plated on Matrigel died, as is known in the art. The human embryonic stem cells plated on laminin-521 and in most cases on laminin-511 survived and started to proliferate, forming small colonies of pluripotent cells.

In further aspects, the present disclosure provides a method to expand human embryonic stem cells in pluripotent state. It has been shown that human embryonic stem cells plated in single cell suspension on laminin-521 survived and proliferated at a higher rate than that of classical methods known in the art. After 3 passages (1 month) the cells passaged in a single cell suspension underwent the same number of cell divisions as that of cell cultures passaged in pieces on Matrigel after 20 passages (3 months). Therefore, the new method was advantageous in terms of time and labor, which may provide significant economical profits.

Laminin-521 is normally expressed and secreted by human pluripotent embryonic stem cells and can also be found in the kidneys, neuromuscular junctions, lungs, and placenta.

The availability of pure laminin-521 would enable studies of the effects of the protein on cellular differentiation and maintenance of cellular phenotypes. Thus, numerous research and therapeutic purposes including, but not limited to, treating injuries to tissues, promoting cell attachment, expansion and migration, ex vivo cell therapy, improving the biocompatibility of medical devices, and preparing improved cell culture devices and media, would be furthered if pure intact isolated laminin-521 were available. Also, the effects of pure laminin-521 on stem cells would be important to study as this protein is expressed in the early mammalian embryo.

Thus, there is a need in the art for isolated laminin-521 for research and therapeutic purposes, and methods for making isolated laminin-521. Laminin-521 can serve as a matrix for long-term self-renewal and fast multiplication of dissociated human ES and induced pluripotent stem (iPS) cells under completely chemically defined, feeder-free, and animal-protein-free (xeno-free) conditions. A LN-521 based system is easy to use and easy to automate, and allows fast scale-up of human ES/iPS cultures.

The present disclosure also relates to a cell culture medium that can be used to provide nutrition to cells, particularly stem cells. In this regard, stem cells typically require two things to be cultured: (1) a substrate or coating that provides a structural support for the stem cell; and (2) a cell culture medium to provide nutrition to the stem cell.

The substrate or coating (1) is generally placed on, for example, a petri dish or some other container.

As used herein, the term "self-renewal" refers to the ability of the stem cell to go through numerous cycles of cell division and remain undifferentiated (i.e. pluripotent). Pluripotency itself refers to the ability of the stem cell to differentiate into any cell type. The term "proliferation" refers to the ability of the stem cell to divide. Survival refers to the ability of the stem cell to live, whether differentiated or undifferentiated, and does not require the stem cell to maintain its ability to divide or to differentiate.

The cell culture medium of the present disclosure is particularly suitable for being used with a substrate that contains laminin-521 and/or laminin-511. These laminins activate α6β1 integrins, which in turn leads to activation of the PI3K/Akt pathway. This increases the pluripotency, self-renewal, and/or proliferation of the stem cells. It is contemplated that the substrate may consist of laminin-521 or laminin-511, either intact, as separate chains, or as fragments thereof. Recombinant laminin-521 and recombinant laminin-511 are commercially available. Many different molecules can activate the PI3K/Akt pathway, though with different efficiencies. For example, TGF beta 1 and bFGF activate this pathway. The use of laminin-521 and/or laminin-511 allows the quantity of such molecules to be reduced in the cell culture medium. Laminin-521 conveys the highest dose of signal via α6β1 integrin, activating the PI3K/Akt pathway. The use of laminin-521 allows for single-cell suspension passaging without the addition of cell-detrimental rho-kinase (ROCK) inhibitor to increase cell survival after single-cell enzymatic dissociation. Previously, single-cell enzymatic passage of human ES cells without using artificial apoptosis inhibitors was impossible. The simplicity of the passaging procedure means the experimental variance is reduced and allows the process to be automated for high-throughput cell culture and results without the extensive training and costs of cell culture staff. In addition, human ES and iPS cells plated on laminin-521 or laminin-511 grow as a monolayer, which makes the culture homogeneous since cells are equally exposed to the matrix and the cell culture medium. Such human ES cell cultures, grown in a chemically defined, xeno-free environment on laminin-521, passaged as single cells in the absence of ROCK inhibitor expand continuously for months at an even better growth rate compared to cells grown on Matrigel passaged as clumps. These pluripotent long-term expanded cells homogeneously express Oct4 and remain karyotypically normal. Thus, one can obtain human ES and iPS cells with sustained survival and proliferation capacity.

The average contact area and spreading homogeneity is much larger for cells cultured on laminin-511 compared to other available substrata. Human ES cells grown on laminin-511 over 3 months maintain pluripotency and can generate teratomas after engraftment into SCID mice. Laminin-511 also supports the self-renewal of mouse ES cells for over 5 months without the presence of LIF or feeder cells, when other known matrices are unable to do so for longer than a couple of weeks.

The cell culture substrate also comprises a cadherin. Cadherins are a class of type-1 transmembrane proteins that play important roles in cell adhesion, ensuring that cells within tissues are bound together. They are dependent on calcium ($Ca^{2+}$) ions to function. Cadherins are also known as desmogleins and desmocollins. Structurally, cadherins contain extracellular $Ca^{2+}$-binding domains. In particular embodiments, the cadherin used in the cell culture substrate is epithelial cadherin or e-cadherin.

The weight ratio of the laminin to the cadherin may be from about 5:1 to about 15:1, or from about 5:1 to about 10:1. In particular embodiments, the cell culture substrate consists of the laminin and the cadherin. In other specific embodiments, the laminin is laminin-521 and the cadherin is e-cadherin.

The stem cells to be grown with this cell culture medium can be induced pluripotent stem cells, embryonic stem cells, adult stem cells, fetal stem cells, amniotic stem cells, and generally any pluripotent stem cell.

Typically, cell culture media include a large number and a large amount of various growth factors and cytokines to inhibit differentiation and improve proliferation. One advantage of the cell culture medium of the present disclosure is that it does not contain as many growth factors or cytokines, or such high amounts.

Most generally, the cell culture medium of the present disclosure requires lower amounts of basic fibroblast growth factor (bFGF) than typically used. It is contemplated that the cell culture medium may comprise from greater than zero to 3.9 nanograms per milliliter (ng/mL) of bFGF. The bFGF is human bFGF so that the cell culture medium is totally human and defined. In some more specific embodiments, the cell culture medium may comprise 3.5 or lower ng/mL of bFGF. In other embodiments, the cell culture medium may comprise from 0.5 to 3.5 ng/mL of bFGF. In some embodiments, the cell culture medium may have zero bFGF, i.e. no bFGF is present.

Generally, the cell culture medium includes a liquid phase in which at least one inorganic salt, at least one trace mineral, at least one energy substrate, at least one lipid, at least one amino acid, at least one vitamin, and at least one growth factor (besides bFGF) are dissolved. Table 1 below includes a list of various such ingredients which may be present in the cell culture medium of the present disclosure, and the minimum and maximum concentrations if the ingredient is present. The values are presented in scientific notation. For example, "4.1E−01" should be interpreted as $4.1 \times 10^{-01}$.

TABLE 1

| Ingredient | molar mass (g/mol) | Min. Conc. (mM) | Max. Conc. (mM) | Min. Conc. (ng/mL) | Max. Conc. (ng/mL) |
|---|---|---|---|---|---|
| INORGANIC SALTS | | | | | |
| Calcium chloride (Anhydrous) | 110.98 | 4.1E−01 | 1.6E+00 | 4.6E+04 | 1.8E+05 |
| HEPES | 238.3 | 5.9E+00 | 1.8E+01 | 1.4E+06 | 4.2E+06 |
| Lithium Chloride (LiCl) | 42.39 | 4.9E−01 | 1.5E+00 | 2.1E+04 | 6.2E+04 |
| Magnesium chloride (Anhydrous) | 95.21 | 1.2E−01 | 3.6E−01 | 1.1E+04 | 3.4E+04 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| Magnesium Sulfate ($MgSO_4$) | 120.37 | 1.6E−01 | 4.8E−01 | 1.9E+04 | 5.8E+04 |
| Potassium chloride (KCl) | 74.55 | 1.6E+00 | 4.9E+00 | 1.2E+05 | 3.6E+05 |
| Sodium bicarbonate ($NaHCO_3$) | 84.01 | 9.0E+00 | 4.4E+01 | 7.6E+05 | 3.7E+06 |
| Sodium chloride (NaCl) | 58.44 | 4.7E+01 | 1.4E+02 | 2.8E+06 | 8.3E+06 |
| Sodium phosphate, dibasic (Anhydrous) | 141.96 | 2.0E−01 | 5.9E−01 | 2.8E+04 | 8.3E+04 |
| Sodium phosphate, monobasic monohydrate ($NaH_2PO_4$—$H_2O$) | 137.99 | 1.8E−01 | 5.3E−01 | 2.4E+04 | 7.3E+04 |
| TRACE MINERALS | | | | | |
| Ferric Nitrate ($Fe(NO_3)_3$—$9H_2O$) | 404 | 4.9E−05 | 1.9E−04 | 2.0E+01 | 7.5E+01 |
| Ferrous sulfate heptahydrate ($FeSO_4$—$7H_2O$) | 278.01 | 5.9E−04 | 1.8E−03 | 1.6E+02 | 4.9E+02 |
| Copper(II) sulfate pentahydrate ($CuSO_4$—$5H_2O$) | 249.69 | 2.0E−06 | 8.0E−06 | 5.1E−01 | 2.0E+00 |
| Zinc sulfate heptahydrate ($ZnSO_4$—$7H_2O$) | 287.56 | 5.9E−04 | 1.8E−03 | 1.7E+02 | 5.1E+02 |
| Ammonium Metavanadate $NH_4VO_3$ | 116.98 | 5.5E−06 | 1.6E−05 | 6.4E−01 | 1.9E+00 |
| Manganese Sulfate monohydrate ($MnSO_4$—$H_2O$) | 169.02 | 9.9E−07 | 3.0E−06 | 1.7E−01 | 5.0E−01 |
| $NiSO_4$—$6H_2O$ | 262.85 | 4.9E−07 | 1.5E−06 | 1.3E−01 | 3.8E−01 |
| Selenium | 78.96 | 8.9E−05 | 2.7E−04 | 7.0E+00 | 2.1E+01 |
| Sodium Meta Silicate $Na_2SiO_3$—$9H_2O$ | 284.2 | 4.8E−04 | 1.4E−03 | 1.4E+02 | 4.1E+02 |
| $SnCl_2$ | 189.62 | 6.2E−07 | 1.9E−06 | 1.2E−01 | 3.5E−01 |
| Molybdic Acid, Ammonium salt | 1235.86 | 9.9E−07 | 3.0E−06 | 1.2E+00 | 3.7E+00 |
| $CdCl_2$ | 183.32 | 6.1E−06 | 1.8E−05 | 1.1E+00 | 3.4E+00 |
| $CrCl_3$ | 158.36 | 9.9E−07 | 3.0E−06 | 1.6E−01 | 4.7E−01 |
| $AgNO_3$ | 169.87 | 4.9E−07 | 1.5E−06 | 8.3E−02 | 2.5E−01 |
| $AlCl_3$—$6H_2O$ | 241.43 | 2.4E−06 | 7.3E−06 | 5.9E−01 | 1.8E+00 |
| Barium Acetate ($Ba(C_2H_3O_2)_2$) | 255.42 | 4.9E−06 | 1.5E−05 | 1.3E+00 | 3.8E+00 |
| $CoCl_2$—$6H_2O$ | 237.93 | 4.9E−06 | 1.5E−05 | 1.2E+00 | 3.5E+00 |
| $GeO_2$ | 104.64 | 2.5E−06 | 7.5E−06 | 2.6E−01 | 7.8E−01 |
| KBr | 119 | 4.9E−07 | 1.5E−06 | 5.9E−02 | 1.8E−01 |
| KI | 166 | 5.0E−07 | 1.5E−06 | 8.3E−02 | 2.5E−01 |
| NaF | 41.99 | 4.9E−05 | 1.5E−04 | 2.1E+00 | 6.2E+00 |
| RbCl | 120.92 | 4.9E−06 | 1.5E−05 | 5.9E−01 | 1.8E+00 |
| $ZrOCl_2$—$8H_2O$ | 178.13 | 4.9E−06 | 1.5E−05 | 8.7E−01 | 2.6E+00 |
| ENERGY SUBSTRATES | | | | | |
| D-Glucose | 180.16 | 6.9E+00 | 2.1E+01 | 1.2E+06 | 3.7E+06 |
| Sodium Pyruvate | 110.04 | 2.0E−01 | 5.9E−01 | 2.2E+04 | 6.5E+04 |
| LIPIDS | | | | | |
| Linoleic Acid | 280.45 | 9.4E−05 | 2.8E−04 | 2.6E+01 | 7.9E+01 |
| Lipoic Acid | 206.33 | 2.0E−04 | 7.8E−04 | 4.1E+01 | 1.6E+02 |
| Arachidonic Acid | 304.47 | 6.5E−06 | 1.9E−05 | 2.0E+00 | 5.9E+00 |
| Cholesterol | 386.65 | 5.6E−04 | 1.7E−03 | 2.2E+02 | 6.5E+02 |
| DL-alpha tocopherol-acetate | 472.74 | 1.5E−04 | 4.4E−04 | 6.9E+01 | 2.1E+02 |
| Linolenic Acid | 278.43 | 3.5E−05 | 1.0E−04 | 9.7E+00 | 2.9E+01 |
| Myristic Acid | 228.37 | 4.3E−05 | 1.3E−04 | 9.8E+00 | 2.9E+01 |
| Oleic Acid | 282.46 | 3.5E−05 | 1.0E−04 | 9.8E+00 | 2.9E+01 |
| Palmitic Acid | 256.42 | 3.8E−05 | 1.1E−04 | 9.8E+00 | 2.9E+01 |
| Palmitoleic acid | 254.408 | 3.9E−05 | 1.2E−04 | 9.8E+00 | 2.9E+01 |
| Stearic Acid | 284.48 | 3.4E−05 | 1.0E−04 | 9.8E+00 | 2.9E+01 |
| AMINO ACIDS | | | | | |
| L-Alanine | 89.09 | 2.5E−02 | 2.1E−01 | 2.2E+03 | 1.8E+04 |
| L-Arginine hydrochloride | 147.2 | 2.7E−01 | 1.5E+00 | 4.0E+04 | 2.2E+05 |
| L-Asparagine-$H_2O$ | 150.13 | 5.0E−02 | 2.1E−01 | 7.5E+03 | 3.1E+04 |
| L-Aspartic acid | 133.1 | 2.5E−02 | 2.1E−01 | 3.3E+03 | 2.7E+04 |
| L-Cysteine-HCl—$H_2O$ | 175.63 | 3.9E−02 | 1.2E−01 | 6.9E+03 | 2.1E+04 |
| L-Cystine dihydrochloride | 313.22 | 3.9E−02 | 1.2E−01 | 1.2E+04 | 3.7E+04 |
| L-Glutamic acid | 147.13 | 2.5E−02 | 2.1E−01 | 3.7E+03 | 3.0E+04 |
| L-Glutamine | 146.15 | 1.5E+00 | 4.4E+00 | 2.1E+05 | 6.4E+05 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| Glycine | 75.07 | 1.5E−01 | 4.4E−01 | 1.1E+04 | 3.3E+04 |
| L-Histidine monohydrochloride monohydrate | 209.63 | 5.9E−02 | 1.8E−01 | 1.2E+04 | 3.7E+04 |
| L-Isoleucine | 131.17 | 1.6E−01 | 4.9E−01 | 2.1E+04 | 6.4E+04 |
| L-Leucine | 131.17 | 1.8E−01 | 5.3E−01 | 2.3E+04 | 7.0E+04 |
| L-Lysine hydrochloride | 182.65 | 2.0E−01 | 5.9E−01 | 3.6E+04 | 1.1E+05 |
| L-Methionine | 149.21 | 4.5E−02 | 1.4E−01 | 6.8E+03 | 2.0E+04 |
| L-Phenylalanine | 165.19 | 8.5E−02 | 2.5E−01 | 1.4E+04 | 4.2E+04 |
| L-Proline | 115.13 | 1.1E−01 | 3.2E−01 | 1.2E+04 | 3.7E+04 |
| L-Serine | 105.09 | 1.5E−01 | 4.4E−01 | 1.5E+04 | 4.6E+04 |
| L-Threonine | 119.12 | 1.8E−01 | 5.3E−01 | 2.1E+04 | 6.3E+04 |
| L-Tryptophan | 204.23 | 1.7E−02 | 5.2E−02 | 3.5E+03 | 1.1E+04 |
| L-Tyrosine disodium salt hydrate | 225.15 | 8.4E−02 | 3.7E−01 | 1.9E+04 | 8.4E+04 |
| L-Valine | 117.15 | 1.8E−01 | 5.3E−01 | 2.1E+04 | 6.2E+04 |
| VITAMINS | | | | | |
| Ascorbic acid | 176.12 | 1.3E−01 | 3.8E−01 | 2.2E+04 | 6.7E+04 |
| Biotin | 244.31 | 5.6E−06 | 1.7E−05 | 1.4E+00 | 4.1E+00 |
| $B_{12}$ | 1355.37 | 2.0E−04 | 5.9E−04 | 2.7E+02 | 8.0E+02 |
| Choline chloride | 139.62 | 2.5E−02 | 7.5E−02 | 3.5E+03 | 1.1E+04 |
| D-Calcium pantothenate | 238.27 | 1.8E−03 | 1.4E−02 | 4.4E+02 | 3.4E+03 |
| Folic acid | 441.4 | 2.4E−03 | 7.1E−03 | 1.0E+03 | 3.1E+03 |
| i-Inositol | 180.16 | 2.7E−02 | 1.1E−01 | 4.9E+03 | 1.9E+04 |
| Niacinamide | 122.12 | 6.5E−03 | 2.0E−02 | 7.9E+02 | 2.4E+03 |
| Pyridoxine hydrochloride | 205.64 | 3.8E−03 | 1.1E−02 | 7.8E+02 | 2.4E+03 |
| Riboflavin | 376.36 | 2.3E−04 | 6.8E−04 | 8.6E+01 | 2.6E+02 |
| Thiamine hydrochloride | 337.27 | 3.3E−03 | 3.6E−02 | 1.1E+03 | 1.2E+04 |
| GROWTH FACTORS/PROTEINS | | | | | |
| GABA | 103.12 | 0 | 1.5E+00 | 0 | 1.5E+05 |
| Pipecolic Acid | 129 | 0 | 1.5E−03 | 0 | 1.9E+02 |
| bFGF | 18000 | 0 | 2.17E−07 | 0 | 3.9E+00 |
| TGF beta 1 | 25000 | 0 | 3.5E−08 | 0 | 8.8E−01 |
| Human Insulin | 5808 | 0 | 5.9E−03 | 0 | 3.4E+04 |
| Human Holo-Transferrin | 78500 | 0 | 2.1E−04 | 0 | 1.6E+04 |
| Human Serum Albumin | 67000 | 0 | 2.9E−01 | 0 | 2.0E+07 |
| Glutathione (reduced) | 307.32 | 0 | 9.6E−03 | 0 | 2.9E+03 |
| OTHER COMPONENTS | | | | | |
| Hypoxanthine Na | 136.11 | 5.9E−03 | 2.6E−02 | 8.0E+02 | 3.6E+03 |
| Phenol red | 354.38 | 8.5E−03 | 2.5E−02 | 3.0E+03 | 9.0E+03 |
| Putrescine-2HCl | 161.07 | 2.0E−04 | 5.9E−04 | 3.2E+01 | 9.5E+01 |
| Thymidine | 242.229 | 5.9E−04 | 1.8E−03 | 1.4E+02 | 4.3E+02 |
| 2-mercaptoethanol | 78.13 | 4.9E−02 | 1.5E−01 | 3.8E+03 | 1.1E+04 |
| Pluronic F-68 | 8400 | 1.2E−02 | 3.5E−02 | 9.8E+04 | 2.9E+05 |
| Tween 80 | 1310 | 1.6E−04 | 4.9E−04 | 2.2E+02 | 6.5E+02 |

The liquid phase of the cell culture medium may be water, serum, or albumin.

Many of the ingredients or components listed above in Table 1 are not necessary, or can be used in lower concentrations.

It is contemplated that the cell culture medium may contain insulin or an insulin substitute. Similarly, the cell culture medium may contain transferrin or a transferrin substitute.

In more specific embodiments, it is contemplated that the cell culture medium may not (1) contain albumin, (2) insulin or insulin substitute, (3) transferrin or transferrin substitute, or any combination of these three components.

It should be noted that other cell culture mediums may contain growth factors such as interleukin-1 beta (IL-1β or catabolin), interleukin-6 (IL6), or pigment epithelium derived factor (PEDF). Such growth factors are not present in the cell culture medium of the present disclosure.

One specific formula for a cell culture medium is provided in Table 2:

TABLE 2

| Ingredient | Amount | Unit |
|---|---|---|
| bFGF | 0.39 | microgram (µg) |
| Albumin | 1.34 | milligram (mg) |
| Insulin | 2 | mg |
| Lithium Chloride | 4.23 | mg |
| GABA | 0.01 | mg |
| TGF beta 1 | 0.06 | µg |
| Pipecolic acid | 0.013 | mg |
| L-glutamine | 2.92 | grams |
| MEM non-essential amino acid solution | 1 | mL |
| DMEM/F12 | 100 | mL |

In this regard, MEM non-essential amino acid solution is typically provided in a 100× concentrate. The MEM of Table 2 is used after dilution back to 1×, and contains the following amino acids in the following concentration listed in Table 3:

TABLE 3

| MEM Amino Acids | Concentration (ng/mL) |
| --- | --- |
| Glycine | 7.50E+03 |
| L-Alanine | 8.90E+03 |
| L-Asparagine | 1.32E+04 |
| L-Aspartic acid | 1.33E+04 |
| L-Proline | 1.15E+04 |
| L-Serine | 1.05E+04 |

DMEM/F12 contains the following ingredients listed in Table 4:

TABLE 4

| DMEM/F12 Ingredients | Concentration (ng/mL) |
| --- | --- |
| Glycine | 187.5 |
| L-Alanine | 44.5 |
| L-Arginine hydrochloride | 1475 |
| L-Asparagine-$H_2O$ | 75 |
| L-Aspartic acid | 66.5 |
| L-Cysteine hydrochloride-$H_2O$ | 175.6 |
| L-Cystine 2HCl | 312.9 |
| L-Glutamic Acid | 73.5 |
| L-Glutamine | 3650 |
| L-Histidine hydrochloride-$H_2O$ | 314.8 |
| L-Isoleucine | 544.7 |
| L-Leucine | 590.5 |
| L-Lysine hydrochloride | 912.5 |
| L-Methionine | 172.4 |
| L-Phenylalanine | 354.8 |
| L-Proline | 172.5 |
| L-Serine | 262.5 |
| L-Threonine | 534.5 |
| L-Tryptophan | 90.2 |
| L-Tyrosine disodium salt dihydrate | 557.9 |
| L-Valine | 528.5 |
| Biotin | 0.035 |
| Choline chloride | 89.8 |
| D-Calcium pantothenate | 22.4 |
| Folic Acid | 26.5 |
| Niacinamide | 20.2 |
| Pyridoxine hydrochloride | 20 |
| Riboflavin | 2.19 |
| Thiamine hydrochloride | 21.7 |
| Vitamin $B_{12}$ | 6.8 |
| i-Inositol | 126 |
| Calcium Chloride ($CaCl_2$) (anhyd.) | 1166 |
| Cupric sulfate ($CuSO_4$—$5H_2O$) | 0.013 |
| Ferric Nitrate ($Fe(NO_3)_3$—$9H_2O$) | 0.5 |
| Ferric sulfate ($FeSO_4$—$7H_2O$) | 4.17 |
| Magnesium Chloride (anhydrous) | 286.4 |
| Magnesium Sulfate ($MgSO_4$) (anhyd.) | 488.4 |
| Potassium Chloride (KCl) | 3118 |
| Sodium Bicarbonate ($NaHCO_3$) | 24380 |
| Sodium Chloride (NaCl) | 69955 |
| Sodium Phosphate dibasic ($Na_2HPO_4$) anhydrous | 710.2 |
| Sodium Phosphate monobasic ($NaH_2PO_4$—$H_2O$) | 625 |
| Zinc sulfate ($ZnSO_4$—$7H_2O$) | 4.32 |
| D-Glucose (Dextrose) | 31510 |
| Hypoxanthine Na | 23.9 |
| Linoleic Acid | 0.42 |
| Lipoic Acid | 1.05 |
| Phenol Red | 81 |
| Putrescine 2HCl | 0.81 |
| Sodium Pyruvate | 550 |
| Thymidine | 3.65 |

The combination of the laminin substrate with the cell culture medium of the present disclosure results in a cell culture system that can be cheaper, yet provides higher efficiency in maintaining pluripotent stem cells. In essence, all that is required is a laminin and a minimal amount of nutrition. It is particularly contemplated that the laminin used in combination with this cell culture medium is either LN-511 or LN-521.

The following examples are for purposes of further illustrating the present disclosure. The examples are merely illustrative and are not intended to limit devices made in accordance with the disclosure to the materials, conditions, or process parameters set forth therein.

EXAMPLES

Example 1

Cloning of the Human Laminin β2 cDNA

The 5.6 kb fragment of human laminin β2 cDNA was PCR-amplified from human liver cDNA library (BD Biosciences) using primers 5'-GTGGTACC-CACAGGCAGAGTTGAC-3' (SEQ ID NO: 7) and 5'-GCTCTAGAGCTCTTCAGTGCATAGGC-3' (SEQ ID NO: 8) thus introducing artificial XbaI and KpnI cutting sites on the ends of the fragment. To decrease the error rate during the PCR amplification, Phusion™ high-fidelity PCR Kit (Finnzymes) was used. Subsequently, the fragment was digested with XbaI and KpnI and subcloned into pSK vector digested with the same restriction endonucleases (pSKHLAMB2 plasmid). To verify the integrity of the sequence, several clones of pSKHLAMB2 plasmid were sequenced. Sequencing was performed on an ABI PRISM™ 310 Genetic Analyzer (Perkin Elmer) using ABI PRISM® BigDye™ Terminator Cycle Sequencing kit (PE Applied Biosystems). Only complete matches with the NCBI database human laminin β2 sequence were selected for further cloning.

Expression Constructs

For expression of the human laminin β2 chain pSKHLAMB2 plasmid was digested with XbaI and KpnI and subcloned into XbaI-KpnI treated pcDNA 3.1(+) vector (Invitrogen).

The constructs used for expression of human laminin α5 (HLN5Full.pcDNA construct) and γ1 (HG1 construct) have been described previously (Doi, M. et al., J. Biol. Chem. 277(15), 12741-8 (2002)).

Antibodies

Anti-laminin β2 (MAB2066) monoclonal antibody (mAb) was purchased from R@D Systems. Anti-laminin α5 mAb (2F7) was purchased from Abnova. Anti-laminin β1 mAb (MAB1921) was purchased from Chemicon. Anti-laminin γ1 (H-190) rabbit polyclonal antibody was purchased from Santa Cruz Biotechnology, Inc.

Production and Purification of Recombinant Laminin-521 r-laminin-521 was produced in human embryonic kidney cells (HEK293, ATCC CRL-1573) cultured in DMEM, 10% FCS in humidified 5% $CO_2$ atmosphere at 37° C. Wild-type cells were transfected using the standard calcium-phosphate method with the HG1 construct and stable colonies were selected using 100 mg/ml hygromycin (Cayla). All further cell culture and clonal expansion was carried out in continuous presence of relevant selection antibiotics. A highly expressing clone was then transfected with the human laminin β2 construct and stable clones were selected using 500 mg/ml G418 (Life Technologies). A clone highly expressing both laminin γ1 and laminin β2 was finally transfected with the HLN5Full.pcDNA construct and stable colonies were selected using 200 mg/ml zeocin (Cayla). The clones showing the highest secretion were expanded further.

For production of r-laminin-521, confluent cells were cultured in DMEM for up to five days. r-laminin-521 was affinity purified using anti-FLAG M2 matrix (Sigma). The collected medium was incubated in batch mode with the matrix overnight at 4° C. with agitation. Bound r-laminin-521 was competitively eluted with 50 mg/ml FLAG peptide (Sigma) in TBS/E (50 mM Tris-Cl, pH 7.5, 150 mM NaCl, 1 mM EDTA) at room temperature. The elute was concentrated and the buffer was replaced by PBS using 30 kD cut-off ultrafiltration (Millipore). Finally the concentrated solution was passed through 0.2 mm filter to remove self-aggregated polymers.

Characterization of Recombinant Laminin-521

Figure 3:
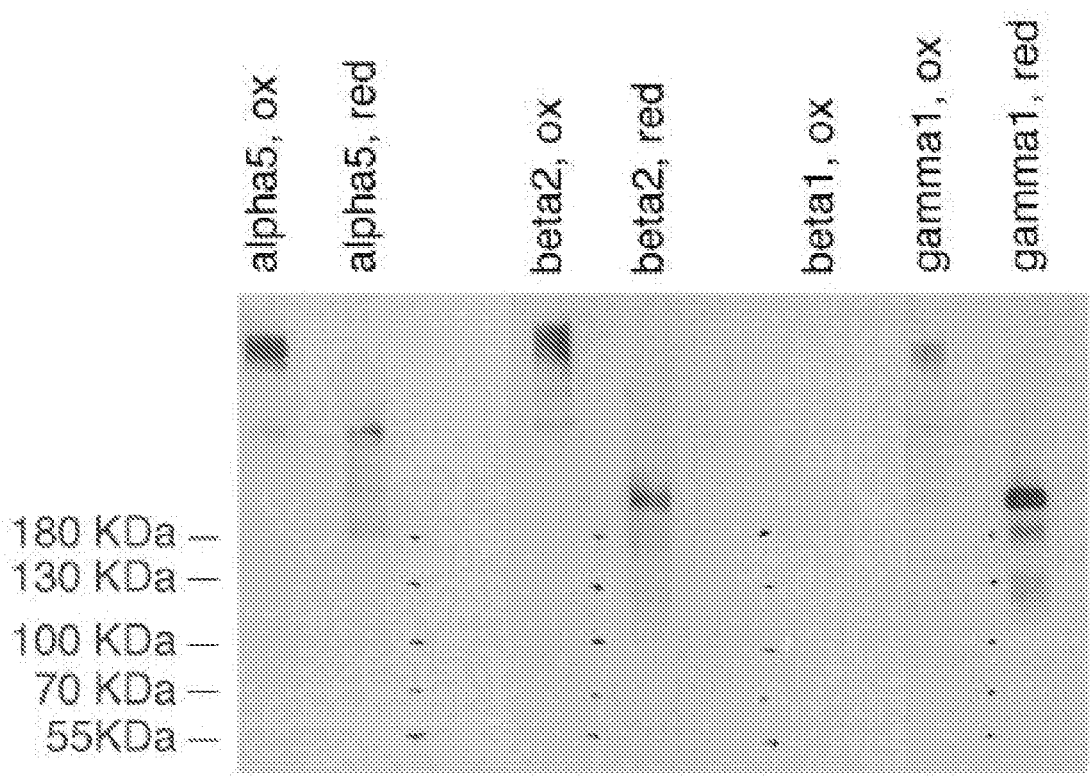
FIG. 3 shows the results of characterization of human recombinant laminin-521 using SDS-PAGE. An immunoblot of recombinant laminin-521 was made under non-reducing (labeled as ox) and reducing (labeled as red) conditions. Proteins on 3-8% gels were transferred onto PVDF membranes followed by staining with antibodies to laminin α5 (2F7), β2 (MAB2066), β1 (MAB1921) and γ1 (H-19).

Secreted laminin in medium and after purification was characterized using 3-8% gradient SDS-PAGE. Proteins were visualized using Sypro staining (Bio-Rad) or transferred onto PVDF (FIG. 3). The membranes were probed with antibodies described above. After washing, the membranes were incubated with HRP-conjugated goat antibodies. The immunoreactivity was detected by a chemiluminescent kit (Life Science Products) according to the manufacturer's instructions.

Methods

Human ES Cell Cultures.

Human ES cells were cultured on r-laminin-521-coated laboratory dishes in chemically defined O3 medium (described in Rodin et al., Nature Biotechnol., vol. 28, pp. 611-615 (2010)) at 37° C. in 5% CO2. Cells were routinely passed once every 10-12 days by exposure to Trypsin-EDTA solution (GIBCO Invitrogen) for 5 minutes at 37° C. They were then gently pipetted to break into single-cell suspension and defined trypsin inhibitor (GIBCO Invitrogen) was added. The cell suspension was centrifuged at for 4 minutes, the supernatant discarded, the cell pellet resuspended in prewarmed O3 medium, and cells were then passed through a 40 μm sieve. After that cells were plated on new r-laminin-521-coated dishes at a concentration 30 Kcells/cm² (1:25-1:30 split ratio). Cells were fed once a day with fresh medium prewarmed in an incubator for 1 hour, except for the first day after a passage, when only a few drops of fresh medium were added. Control cells of the same line were cultured on Matrigel (BD Biosciences) in O3 medium as described in Rodin et al., Nature Biotechnol., vol. 28, pp. 611-615 (2010). Control cells were passaged in pieces.

Cell Culture Dish Coating.

Ninety-six-well tissue cell culture plates were coated overnight at 4° C. with sterile solutions of the ECM proteins mouse LN-111 (Invitrogen), human recombinant LN-511, and human recombinant LN-521, all at a concentration of 30 μg/ml (5 μg/cm²). For control cells, BD Matrigel™ hESC qualified (BD Biosciences) was used according to the manufacturer's instructions.

Cell Adhesion Assay.

The assay was performed as described (Extracellular Matrix Protocols, 2000). Briefly, 96-well plates were coated by extracellular matrix proteins as described above and blocked by O3 medium containing bovine serum albumin. The ES cells were plated at a cell density of 600 cell/mm² upon extracellular matrix-coated plates and were left to adhere for either 1 hour or 1 day at the cell incubator. Non-adherent cells were washed away, and adherent cells were fixed for 20 min by 5% glutaraldehyde, stained by 0.1% Crystal Violet.

Real-Time PCR Quantification of mRNAs.

Total RNA was isolated and cDNA was synthesized as described in Rodin et al., Nature Biotechnol., vol. 28, pp. 611-615 (2010). Real-time quantitative RT-PCR Taqman assays were performed using the Applied Biosystems 7300 Real-Time PCR System. All reactions were done in quadruplicate with predeveloped gene expression assay mix (Applied Biosystems) containing primers and a probe for the mRNA of interest. Additional reactions for each experiment included predeveloped gene expression assay mix for GAPDH, used to normalize the RNA input. All data were analyzed with 7300 System SDS Software version 1.4.

FACS Analysis.

OCT4 expression was analyzed as described in Ludwig, T. E. et al. Derivation of human embryonic stem cells in defined conditions. Nat. Biotechnol. 24, 185-187 (2006). Cells were run on FACSCalibur Flow Cytometer (Becton Dickinson). Data were analyzed with CellQuest software (Becton Dickinson).

Results for Example 1

Figure 4:
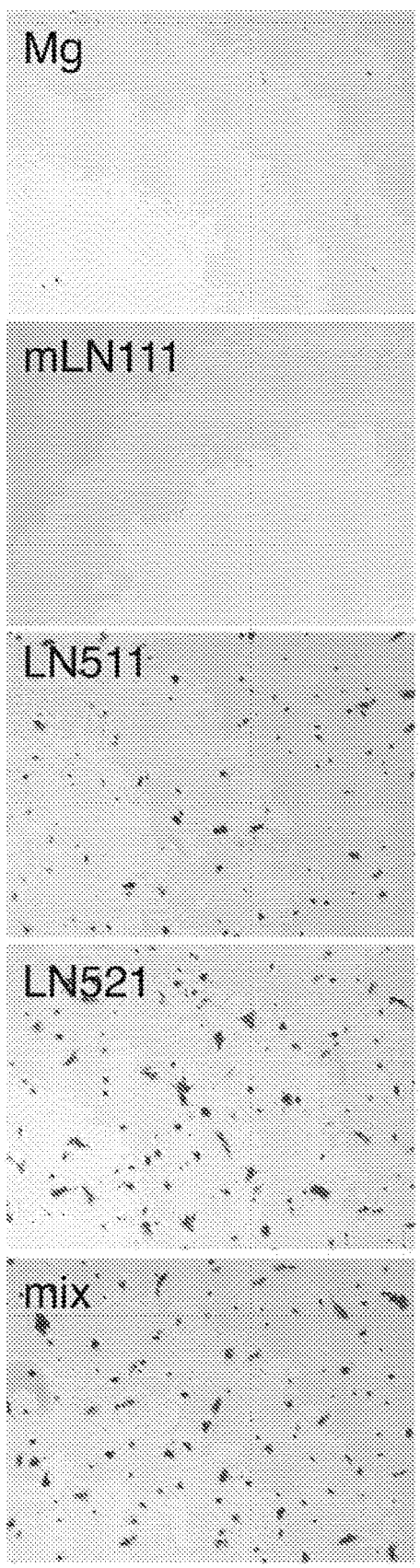
FIGS. 4 and 5 show the Crystal Violet staining of human ES cells adherent to dishes coated in Matrigel (Mg), mouse laminin-111 (mLN111), human recombinant-laminin-511 (r-laminin-511 or r-LN-511), human recombinant-laminin-521 (r-laminin-521 or r-LN-521), or a mixture of r-laminin-511 and r-laminin-521 (mix) after one day in culture. Both Figures are magnified 5×.

To find out how different cell culture coatings affect single cell survival of human ES cells in O3 medium without any additives, we completely dissociated HS181 cells and plated them on either Matrigel, mouse laminin-111, human r-laminin-511, human r-laminin-521, or a mixture of r-laminin-511 and r-laminin-521. The results are seen in FIG. 4. As expected, almost no cells remained attached to Matrigel or mouse laminin-111 by 24 hours after plating. In contrast, the cells on human r-laminin-521, the mixture, and at a less extent on human r-laminin-511 survived.

Figure 5:
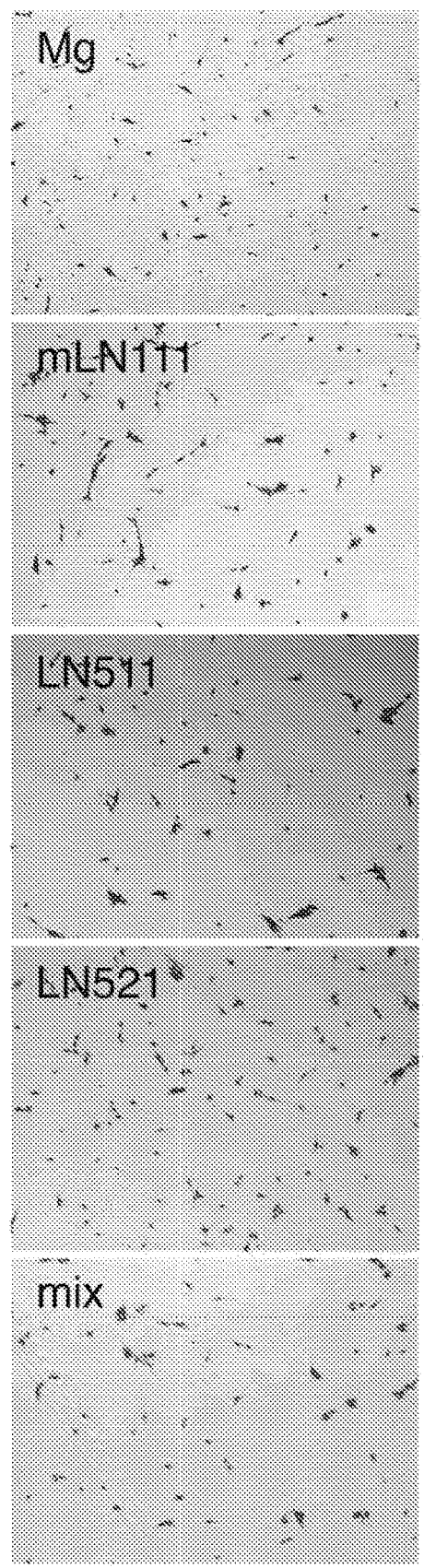

The experiment was repeated on human ES cells in O3 medium treated with ROCK inhibitor Y-27632. These results are seen in FIG. 5. The stem cells remained attached on all 5 coatings.

Figure 6:
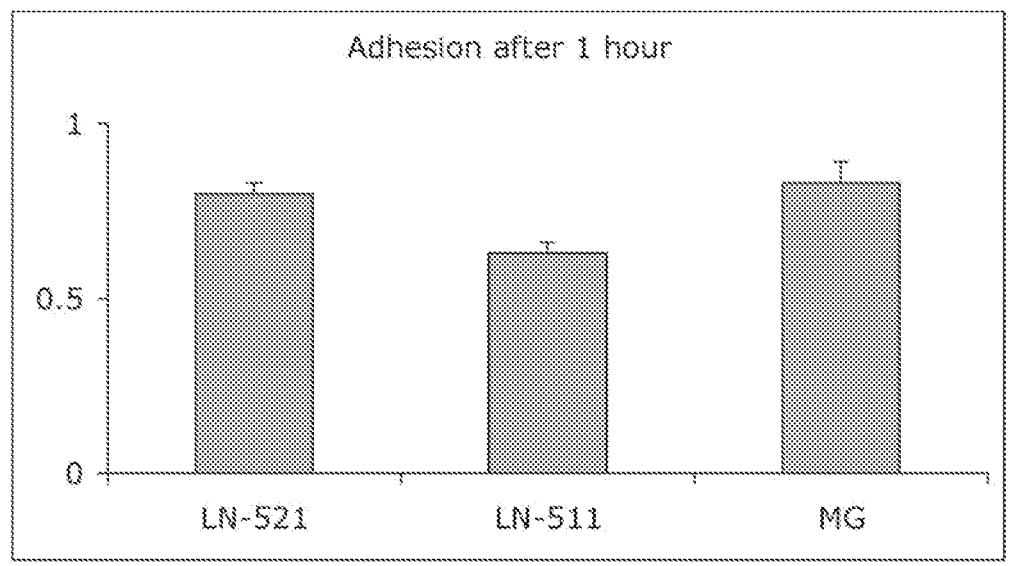
FIG. 6 is a graph showing the adhesion of human ES cells to human r-laminin-521 (labeled as LN521), human r-laminin-511 (LN511), and Matrigel (Mg) coated dishes after one hour in culture without ROCK inhibitor. Error bars show the standard error of measurement. (n=3).

To quantify this effect, we performed cell adhesion experiments on all of the above-mentioned coatings at 1 hour and 1 day after plating (i.e., each of the five coatings, with and without Y-27632). FIG. 6 shows the results for the 1-hour experiment for LN-521, LN-511, and Matrigel (MG) without Y-27632. The adhesion of human ES cells in O3 medium without any additives was roughly the same at this time point.

Figure 7:
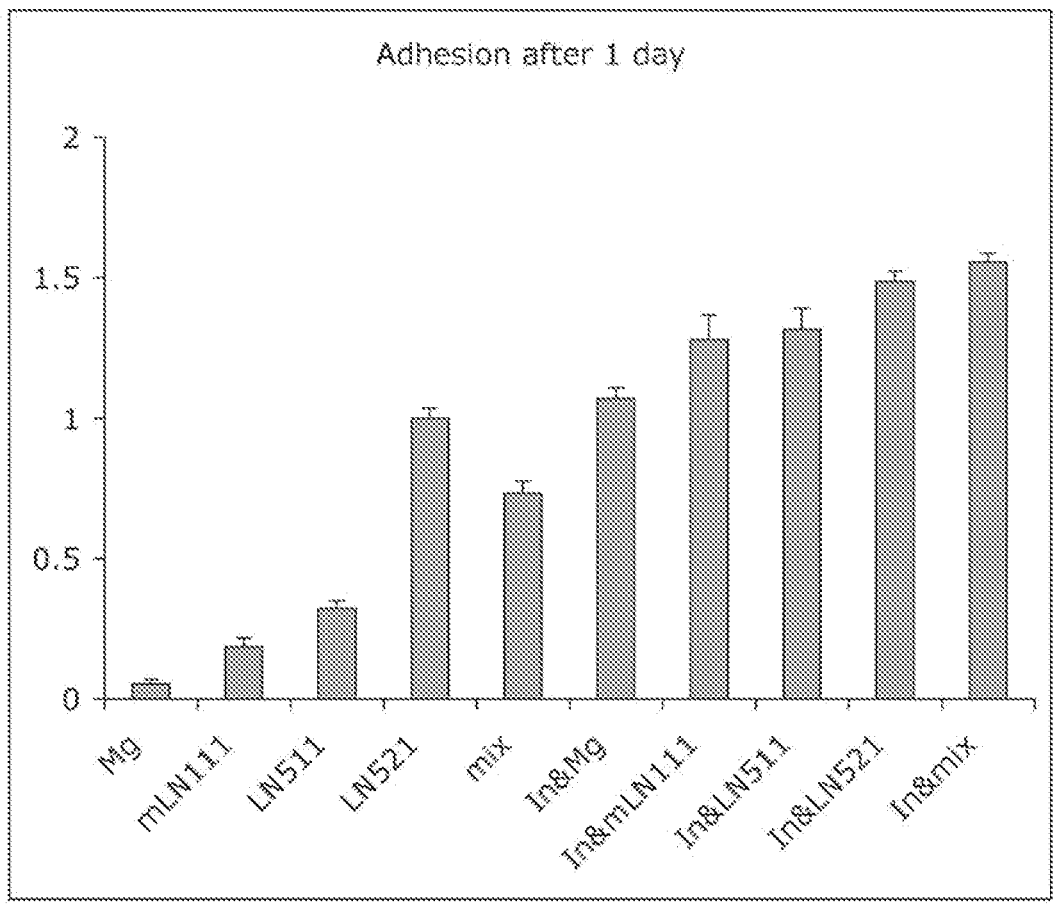
FIG. 7 is a graph showing the adhesion of human ES cells to dishes coated in either Matrigel (Mg), mouse laminin-111 (mLN111), human r-laminin-511 (LN511), human r-laminin-521 (LN521), or a mixture of r-laminin-511 and r-laminin-521 (mix), after one day in culture and without ROCK inhibitor. Also included are results for dishes with ROCK inhibitor and either Matrigel (In&Mg), mouse laminin-111 (In&mLN111), human r-laminin-511 (In&LN511), human r-laminin-521 (In&LN521), or a mixture of r-laminin-511 and r-laminin-521 (In&mix), also after one day in culture. The cells for both experiments were plated at the same density on the same cell culture dish. Error bars show standard error of measurement (n=3).

FIG. 7 shows the results for the 1-day experiment for all of the coatings. The plates containing the Y-27632 inhibitor are labeled as "In&" along with the coating. At 1 day after plating, the stem cells adhered to LN-521 without additives 20 times better than to Matrigel without additives. In addition, the results showed that the adhesion of cells to LN-521 without additives was similar to the adhesion of cells on all dishes including the ROCK inhibitor. In other words, no ROCK inhibitor is necessary with LN-532 coating to obtain results similar to coatings that do contain the ROCK inhibitor.

Figure 8:
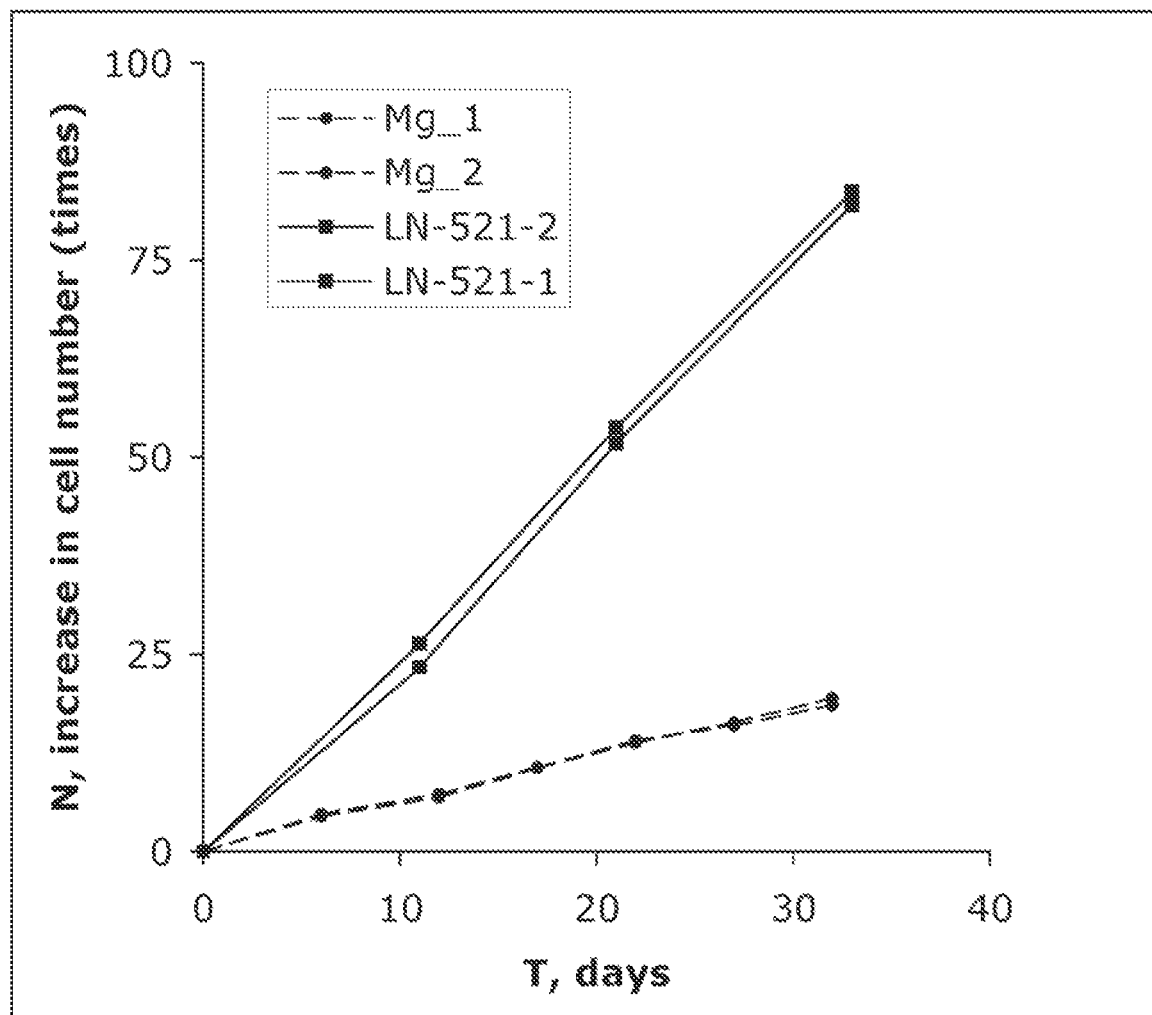
FIG. 8 shows the growth curves for human ES cells cultured on r-laminin-521 (LN-521_1 and LN-521_2) using single cell dissociation passaging and for human ES cells cultured on Matrigel (Mg_1 and Mg_2) using passaging in small clumps. The latter cells were passaged as described in Rodin et al., Nature Biotechnol., vol. 28, pp. 611-615 (2010).

We cultured human ES cells on human r-laminin-521. passaging them after complete dissociation into single cell suspension every 10-12 days in 1:25 to 1:30 ratios. The cells proliferated robustly with a stable and high rate for at least 9 passages (3 months). Moreover, after 3 passages (1 month), they underwent the same number of cell doublings as stem cells after 20 passages (100 days) cultured using conventional methods. This is illustrated in FIG. 8, which shows the increase in the number of cells versus time. The cells on LN-521 increased at a much faster rate than on Matrigel. Thus, the new r-laminin-521 hES cell culture method was advantageous in terms of time and labor.

Figure 9:
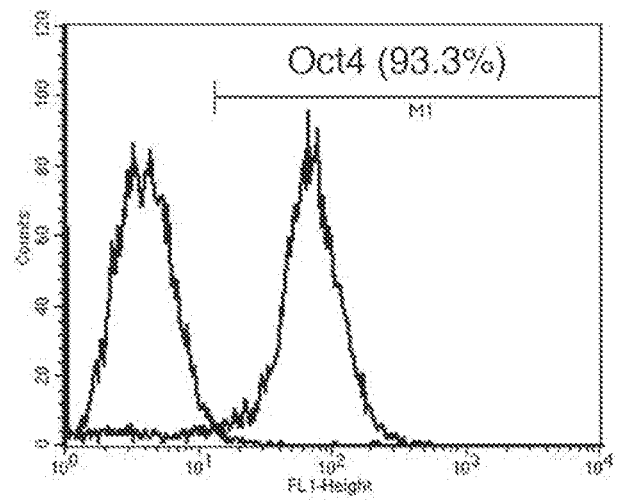
FIG. 9 is a FACS analysis of human ES cells after several single cell dissociation passages on r-laminin-521 for OCT4, a marker of pluripotency. The percentage of positive cells is listed in parentheses.
Figure 10:
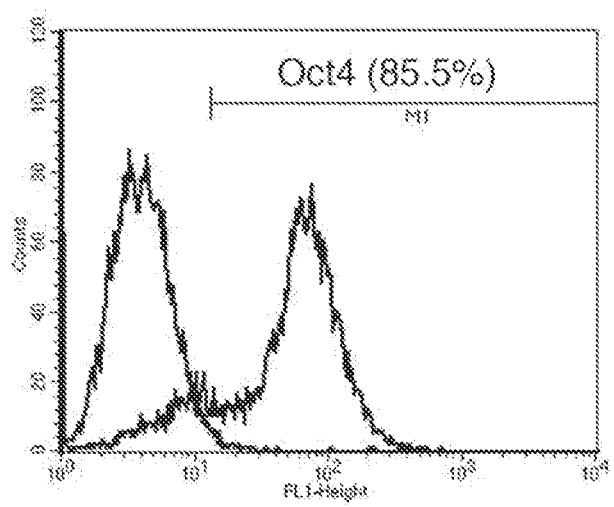
FIG. 10 is a FACS analysis of human ES cells after several passages on Matrigel using splitting in small clumps for OCT4. The percentage of positive cells is listed in parentheses.

To confirm the identity of hES cells after several single cell suspension passages on human r-laminin-521 in O3 medium without any additives, we performed FACS analysis for Oct4, a marker of pluripotency. FIG. 9 shows the results for cells grown on r-LN-521, while FIG. 10 shows the results for cells grown on Matrigel. The percentage of positive cells is listed in parentheses. R-LN-521 had a much higher percentage of pluripotent cells.

Figure 11:
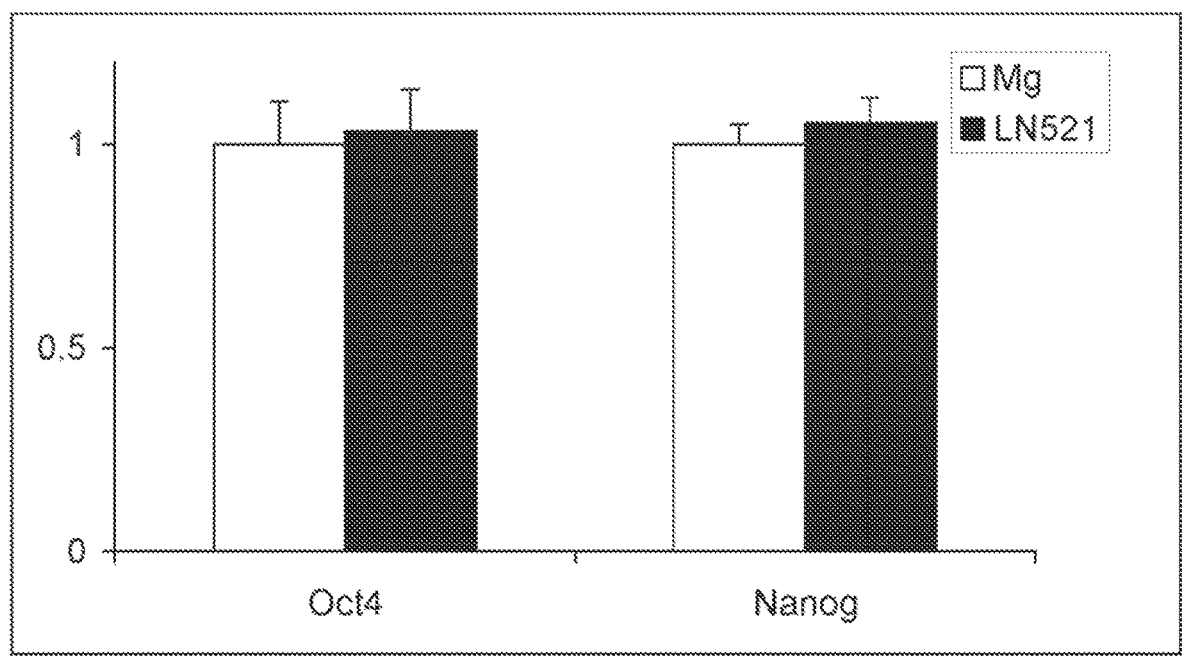
FIG. 11 shows the results of a real-time quantitative RT-PCR analysis which was used to compare numbers of mRNA transcripts of the pluripotency markers Oct4 and Nanog in human ES cells cultured on human r-laminin-521 (LN521) after several single cell dissociation passaging and in the cells cultured on Matrigel (Mg) after several passaging of the cells in clumps. Error bars show 95% confidence intervals.

In addition, the number of mRNA transcripts of the pluripotency markers Oct4 and Nanog was quantified. FIG. 11 shows these results. For both markers, the cells on LN-521 showed higher numbers of transcripts.

Both methods showed that the new methods provides hES cells of the same or better quality than the current method, which uses Matrigel as a cell culture dish coating material and passaging of the cells in small clumps.

Example 2

In this Example 2, expressed and purified recombinant LN-521 that was also expressed in pluripotent hES cells was studied for its effects on cultured hES and iPS cells. The results showed that LN-521, alone, strongly supports self-renewal of pluripotent hES and iPS cells, and, importantly, it allows survival of pluripotent stem cells following plating of trypsinized stem cells in single cell suspension on LN-521 at high dilutions. The effects of LN-521 were shown to be mediated by signaling via $\alpha 6\beta 1$ integrin through induction of hES cell migration and PI3K/Akt pathway activation. The results may be applied for an effective and even automated expansion method for large-scale production of pluripotent hES and iPS cells, as well as for development of new medium formulations for self-renewal of pluripotent stem cells. The new hES/hiPS cell culture method described here closely resembles standard cell culture methods, e.g. that are used to culture fibroblasts, and, therefore, it does not demand special skills. It consumes significantly less cell coating material per one cell division and is time efficient, thus providing significant economical profits in comparison with the previous procedures for culturing hES/hiPS cells.

Human recombinant LN-521, which has previously not been available in pure form, was produced by cloning full-length laminin $\beta 2$ cDNA and carrying out a triple-transfection of HEK293 cells with the human laminin $\alpha 5$, $\beta 2$ and $\gamma 1$ chains. Human recombinant LN-111 and LN-121 were similarly generated following cloning of full-length $\alpha 1$, and $\beta 2$ chain cDNAs and triple transfection of HEK293 cells with human $\alpha 1$, $\beta 1$ and $\gamma 1$ and $\alpha 1$, $\beta 2$ and $\gamma 1$ chain cDNAs, respectively. The purified LN-521, LN-111 and LN-121 proteins were shown to contain, respectively, pure $\alpha 5$, $\beta 2$, and $\gamma 1$ chains, $\alpha 1$, $\beta 1$ and $\gamma 1$ chains, as well as $\alpha 1$, $\beta 2$ and $\gamma 1$ chains, as shown by protein staining and Western blot analysis.

Methods

Human ES and iPS Cell Cultures.

Human ES cells of HS181 and HS401 were cultured on LN-521-coated culture dishes in O3 medium (described in Rodin et al., *Nature Biotechnol.*, vol. 28, pp. 611-615 (2010) with pH was adjusted to 7.35), mTeSR1 (STEMCELL Technologies) and chemically defined and xeno-free TeSR2 (STEMCELL Technologies) at 37° C., 5% $CO_2$. Initially, cells of the lines were transferred onto a LN-521 coating from a human feeder cell layer by careful scratching using a sterile knife with subsequent trypsinization, or the cells were trypsinized into single cell suspension from a LN-511 coating. The cells were provided once a day with fresh medium pre-warmed in an incubator for one hour, except for the first day after plating, when only a few drops of fresh medium were added. Cells were routinely passed once in 10-12 days by exposure to Trypsin/EDTA (GIBCO Invitrogen Corporation, Paisley, Scotland) for 5 minutes at 37° C., 5% $CO_2$. They were then gently pipetted to break into single-cell suspension and a Defined Trypsin Inhibitor (GIBCO Invitrogen) was added. The cell suspension was centrifuged at 25 rcf for 4 minutes, the supernatant was discarded, the cell pellet was resuspended in prewarmed O3 medium, and the cells were then passed through a 40 μm sieve. Subsequently, the cells were plated on new LN-521-coated dishes at a concentration of 30,000 cells/cm² in 1:25-1:30 split ratios. Control cells of the same line were cultured on Matrigel (STEMCELL Technologies) and LN-511 in O3 medium as described previously.[9]

For defined and xeno-free cultures, TeSR2 (STEMCELL Technologies) medium and defined free from any animal derived component TrypLE™ Select (GIBCO Invitrogen Corporation, Paisley, Scotland) enzyme were used. The cells were passed every 10-14 days by exposure to TrypLE™ Select for 4-5 minutes at 37° C., 5% $CO_2$. Then, the enzyme was carefully aspirated and prewarmed TeSR2 medium was added. After that, the cells were gently pipetted to break into single-cell suspension, centrifuged, the supernatant was discarded, and the cell pellet was resuspended in prewarmed TeSR2. The cells were then passed through a 40 μm sieve and plated on a fresh LN-521 coated dish.

Tissue cell culture plates were coated overnight at 4° C. with sterile solutions of the ECM proteins, such as human recombinant LN-521, all at a concentration of 30 μg/ml (5 μg/cm²). Control plates were coated with Matrigel according to the STEMCELL Technologies' instructions. Prior to use, dishes were pre-warmed in an incubator for one hour after which prewarmed O3 medium was added without additional washing of the dish. After applying a fresh LN-521 solution to a new dish, the remaining LN-521 solution could be used at least once more. All the adhesion, survival, and inhibition of survival experiments were carried out using fresh coating materials.

The human iPS cells, ChiPSW line, were derived from lentivirally transduced human foreskin fibroblasts (HFF) with OCT-4/SOX2/NANOG/LIN28 reprogramming genes. The ChiPSW line had normal male karyotype, 46,XY, in repeated testing at different passages. Prior to cell culture and passaging experiments, the cells were first characterized in vitro for expression of pluripotency markers. Immunofluorescence study with antibodies against Oct3/4 (SC-5279), Nanog (SC-33759), TRA-1-60 (SC-21705) and SSEA4 (sc-21704) showed that the cells expressed all those markers of pluripotency. RT-PCR analysis confirmed that the cells lacked expression of the viral transgenes. The pluripotency of ChiPSW cells was confirmed by in vitro (embryoid bodies formation and immunofluorescence study) and in vivo (injection subcutaneously into SCID beige mice) experiments. Cells of ChiSW line could be further differentiated into beating cardiomyocytes. They were also capable of undergoing hematopoietic differentiation.

Before taken to the present feeder free cultures, the iPS cells were maintained and expanded over irradiated human foreskin fibroblasts. Knock-out serum (KSR, Invitrogen)-supplemented media was used for propagation, supplemented with 8 ng/ml of basic fibroblast growth factor (bFGF, R&D Systems). Cells were fed on a daily basis and weekly passaged using collagenase IV (1 mg/ml, Roche) or manual dissection when required.

Prior to these experiments, the CutB1.2 cells were shown to express pluripotency markers Oct4/Nanog/Sox2/TRA-1-60/TRA-1-81, to lack expression of the viral transgenes, and the pluripotency of the cells was confirmed both by in vivo and in vitro differentiation studies.

Laminin-521 and Other Coating Materials.

Human recombinant LN-521, available from BioLamina, AB, Stockholm (www.biolamina.com), was produced in human embryonic kidney cells (HEK293; ATCC CRL-1573) sequentially transfected with full-length laminin $\gamma 1$, $\beta 2$ and $\alpha 5$ constructs essentially as described previously. For protein production, the HEK293 cells were cultured in Dulbecco's modified Eagle's medium (DMEM) supplemented with GlutaMax I for up to six days. The LN-521 molecules were affinity-purified using anti-FLAG matrix (Sigma), and then characterized using 3-8% and 4-15% gradient SDS-PAGE under reducing and nonreducing conditions. The proteins were visualized using Sypro Ruby (Bio-Rad) protein staining and immunostaining of the chains on polyvinylidene difluoride membranes. To further characterize the protein, Western blot analysis with antibodies against the laminin $\alpha 5$, $\beta 2$ and $\gamma 1$ chains was performed. Human recombinant laminin-111 and laminin-121 were produced similarly to LN-521 and shown to contain the correct chains of predicted molecular sizes by Western and SDS-PAGE. If not otherwise stated, the corresponding mouse laminin-111 (Invitrogen) was indicated as LN-111.

Reagents and Antibodies.

InSolution™ LY 294002 (a specific Akt inhibitor), InSolution™ Wortmannin (a specific PI3K inhibitor), and InSolution™ 98059 (a specific MEK1/Erk inhibitor) were purchased from Calbiochem. Antibodies to phospho-Akt (#4060), total-Akt (#9272), phospho-Erk (#9101), and total-Erk (#9102) were obtained from Cell Signaling Technology. PathScan Phospho-Akt1 sandwich ELISA kit (#7160), PathScan total Akt1 sandwich ELISA kit (#7170), PathScan Phospho-Akt2 sandwich ELISA kit (#7048), and PathScan total Akt2 sandwich ELISA kit (#7046) were also purchased from Cell Signaling Technology. Antibodies to Calnexin (#ab10286) were obtained from Abcam. Function blocking antibodies to various integrin subunits, mouse isotype antibodies, and $\alpha$-dystroglycan were purchased from Millipore. Since function blocking antibodies to $\alpha V$ (MAB1980) and $\alpha 6$ (MAB1378) were presented in a solution with sodium azide, before the inhibition of survival experiment all the antibodies to alpha integrin subunits were dialyzed thrice against O3 medium for 2 hours each time. Antibodies to Lutheran receptor and $\alpha$-fetoprotein, as well as rat isotype control antibodies were obtained from R&D Systems. Antibodies to Oct4, Nanog, SSEA-4, smooth muscle actin and MAP-2 were purchased from Millipore.

Immunofluorescence.

For immunofluorescence studies, ES cells were cultured and fixed in 8-well slide chambers (BD Biosciences) or 96-well plate wells by 4% paraformaldehyde, permeabilized by 0.1% Triton-X and blocked by 10% bovine fetal serum (GIBCO Invitrogen Corporation) in phosphate-saline buffer (PBS) containing 0.1% Tween-20 (Sigma-Aldrich, St. Louis, www.sigmaaldrich.com) for one hour. Incubation with primary antibody was performed for 1.5 hours at room temperature. Incubation with secondary antibody and 4,6-diamidino-2-phenylindole (DAPI, Molecular Probes) was performed for 40 minutes. Between incubations, the specimens were washed with 0.1% Tween-20 in PBS buffer three to five times. Specimens were preserved in a fluorescence mounting medium (Dako, Glostrup, Denmark, www.dako.com), and observed under a fluorescence microscope (Leica, Heerbrugg, Switzerland, www.leica.com).

Real-Time PCR Quantification of Different mRNAs.

Total RNA was isolated using Absolutely RNA Microprep Kit (Stratagene, La Jolla Calif., www.stratagene.com) according to the manufacturer's instructions. cDNA was synthesized using 0.2 µg of total RNA in 20 µl reaction mixture, containing oligo(dT)12-18 primers and Superscript II reverse transcriptase (GIBCO Invitrogen Corporation), according to the manufacturer's instructions. Real-time quantitative RT-PCR Taqman assays were performed using the Applied Biosystems 7300 Real-Time PCR System (Applied Biosystems, Foster City, Calif.). All reactions were done in quadruplicates with the use of a pre-developed gene expression assay mix (Applied Biosystems) containing primers and a probe for the mRNA of interest. Additional reactions for each experiment included pre-developed gene expression assay mix for GAPDH for normalizing the RNA input. All data was analyzed with 7300 System SDS Software v 1.4.

FACS Analysis.

Cells were removed from the culture dish with Trypsin/EDTA, dissociated into single cell suspension and resuspended in ice-cold FACS buffer (2% fetal bovine serum, 0.1% sodium azide in Hank's buffer). Incubation with primary antibodies against SSEA-4 (from Millipore, Billerica, Mass., www.millipore.com) was performed for one hour on ice. Then, the cells were washed three times with ice-cold FACS buffer. Subsequently, the cells were probed in FACS buffer with 1:400 dilution of Alexa Fluor anti-mouse secondary antibodies (GIBCO Invitrogen Corporation) for 30 minutes in the dark, and washed four times. Control cells were incubated with mouse immunoglobulins and, subsequently, with the secondary antibody as described above. Cells were analyzed on FACSCalibur Flow Cytometer (Becton Dickinson, San Jose, Calif.). Data were analyzed with the CellQuest software (Becton Dickinson).

Karyotyping.

Karyotyping of the cell lines was carried out using standard Q-banding techniques. Samples of cells were treated with colcemid KaryoMAX (0.1 µg/ml; Gibco Invitrogen Corporation) for up to 4 hours, followed by dissociation with Trypsin/EDTA solution (Gibco Invitrogen Corporation). The cells were pelleted via centrifugation and re-suspended in pre-warmed 0.0375 M KCl hypotonic solution and incubated for 10 minutes. Following centrifugation, the cells were resuspended in fixative (3:1 methanol:acetic acid). Metaphase spreads were prepared on glass microscope slides and G-banded by brief exposure to trypsin and stained with 4:1 Gurr's/Leishmann's stain (Sigma-Aldrich Co.). A minimum of 10 metaphase spreads were analyzed and additional 20 were counted.

Teratoma Formation.

Teratoma formation experiments were performed by implantation of approximately $10^6$ cells beneath the testicular capsule of a young (7-week-old) severe combined immunodeficiency (SCID) mouse. Three animals per each cell line were used. Teratoma growth was observed by weekly palpation, and the mice were sacrificed eight weeks after the implantation. The teratomas were fixed, and sections were stained with hematoxylin and eosin (HE) or with hematoxylin, eosin and PAS (HE-PAS). The presence of tissue components of all three embryonic germ line layers was demonstrated, as analyzed from the stained sections. All animal experiments were performed at the infection-free animal facility of the Karolinska University Hospital in accordance with ethical committee approval.

Embryoid Body Formation.

ES cells from LN-521 coated cell culture dishes were exposed to TrypLE™ Select for one minute at 37° C., 5% $CO_2$, washes two times with a medium, broken into large pieces and cultured in suspension in low adhesion plates. The medium used for this was Knockout DMEM (GIBCO Invitrogen Corporation) supplemented with 2 mM L-glutamine, 20% fetal calf serum (GIBCO Invitrogen Corporation), 0.1 mM β-mercaptoethanol (GIBCO Invitrogen Corporation) and 1% non-essential amino acids (GIBCO Invitrogen Corporation). After 1-2 weeks in suspension, the embryoid bodies were transferred onto gelatin coated tissue cell culture 96-well plates (Sarstedt), cultured for 1-2 weeks, then fixed, stained with antibodies against markers of all three embryonic germ line layers (smooth muscle actin, MAP-2 and α-fetoprotein) and analyzed as described above for immunofluorescence.

Cell Adhesion Assay.

Briefly, 96-well plates were coated by extracellular matrix proteins as described above and blocked by O3 medium containing bovine serum albumin. The ES cells were plated at cell density of 50,000 cells/$cm^2$ onto extracellular matrix-coated plates and left to adhere for 1 hour in a cell incubator. After that the plates were washed 3 times with the medium to remove the non-adherent cells, and then the adherent cells were fixed for 20 minutes by 5% glutaraldehyde, stained by 0.1% Crystal Violet. (Kebo Lab, Spanga, Sweden, www.kebolab.se). After one hour and 3 washes with water, Crystal Violet was extracted with 10% acetic acid and quantified by measuring optical density at 570 nm. All the experiments were performed in quadruplicate.

Cell Survival and Inhibition of Survival Assays.

The survival assay was performed as described for the cell adhesion assay above, except that the cells were left in the cell incubator for 24 hours. For inhibition of survival assay, the cells were kept in a medium with function blocking antibodies at the concentrations recommended by the manufacturer or pathway inhibitors at concentrations indicated in the text for 30 minutes, and then plated on the coated dishes. All the experiments were performed in quadruplicate.

Western Blotting and ELISA.

HS 181 cells were trypsinized into single cell suspension as described above. For inhibition experiments, the cells were kept in O3 medium with blocking antibodies or pathway inhibitors for 30 minutes and then 450K cells were plated on 35 mm dishes precoated with the appropriate matrix coating. For other experiments, same number of cells was plated directly after trypsinization. In all cases the cells were allowed to spread for 1 hour at 37° C., 5% $CO_2$. After two washings in ice-cold PBS, the plates with cells were snap frozen in liquid nitrogen and stored at −80° C. To prepare samples for western blots and ELISA, the plates were slowly thawed and kept on ice with 100-150 µl of lysis buffer (50 mM Tris-HCl, pH 7.5, 150 mM NaCl, 0.5% deoxycholate, 0.5% SDS, 1% Triton X-100, 1% Igepal, Complete™ (Roche) and Phospho-Stop™ (Roche)) on top. Then, the cells were scraped, pipetted and sheared through a 27 G ¾" needle. After that, the cell pellets were clarified by centrifugation at 16,100 rcf for 15 minutes at 4° C. For western blots, 4-12% gradient gels were used for SDS electrophoresis and the proteins were transferred to PVDF membranes. The membrane was hybridized with the antibody of interest according to the manufacturer's instructions. Chemoluminescent HRP-substrate from Amersham Biosciences was used for visualization. For the densitometry analysis the films were scanned at 2,400 dpi and analyzed by the ChemiImager5500 program (1D-Multi Line densitometry mode). For ELISA the samples were applied to the wells according to the manufacturer's instructions.

In Vivo Imaging and Migration Assay.

24-well plates were coated by extracellular matrix proteins and blocked by O3 medium containing bovine serum albumin. The ES cells were plated at cell density of 30,000-40,000 cells/$cm^2$ onto extracellular matrix-coated plates and left to adhere for half an hour in a cell incubator. After that, the plate was transferred into high content imaging system Operetta (PerkinElmer) equipped with environmental control unit, which allowed to keep 37° C., 5% $CO_2$. For two movies that were made, the brightfield images were taken once in 15 minutes during 24 hours after plating using Harmony software (PerkinElmer), exported, and analyzed using ImageJ software (NIH, the US). For migration assay the images were taken every seven minutes during 18 hours after plating. Images acquired between the fifth and seventh hours after plating were analyzed using MTrackJ plug-in (University Medical Center, Rotterdam, The Netherlands). 100 attached cells on each coating were traced and mean distances from the current to the previous point of the track were calculated. Error bars show standard error of the mean s.e.m. (n=100).

Statistics. Statistical significance was determined the by Student's two-tailed t-test for unequal variances.

Discussion of Results for Example 2

Pluripotent hES cells express α1, α5, β1, β2 and γ1 laminin chains. To compare the adhesion and clonal survival of hES cells plated from single cell suspension to different coating substrata, hES cells growing as monolayers on LN-511 or as clusters on a feeder layer were trypsinized into single cell suspension in O3 medium and plated on cell culture dishes coated with Matrigel, LN-111, LN-511, LN-521 or a mixture of LN-511 and LN-521, in the absence or presence of a ROCK inhibitor (Y-27632) and analyzed after 24 hours.

The cells did not survive on Matrigel or LN-111, but they did so as single cells on human recombinant LN-511 and LN-521, as well as on the mixture of the two. However, the survival of cells on LN-521 was significantly higher than on LN-511 (compared in numbers below). Cells plated on human recombinant LN-111 or LN-121 failed to survive after 24 hours (data not shown), which demonstrates that the presence of the β2 chain in a laminin trimer, as such, is not sufficient to support the effect. In the presence of ROCK inhibitor Y-27632, the hES cells survived on all surfaces.

There were, however, clear differences with regard to cell shapes between cells growing on LN-521 in the absence or presence of ROCK inhibitor 24 hours after plating. In the absence of ROCK inhibitor 24 hours after plating, cells growing on LN-521 were round, while the cells growing in the presence of ROCK inhibitor adopted spindle or crescent like shape possibly caused by rearrangement of the actin cytoskeleton.

To test if LN-521 could be used as a cell coating material for long-term self-renewal of human pluripotent cells, HS181, HS401, H1 cells and human iPS ChiPSW and CutB1.2 cells were cultured on the protein in O3, mTeSR1 or TeSR2 media. Cells growing in O3 or TeSR1 media were passed in single cell suspension every 10-14 days at ratios of 1:20-1:30. Pluripotent hES cells proliferated at a stable rate similar or higher to that of cells grown on LN-511 or Matrigel when passed in small clumps. Thus, one passage on LN-521 yielded the same or higher number of cell divisions than that of control cells passed twice in clumps. HS181, HS401, and H1 cells proliferated for at least 24, 5 and 15 passages, respectively (9, 2 and 6 months) in an O3 medium. CutB1.2 iPS and ChiPSW cells have been cultured for 5 and 3 passages in mTeSR1, respectively. Interestingly, dissociated hES cells could be cultured on LN-521 under completely defined and xeno-free conditions, using TeSR2 medium and TrypLE Select enzyme. The plating efficacy after a passage was slightly lower than that of the cells in O3 or mTeSR1 media, and the dissociated cells were passed normally every 10-14 days in 1:15-1:20 ratios. H1 and HS401 cells have been cultured for 12 and 4 passages, respectively (5 and 1.5 months) in TeSR2.

The hES cells were usually plated in single cell suspension at 30,000 cells per 1 cm² of culture dish coated with LN-521, after which individual cells lacked any direct contacts with each other. Eight hours after plating, the hES cells could be observed as single cells expressing pluripotency markers Oct4, Nanog, and Sox2. Twenty-four hours after plating, the cells formed small monolayer colonies that eventually combined into large islands of monolayers covering most of the well.

Cells grown on LN-521 showed stable expression levels of pluripotency markers Oct4, Nanog, and SSEA4, which were similar to those in cells plated on Matrigel and passed as small clumps. To compare the level of spontaneous differentiation in LN-521 and Matrigel cultures, the amount of mRNAs for differentiation markers PAX6, SOX17 and SOX7 expressed in Matrigel cultures and in LN-521 cultures were compared after one (10 days) and 10 passages (4 months). Quantitative RT-PCR revealed similar or less levels of expression of all three markers of differentiation in LN-521 cultures independently on the passage number.

Karyotypes were confirmed to be normal for hES cell lines HS181 and H1 after 12 and 10 passages, respectively, on LN-521 in the O3 medium; and for H1 after 7 passages in TeSR2 medium. Histological examination of teratomas formed in SCID mice after injection of HS181 and H1 cells cultured for 13 and 12 passages, respectively, on LN-521 in O3 medium, and H1 cells cultured for 7 passages on LN-521 in TeSR2 revealed development of tissues containing all three germ lineages of the human embryo. Differentiation in vitro also revealed, that the cells in all three cases retained the competence to form embryoid bodies expressing markers of mesoderm (smooth-muscle actin), ectoderm (MAP-2) and endoderm (α-fetoprotein).

To quantify the efficacy of the coating substrata, adhesion after one hour and survival after 24 hours of dissociated hES cells on Matrigel, LN-111, LN-511, LN-521, and an equal mixture of LN-511 and LN-521 were studied. Interestingly, after one hour about the same 75-80% of cells had adhered to all the coatings, although the spreading of the cells was clearly better on LN-521 and LN-511 than on Matrigel or LN-111 (not shown). After 24 hours, almost no cells had survived on Matrigel or LN-111, and very few on LN-511. In contrast, the survival of hES cells on LN-521 was approximately 20 times higher than on Matrigel, and three times higher than on LN-511.

To qualitatively compare the effects of LN-521 and ROCK inhibitor (Y-27632), we plated cells from the same single cell suspension at the same plating density (40,000 cells per 1 cm²) in a medium containing 10 μM of Y-27632 and studied their survival on the different coatings. The untreated cells on LN-521 and Y-27632 treated cells on Matrigel showed similar survival rate 24 hours after plating. Interestingly, even Y-27632 treated human ES cells survived better on LN-521 than on Matrigel.

If exogenous bFGF was removed from the O3 medium, the cells still showed 20 times higher survival on LN-521 than on Matrigel. Moreover, hES cells survived on LN-521 24 hours after plating, even in a medium lacking all the growth factors of the TeSR1 formulation (bFGF, LiCl, γ-aminobutyric acid (GABA), pipecolic acid and TGFβ)[16], suggesting that the survival mechanism is independent of signaling induced by those factors.

An assay for inhibition of cell survival using function-blocking antibodies to potential receptors for LN-521 on the plasma membrane showed that antibodies to integrins α6, and to a slightly lesser extent to β1, inhibited survival of human ES cells on LN-521. Function-blocking antibodies to other tested integrin subunits, as well as to Lutheran receptor and α-dystroglycan, showed very little if any effects on human ES cell survival on LN-521.

Figure 12:
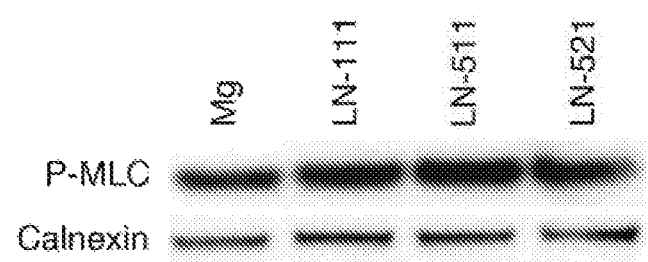
FIG. 12 is a Western blot comparing the levels of phosphorylated myosin light chain (P-MLC) in stem cells grown on Matrigel (Mg), LN-111, LN-511, and LN-521 one hour after plating.
Figure 13:
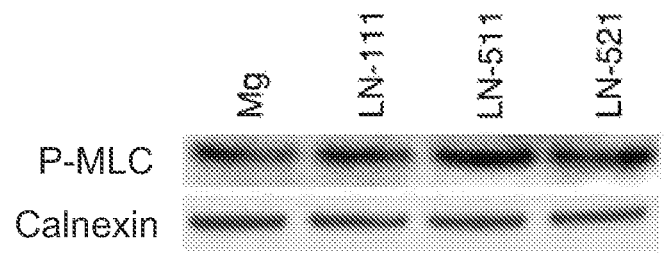
FIG. 13 is a Western blot comparing the levels of phosphorylated myosin light chain (P-MLC) in stem cells grown on Matrigel (Mg), LN-111, LN-511, and LN-521 six hours after plating.
Figure 14:
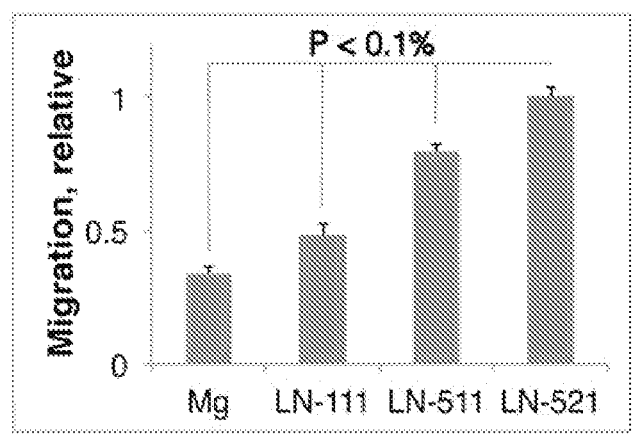
FIG. 14 is a graph comparing the relative migration of human embryonic stem cells grown on Matrigel (Mg), LN-111, LN-511, and LN-521 between five and seven hours after plating.
Figure 15:
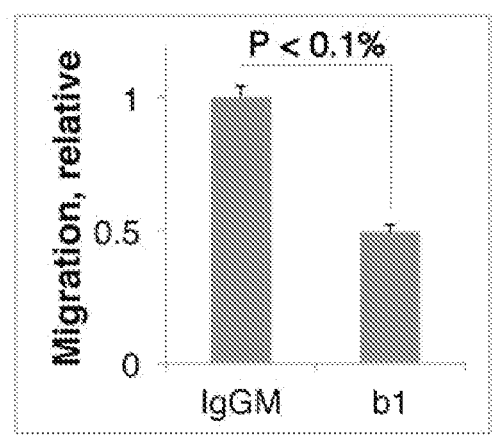
FIG. 15 is a graph comparing the relative migration of human embryonic stem cells grown on LN-521 with IgG and IgM blocking antibodies applied (IgGM) and with a function blocking antibody to integrin β1 (b1) applied. This shows that blocking the integrin significantly reduced motility.

Recently, it has been shown that ROCK inhibitors and blebbistatin act through abrogation of actin-myosin contractility, which is mediated by phosphorylation of the myosin light chain (MLC). To test if LN-521 had similar activity, levels of phosphorylated MLC were compared between the dissociated cells on Matrigel, LN-111, LN-511, and LN-521 one and six hours after plating (FIG. 12 and FIG. 13). Interestingly, western blot showed that phosphorylation of MLC was even higher in the cells on LN-511 and LN-521 than that in the cells on Matrigel and LN-111. Since actin-myosin rearrangements are essential not only for contractions, but also for cell motility, we surmised that the cell migration could be caused by interaction between LN-521 and its integrin receptor α6β1. In vivo imaging of the cells on Matrigel and LN-521 revealed that the cells migrated much faster on the latter and survived by aggregation into small fast moving colonies. Migration of hES cells on the four coatings was also compared between the fifth and seventh hours after plating when the cells were still attached in all cases (FIG. 14). Motility of the hES cells on LN-521 was higher than that of the cells on other coatings and correlated with the ability to survive on them. Treatment with function blocking antibody to integrin β1 significantly reduced motility (FIG. 15) and adhesion (data not shown) of the cells on LN-521.

Figure 16:
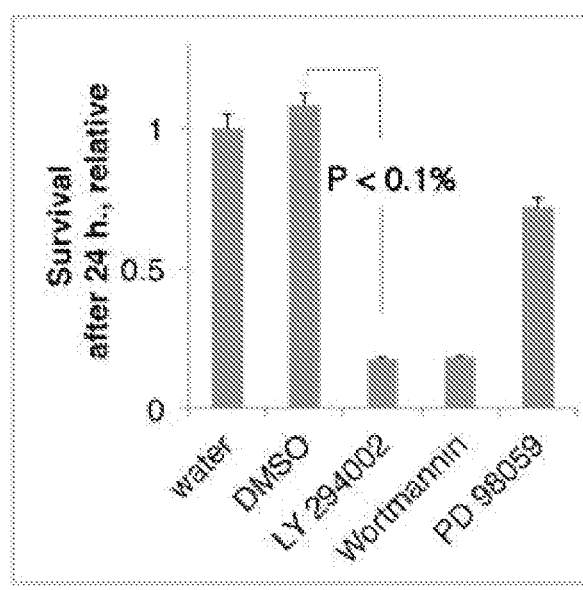
FIG. 16 is a graph comparing the relative survival of hES cells on LN-521 in the presence of water, DMSO, LY294002 (Akt inhibitor), wortmannin (PI3K/Akt inhibitor), and PD 98059 (MEK1 inhibitor). This showed that activation of PI3K/Akt was necessary for hES cell survival on LN-521. The medium contained bFGF.

An extensive body of data has shown that activation of the MEK1/Erk or PI3-kinase/Akt pathways by integrins can block anoikis. The effects of LY 294002 and PD 98059, specific inhibitors of Akt and MEK1, respectively, were examined to explore the potential role of these pathways in hES cell survival on LN-521. Blockade of Akt activation by LY 294002 was found to facilitate detachment and hES cell death, with no cells surviving 24 hours after plating on LN-521 (FIG. 16). In contrast, treatment with PD 98059 did not affect the survival that severely. hES cells treated with another PI3K/Akt specific inhibitor, Wortmannin, also failed to survive 24 hours after plating on LN-521, confirming that activation of PI3K/Akt was necessary for the cell survival on LN-521.

Figure 17:
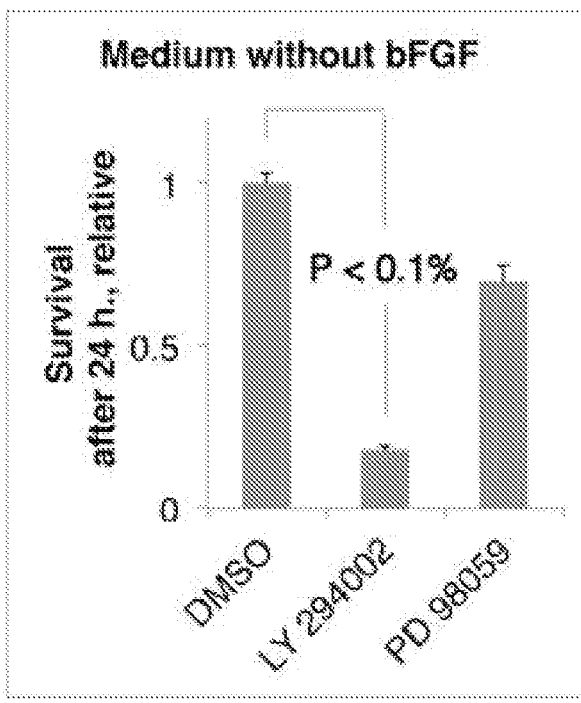
FIG. 17 is a graph comparing the relative survival of hES cells on LN-521 in the presence of DMSO, LY294002 (Akt inhibitor), and PD 98059 (MEK1 inhibitor). No exogenous bFGF was present.
Figure 18:
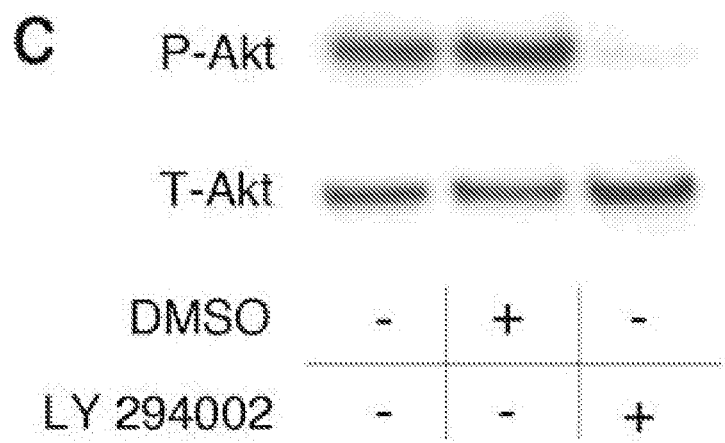
FIG. 18 is a Western blot comparing cells treated with LY 294002 against control cells (DMSO) and collected one hour after plating on LN-521.
Figure 19:
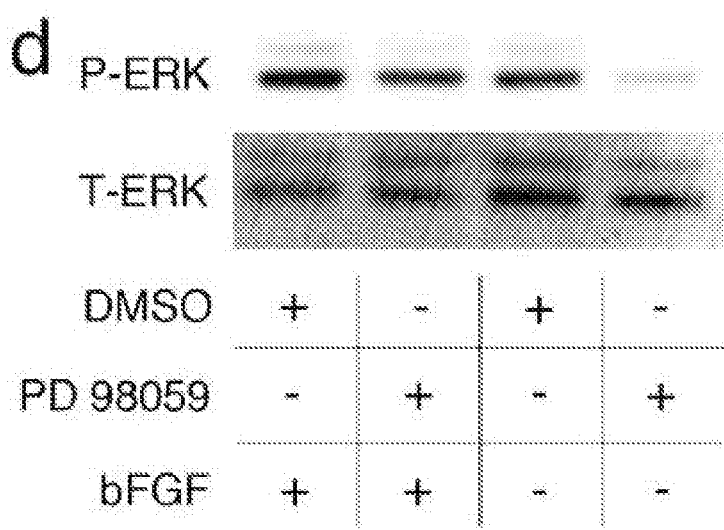
FIG. 19 is a Western blot comparing cells treated with PD98059 against control cells (DMSO) and collected one hour after plating on LN-521.

Since bFGF is known to be a potent activator of the MEK1/Erk pathway, the influence of which cannot be fully inhibited by PD 98059, we performed the same experiment in O3 medium without exogenous bFGF with the same result (FIG. 17). The efficacy of LY 294002 and PD 98059 treatment was confirmed by western blot analysis of the treated and control cells collected one hour after plating on LN-521 (FIG. 18 and FIG. 19).

Figure 20:
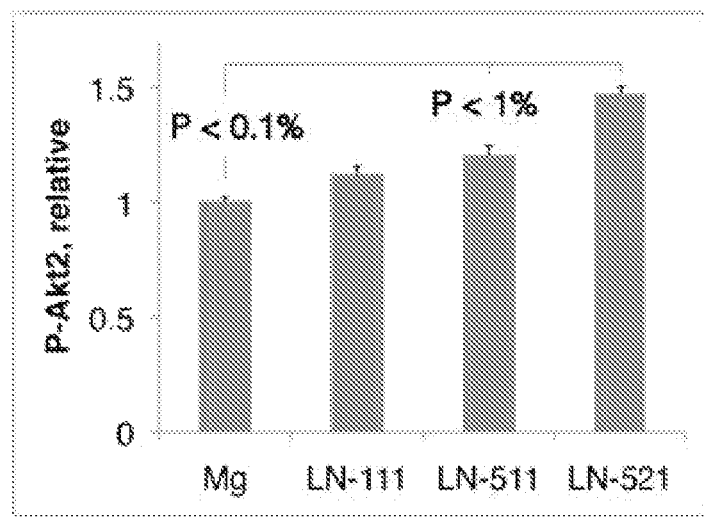
FIG. 20 is a graph showing the relative levels of Akt2 phosphorylation on cell lysates collected one hour after plating on Matrigel (Mg), LN-111, LN-511, or LN-521, obtained using ELISA.
Figure 21:
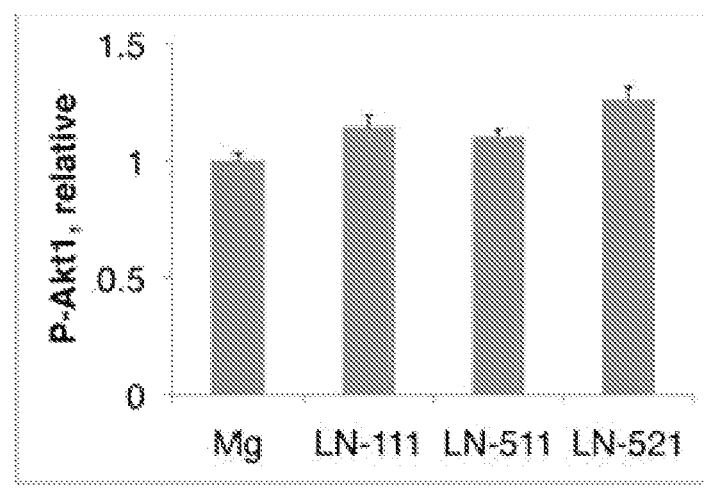
FIG. 21 is a graph showing the relative levels of Akt1 phosphorylation on cell lysates collected one hour after plating on Matrigel (Mg), LN-111, LN-511, or LN-521, obtained using ELISA.

Western blot analysis of extracts of cells growing on Matrigel and LN-521 with antibodies to phospho-Akt showed that the PI3K/Akt pathway was active in both cases (data not shown). To determine the levels of Akt activation in the cells on different coating, ELISA was performed on cell lysates collected one hour after plating on Matrigel, LN-111, LN-511 and LN-521 when the cells still did not have direct contacts with each other (FIG. 20 and FIG. 21). The level of Akt2 phosphorylation in the cells on different coatings correlated with survivability on them.

It has been demonstrated that α6 and β1 integrins are the most abundantly expressed integrin isoforms in human ES cells among alpha and beta subunits respectively. Integrin α6β1 shows a broad spectrum of specificity towards different laminins, but the binding affinity for LN-521 or LN-511 is higher than that for LN-111. Recently, it has been established that β2 laminins have higher affinity for integrins than the β1 laminins. Therefore, having the highest affinity for the integrin, LN-521 can provide the best anchorage for migration and can convey the highest dose of signal via α6β1 integrin resulting in the best survivability of dissociated pluripotent hES cells, although e.g. LN-511 also can do it at a lesser extent.

The results of this work may facilitate culturing and expansion of pluripotent human stem cells in general, and even make automated expansion of such cells possible including cells aimed for clinical applications. The survival of dissociated hES cells on LN-521 appears to be dependent on migration and the cells can therefore not survive after plating at ultralow densities. The new hES cell culture method described here utilizes only a naturally occurring LN-521 adhesion protein that does not damage the cytoskeleton as ROCK inhibitor or blebbistatin treatment do. Thus, LN-521 most probably favors survival of the cells only with the correct integrin profile on the cell surface. The present results also showed that hES cells plated on LN-521 at relatively low densities of 20,000-30,000 cells per 1 cm$^2$ could survive and multiply at least as efficiently as in the other hES culture systems. The new method closely resembles standard cell culture procedures, e.g. culturing of fibroblasts, and, therefore, hES cell cultures on LN-521 do not demand specially trained personnel, which has been a major problem before since culturing of hES cells has been a technological challenge.

The widely used TeSR1 formulation for human pluripotent stem cell self-renewal was initially developed for use with Matrigel and it contains high doses of bFGF that mostly targets the MEK1/Erk pathway, which is not widely considered to have a beneficial effect for pluripotent hES cells. The present results can lead to development of new medium formulations utilizing benefits of LN-521 as coating material and specifically targeting pathways, which are important for human ES cell self-renewal.

In summary, the present work has demonstrated that LN-521, normally secreted by pluripotent hES, can as a sole coating material support self-renewal of human pluripotent stem cells in culture, similar to LN-511. Both laminins facilitated growth of the cells as homogenous monolayers in vitro. However, an important difference between the two laminins is that hES/hiPS cells could be trypsinized into single cell suspension, and plated and effectively expanded from single cells on LN-521, as opposed to manual splitting of cell clusters, as is currently required for expansion of hES/iPS cells grown on Matrigel or feeder cells. The results of this work may facilitate culturing of pluripotent human stem cells and facilitate automated expansion of such cells.

Example 3

Human embryonic stem cells were cultured upon a laminin-521 substrate in two different cell culture mediums. The two cell culture mediums differed in the amount of bFGF, 3.9 ng/ml and 100 ng/ml.

Figure 22:
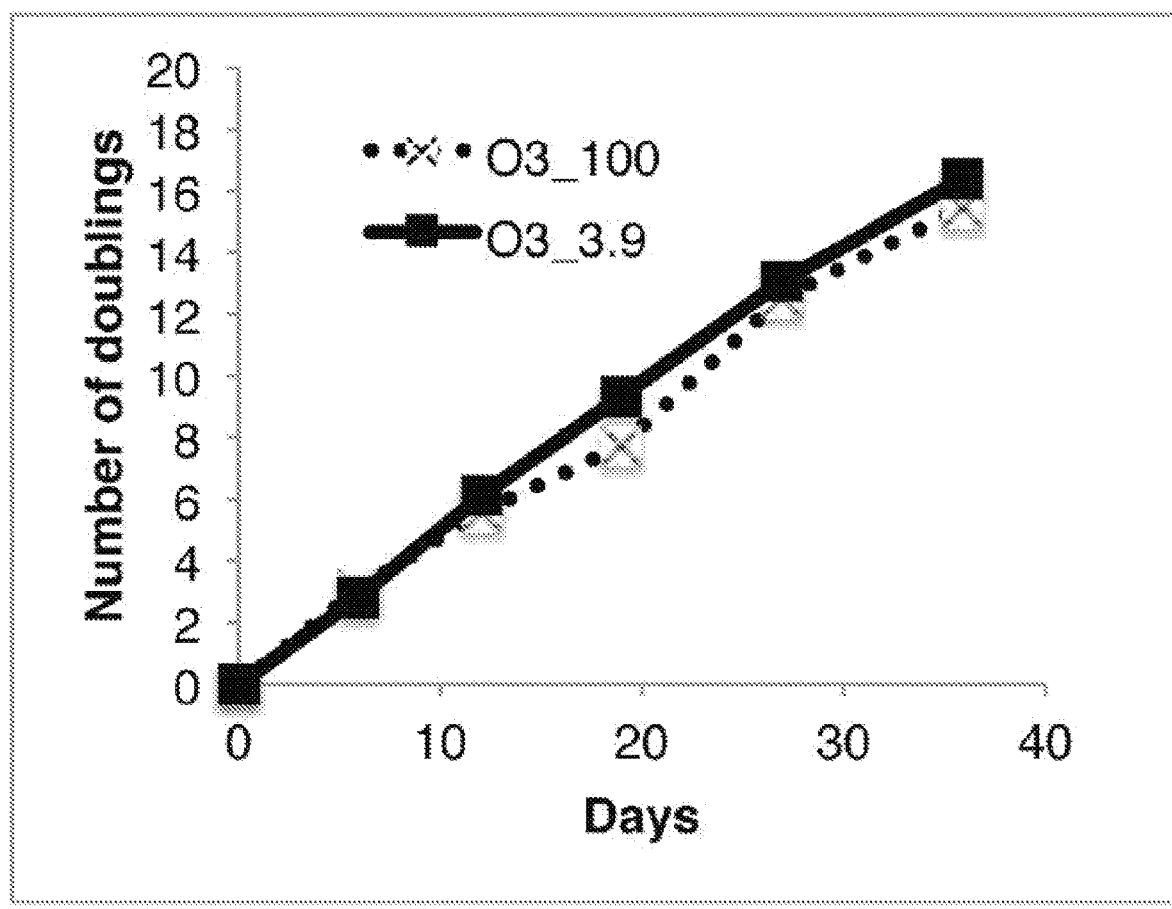
FIG. 22 is a graph showing the growth curve of HS181 hES cells cultured in a low bFGF medium (O3_3.9) compared to a higher bFGF medium (O3_100).

FIG. 22 shows the growth curve of HS181 hES cells cultured in an O3 medium comprising 3.9 ng/mL of bFGF with a laminin-521 substrate after 5 passages (40 days) in solid black. The O3 medium was a variant of the commercially available chemically defined mTeSR1 medium with bovine serum albumin as the only animal derived component. The growth curve of HS181 hES cells cultured in an O3 medium comprising 100 ng/mL of bFGF with a laminin-521 substrate is shown in dashes. The cells were dissociated into single cell suspension for passaging. As seen here, the growth curve for the lower amount of bFGF was as good as or better than the higher amount of bFGF.

Figure 23:
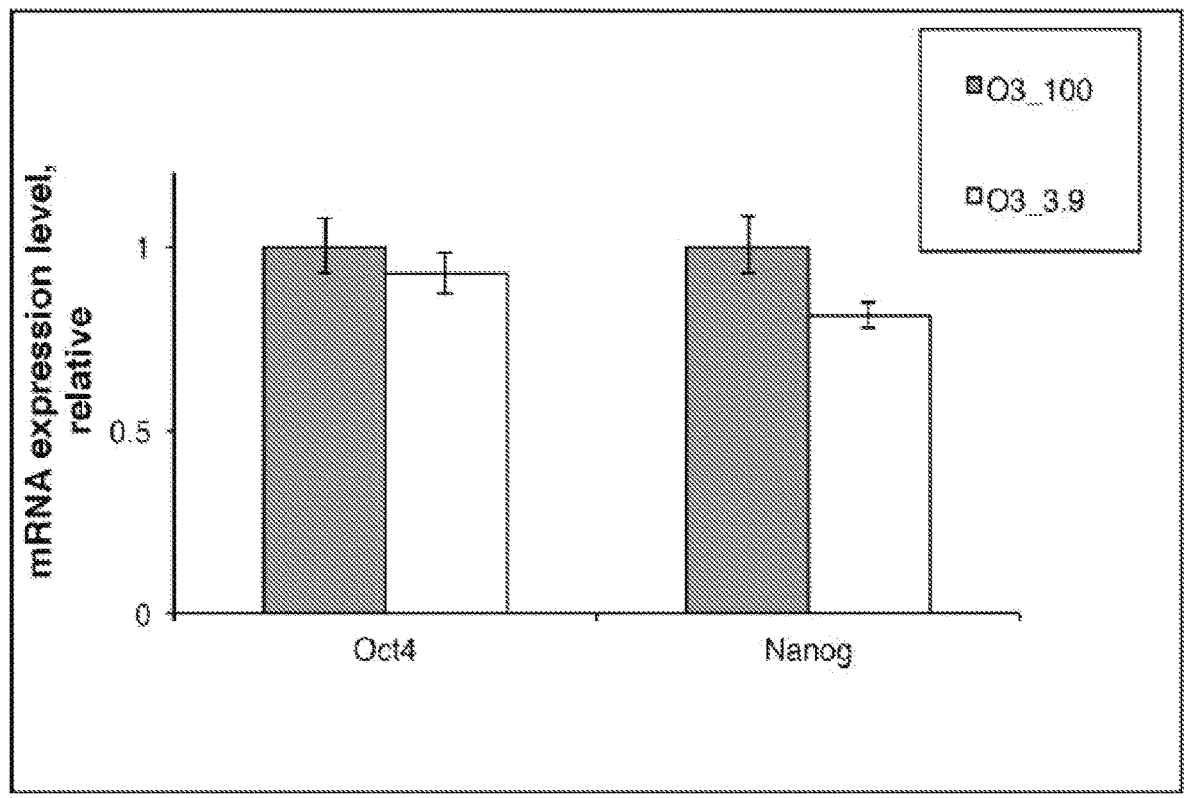
FIG. 23 is a graph showing the relative mRNA expression level for two pluripotency markers (Oct4 and Nanog) in HS181 hES cells cultured in a low bFGF medium (O3_3.9) compared to a higher bFGF medium (O3_100).

FIG. 23 shows the relative amount of mRNA transcripts for pluripotency markers Oct4 and Nanog after 5 passages (40 days) for both media, which was obtained using real-time quantitative reverse transcription polymerase chain reaction (RT-PCR) analysis. Again, similar amounts were obtained in both cell culture mediums, indicating that the stem cells in the lower amount of bFGF maintained pluripotency. Thus, a lower amount of bFGF can be used and still obtain good results, particularly in combination with the laminin-521 substrate.

Example 4

In Examples 1 and 2, the dissociated stem cells survived mostly through active motility on LN-521 and association into small effectively growing and migrating monolayer islands. The cells plated at very low, cloning densities died through anoikis, a specialized form of programmed cell death. Normally, integrin-related signaling from extracellular matrix molecules, e.g. laminins, and cadherin-related cell-cell signaling, can prevent anoikis. The most abundant cadherin isoform on the human ES cell surface is epithelial-cadherin (E-Cadherin). The experiments in Examples 3 were performed to find out if a combination of LN-521 and E-Cadherin could protect human ES cells from anoikis and allow clonal survival of the cells.

hES cells were plated in mTeSR1 medium on different coatings at a density of 250 cells per cm$^2$ and monitored after 5 days in culture using an alkaline phosphatase staining kit. Neither laminin-521 nor E-Cadherin alone permitted efficient clonal survival of individualized hES cells.

Next, combinations of laminin-521 and E-Cadherin were tested to determine whether the combinations could sustain clonal survival of the cells. Fixed amounts of laminin-521 were used for the cell culture dish coating in combination with titrated E-Cadherin. Clonal survival of cells was achieved at different ratios of E-Cadherin to laminin-521 including from about 1:10 w/w to about 1:5 w/w.

Additional tests were performed to test the effects of various modifications to the mTeSR1 medium. A mixture of E-Cadherin to laminin-521 in a ratio of about 1:10 w/w was used to coat the plates. Unexpectedly, it was discovered that a 2× increase in albumin concentration significantly improved clonal survival of hES cells on the laminin-521/E-Cadherin matrix. The rate of individualized hES cell survival under these conditions was from 10 to 15% and was at least one order of magnitude higher than that of the cells on Matrigel, laminin-521, or E-Cadherin alone in both mTeSR1 medium and mTeSR1 medium with additional albumin. Time-lapse photography of the cells confirmed that laminin-521/E-Cadherin coatings facilitated cell survival through proliferation of the single cells, not through the aggregation of different cells. Laminin-521/E-Cadherin similarly sustained clonal survival of cells in completely chemically defined and xeno-free TeSR2 medium with the addition of recombinant human serum albumin (rHSA).

In additional testing, hES cell lines were derived. Twenty-four well tissue cell culture dish plates were washed twice with Dulbecco's Phosphate Buffered Saline. Next, the dish plates were coated for 2 hours at 37° C. with sterile solution containing: 48 μL of 100 μg/mL laminin-521 (BioLamina AB, Stockholm); 6 μL of 82 μg/mL E-Cadherin (R@DSystems); and 300 μL of DPBS with calcium and magnesium (GIBCO) to produce a laminin-521/E-Cadherin matrix.

The donated embryos used to derive the hES cell lines were obtained from an accredited in vitro fertilization clinic after the consent of both partners and ethics approval were obtained. Only fresh or frozen embryos, which could not be used for infertility treatment, were used in the derivation procedures. One or two cells were isolated from an 8-cell stage embryo using a micropipette after making a small opening to the zona pellucida with a laser apparatus designed for this purpose. The cells were placed on the laminin-521/E-Cadherin matrix in TeSR2 medium with additional rHSA. The cells successfully attached and started to proliferate. The parental embryos were allowed to grow to a blastocyst stage and frozen. The embryo culture was carried out using xeno-free standardized in vitro fertilization culture media in drops under oil at 37° C. and 5% $O_2$/10% $CO_2$. After removal of the zona pellucida, the inner cell masses of five human blastocysts were mechanically isolated and plated in 4-well culture plates (Nunc) onto the laminin-521/E-Cadherin matrix. Following an initial 48 hours of culture, the culture medium was replaced on a daily basis. After 10 to 14 days, the outgrowths were mechanically isolated and replated onto laminin-521/E-Cadherin matrix. Mechanical passaging was used for the subsequent 2 to 3 passages after which colonies were passaged using TrypLE Select (GIBCO).

Figure 24:
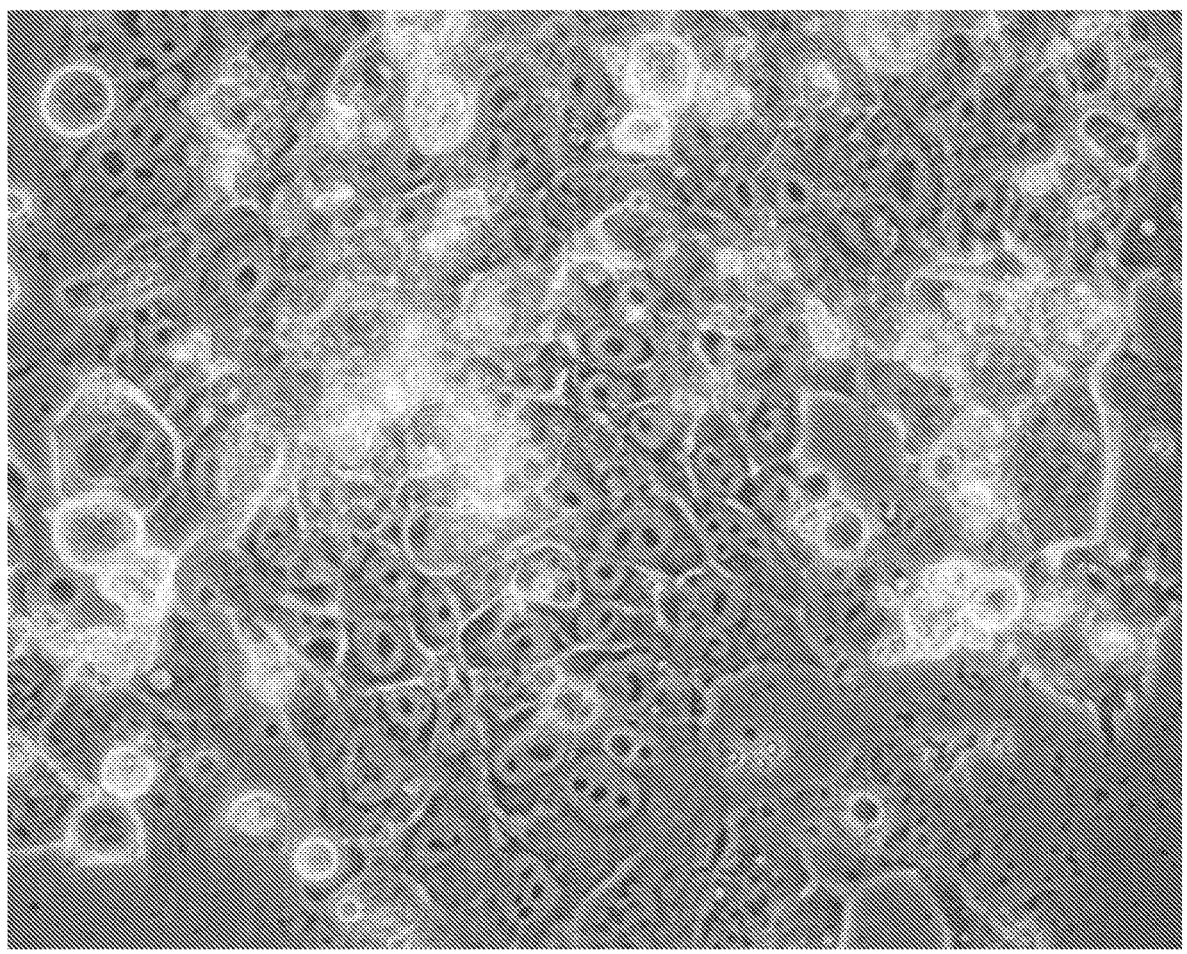
FIG. 24 is a picture showing an early stage derivation of a new human embryonic stem HS841 cell line on laminin-521/E-Cadherin matrix.

Using the laminin-521/E-Cadherin matrix described above with the mTeSR1 medium including additional bovine albumin, three new hES cell lines were derived from six cultured blastocysts. Four days after plating, the inner cell masses gave stem cell-like outgrowths. FIG. 24 shows an early stage derivation of a new human embryonic stem HS841 cell line on laminin-521/E-Cadherin matrix. Morphologically typical human embryonic stem cells growing out from the inner cell mass of a day six blastocyst four days after mechanical isolation of the inner cell mass and plating on laminin-521/E-Cadherin matrix are shown.

Unexpectedly, the cell culture system and method gave stable, hES cell lines in 3 out of 6 embryos (50%), a derivation rate higher than that of standard methods.

The use of a laminin-521/E-Cadherin matrix and TeSR2 medium with additional rHSA, a completely chemically defined and xeno-free environment, yielded similar results in the derivation of new hES cell lines.

Table 5 below provides the formulation for the mTeSR1 medium used in this Example. The amounts of each ingredient can vary by up to 20%.

In particular embodiments, the amount of human serum albumin (HSA) can be varied from a concentration of 0.195 mM to 1 mM, including from 0.3 mM to 1 mM or from 0.3 mM to about 0.4 mM. The amount of bFGF can also be varied from 0 to about 105 ng/mL, or from 0 to 3.9 ng/mL, or from 0.5 ng/mL to 3.5 ng/mL. These two variations in the amount of HSA and bFGF may occur independently or together.

TABLE 5 mTeSR1 formulation.

| mTeSR1 Ingredient | molar mass (g/mol) | Concentration (ng/mL) | Concentration (mM) |
|---|---|---|---|
| INORGANIC SALTS | | | |
| Calcium chloride (Anhydrous) | 110.98 | 9.14E+04 | 8.24E−01 |
| HEPES | 238.3 | 2.81E+06 | 1.18E+01 |
| Lithium Chloride (LiCl) | 42.39 | 4.15E+04 | 9.80E−01 |
| Magnesium chloride (Anhydrous) | 95.21 | 2.26E+04 | 2.37E−01 |
| Magnesium Sulfate ($MgSO_4$) | 120.37 | 3.84E+04 | 3.19E−01 |
| Potassium chloride (KCl) | 74.55 | 2.43E+05 | 3.26E+00 |
| Sodium bicarbonate ($NaHCO_3$) | 84.01 | 1.51E+06 | 1.80E+01 |
| Sodium chloride (NaCl) | 58.44 | 5.53E+06 | 9.46E+01 |
| Sodium phosphate, dibasic (Anhydrous) | 141.96 | 5.56E+04 | 3.92E−01 |
| Sodium phosphate, monobasic monohydrate ($NaH_2PO_4$—$H_2O$) | 137.99 | 4.90E+04 | 3.55E−01 |
| TRACE MINERALS | | | |
| Ferric Nitrate ($Fe(NO_3)_3$—$9H_2O$) | 404 | 3.92E+01 | 9.71E−05 |
| Ferrous sulfate heptahydrate ($FeSO_4$—$7H_2O$) | 278.01 | 3.28E+02 | 1.18E−03 |
| Copper(II) sulfate pentahydrate ($CuSO_4$—$5H_2O$) | 249.69 | 1.02E+00 | 4.08E−06 |
| Zinc sulfate heptahydrate ($ZnSO_4$—$7H_2O$) | 287.56 | 3.39E+02 | 1.18E−03 |
| Ammonium Metavanadate $NH_4VO_3$ | 116.98 | 1.28E+00 | 1.09E−05 |
| Manganese Sulfate monohydrate ($MnSO_4$—$H_2O$) | 169.02 | 3.33E−01 | 1.97E−06 |
| $NiSO_4$—$6H_2O$ | 262.85 | 2.55E−01 | 9.70E−07 |
| Selenium | 78.96 | 1.40E+01 | 1.77E−04 |
| Sodium Meta Silicate $Na_2SiO_3$ $9H_2O$ | 284.2 | 2.75E+02 | 9.66E−04 |
| $SnCl_2$ | 189.62 | 2.35E−01 | 1.24E−06 |
| Molybdic Acid, Ammonium salt | 1235.86 | 2.43E+00 | 1.97E−06 |
| $CdCl_2$ | 183.32 | 2.24E+00 | 1.22E−05 |
| $CrCl_3$ | 158.36 | 3.14E−01 | 1.98E−06 |
| $AgNO_3$ | 169.87 | 1.67E−01 | 9.81E−07 |
| $AlCl_3$ $6H_2O$ | 241.43 | 1.18E+00 | 4.87E−06 |
| Barium Acetate ($Ba(C_2H_3O_2)_2$) | 255.42 | 2.50E+00 | 9.79E−06 |
| $CoCl_2$ $6H_2O$ | 237.93 | 2.33E+00 | 9.81E−06 |
| $GeO_2$ | 104.64 | 5.20E−01 | 4.97E−06 |
| KBr | 119 | 1.18E−01 | 9.89E−07 |
| KI | 166 | 1.66E−01 | 1.00E−06 |
| NaF | 41.99 | 4.13E+00 | 9.83E−05 |
| RbCl | 120.92 | 1.19E+00 | 9.81E−06 |
| $ZrOCl_2$ $8H_2O$ | 178.13 | 1.75E+00 | 9.80E−06 |
| ENERGY SUBSTRATES | | | |
| D-Glucose | 180.16 | 2.47E+06 | 1.37E+01 |
| Sodium Pyruvate | 110.04 | 4.31E+04 | 3.92E−01 |
| LIPIDS | | | |
| Linoleic Acid | 280.45 | 5.27E+01 | 1.88E−04 |
| Lipoic Acid | 206.33 | 8.25E+01 | 4.00E−04 |
| Arachidonic Acid | 304.47 | 3.93E+00 | 1.29E−05 |
| Cholesterol | 386.65 | 4.33E+02 | 1.12E−03 |
| DL-alpha tocopherol-acetate | 472.74 | 1.37E+02 | 2.90E−04 |
| Linolenic Acid | 278.43 | 1.95E+01 | 6.99E−05 |
| Myristic Acid | 228.37 | 1.96E+01 | 8.59E−05 |
| Oleic Acid | 282.46 | 1.96E+01 | 6.94E−05 |
| Palmitic Acid | 256.42 | 1.96E+01 | 7.65E−05 |
| Palmitoleic acid | 254.408 | 1.96E+01 | 7.71E−05 |
| Stearic Acid | 284.48 | 1.96E+01 | 6.89E−05 |

TABLE 5-continued mTeSR1 formulation.

| mTeSR1 Ingredient | molar mass (g/mol) | Concentration (ng/mL) | Concentration (mM) |
|---|---|---|---|
| AMINO ACIDS | | | |
| L-Alanine | 89.09 | 1.22E+04 | 1.37E-01 |
| L-Arginine hydrochloride | 147.2 | 8.07E+04 | 5.48E-01 |
| L-Asparagine-H$_2$O | 150.13 | 2.06E+04 | 1.37E-01 |
| L-Aspartic acid | 133.1 | 1.82E+04 | 1.37E-01 |
| L-Cysteine-HCl—H$_2$O | 175.63 | 1.38E+04 | 7.83E-02 |
| L-Cystine dihydrochloride | 313.22 | 2.45E+04 | 7.83E-02 |
| L-Glutamic acid | 147.13 | 2.02E+04 | 1.37E-01 |
| L-Glutamine | 146.15 | 4.30E+05 | 2.94E+00 |
| Glycine | 75.07 | 2.21E+04 | 2.94E-01 |
| L-Histidine monohydrochloride monohydrate | 209.63 | 2.47E+04 | 1.18E-01 |
| L-Isoleucine | 131.17 | 4.28E+04 | 3.26E-01 |
| L-Leucine | 131.17 | 4.64E+04 | 3.54E-01 |
| L-Lysine hydrochloride | 182.65 | 7.14E+04 | 3.91E-01 |
| L-Methionine | 149.21 | 1.35E+04 | 9.06E-02 |
| L-Phenylalanine | 165.19 | 2.79E+04 | 1.69E-01 |
| L-Proline | 115.13 | 2.49E+04 | 2.16E-01 |
| L-Serine | 105.09 | 3.09E+04 | 2.94E-01 |
| L-Threonine | 119.12 | 4.19E+04 | 3.52E-01 |
| L-Tryptophan | 204.23 | 7.07E+03 | 3.46E-02 |
| L-Tyrosine disodium salt hydrate | 225.15 | 3.78E+04 | 1.68E-01 |
| L-Valine | 117.15 | 4.16E+04 | 3.55E-01 |
| VITAMINS | | | |
| Ascorbic acid | 176.12 | 4.46E+04 | 2.53E-01 |
| Biotin | 244.31 | 2.74E+00 | 1.12E-05 |
| B12 | 1355.37 | 5.34E+02 | 3.94E-04 |
| Choline chloride | 139.62 | 7.02E+03 | 5.03E-02 |
| D-Calcium pantothenate | 238.27 | 8.79E+02 | 3.69E-03 |
| Folic acid | 441.4 | 2.08E+03 | 4.71E-03 |
| i-Inositol | 180.16 | 9.89E+03 | 5.49E-02 |
| Niacinamide | 122.12 | 1.59E+03 | 1.30E-02 |
| Pyridoxine hydrochloride | 205.64 | 1.57E+03 | 7.62E-03 |
| Riboflavin | 376.36 | 1.72E+02 | 4.56E-04 |
| Thiamine hydrochloride | 337.27 | 8.16E+03 | 2.42E-02 |
| GROWTH FACTORS/PROTEINS | | | |
| GABA | 103.12 | 1.01E+05 | 9.79E-01 |
| Pipecolic Acid | 129 | 1.27E+02 | 9.84E-04 |
| bFGF | 18000 | 1.04E+02 | 5.77E-06 |
| TGF beta 1 | 25000 | 5.88E-01 | 2.35E-08 |
| Human Insulin | 5808 | 2.28E+04 | 3.92E-03 |
| Human Holo-Transferrin | 78500 | 1.08E+04 | 1.37E-04 |
| Human Serum Albumin | 67000 | 1.31E+07 | 1.95E-01 |
| Glutathione (reduced) | 307.32 | 1.96E+03 | 6.38E-03 |
| OTHER COMPONENTS | | | |
| Hypoxanthine Na | 136.11 | 1.61E+03 | 1.18E-02 |
| Phenol red | 354.38 | 5.99E+03 | 1.69E-02 |
| Putrescine-2HCl | 161.07 | 6.36E+01 | 3.95E-04 |
| Thymidine | 242.229 | 2.86E+02 | 1.18E-03 |
| 2-mercaptoethanol | 78.13 | 7.66E+03 | 9.80E-02 |
| Pluronic F-68 | 8400 | 1.96E+05 | 2.33E-02 |
| Tween 80 | 1310 | 4.31E+02 | 3.29E-04 |

The systems containing a LN-521/e-cadherin substrate and mTeSR1 medium with additional albumin work extremely well for maintaining and proliferating undifferentiated stem cells (e.g. embryonic and induced pluripotent stem cells) in a completely chemically defined environment and xeno-free conditions without feeders or any inhibitors of apoptosis.

In this context, LN-521 and LN-511 can be used in a substrate combined with e-cadherin. The LN-521/LN-511 may be present as an intact protein or as a protein fragment. Again, a "fragment" contains one, two, or three functional domains that possesses binding activity to another molecule or receptor. Generally, any effective laminin may be used, wherein the effectiveness is determined by whether stem cells can proliferate upon the substrate. The laminins are usually recombinant as well.

Additionally, systems containing a laminin substrate and cell culture medium can be used to make new retinal pigment epithelium (RPE) cells. In this regard, impairment of vision is a major reason for severe morbidity. Age-related macular degeneration (AMD) is a medical condition which results in a loss of vision in the center of the visual field (the macula) because of damage to the retina. Age-related macular degeneration begins with characteristic yellow deposits (drusen) in the macula, between the retinal pigment epithelium and the underlying choroid. In the "dry" form of advanced AMD the retinal pigment epithelial layer below the retina atrophies, which causes vision loss through loss of photoreceptors (rods and cones) in the central part of the eye.

AMD is the most common cause of severe vision loss in the Western world with an economic burden on the health care system exceeding that of stroke. In Europe and North America alone, more than 5 million people suffer from end-stage AMD (i.e. neovascular or geographic atrophy) with an incidence of almost 500,000 individuals per year. The prevalence is further expected to increase by 75% in 2040. Moreover, impaired vision is associated with several significant co-morbidities such as fragility fractures in the aging population, causing an enormous burden on health and society resources.

The RPE is the pigmented cell layer just outside the neurosensory retina that nourishes retinal visual cells, and is firmly attached to the underlying choroid and overlying retinal visual cells. This single RPE cell layer is essential for normal neuroretinal and choroidal function. For example, the RPE phagocytoses (digests) the photoreceptor outer segments, thus maintaining normal cell turnover. The RPE also synthesize the structural proteins of Bruch's membrane that in turn constitutes the outer blood-retinal barrier. In early AMD, an accumulation of undigested intracellular debris occurs in the RPE and the sub-RPE space that progressively decreases RPE function. In advanced AMD, the RPE dysfunction will lead to an ingrowth of choroidal vessels through breaks in Bruch's membrane (ie. neovascular AMD) and/or geographic atrophy.

In geographic atrophy (GA), the degeneration primarily affects the RPE and photoreceptors and restoration by cell transplantation seems logical. Several different methods for obtaining RPE cells through differentiation of human embryonic stem cells (hESC) have been published, many of them successful even though requiring long times. One problem in all of the published differentiation programmes is that they either contain animal-derived or non-defined components (e.g. feeder cells, human serum), making them more difficult for clinical use.

In the present disclosure, RPE cells can be derived from stem cells using feeder-free, totally chemically defined, and xeno-free methods. The term "chemically defined" means that all of the components in the medium are known chemical substances which are not isolated from any biological tissues. The term "xeno-free" means that no substances of animal origin are used in the methods. Human embryonic stem cells can be cultured on a laminin substrate, which may contain a cadherin, and differentiated into RPE cells in completely chemically defined conditions without any substances of animal origin (i.e. clinical grade RPE cells).

Initially, the stem cells are cultured using a first cell culture medium that contains a growth factor such as basic fibroblast growth factor, i.e. bFGF or FGF2, such as a TeSR2 medium or the Nutristem medium (available from Stemgent). The amount of growth factor (i.e. FGF2) in the cell culture medium is 3.9 ng/ml or less. Once the cells are almost confluent, the cells are cultured in a second cell culture medium that does not contain growth factor (i.e. FGF2), such as the TeSR2 medium described above and suitably modified. This confluence may occur after one week. After the first time period of being exposed to the first cell culture medium (containing FGF2), the cells are removed from exposure to the first cell culture medium. This can be done by draining the first cell culture medium from the laminin substrate, or alternatively the stem cells can be replated to a second laminin substrate. The stem cells are then exposed to the second cell culture medium, i.e. cultured in the second cell culture medium. The second cell culture medium is periodically changed or refreshed, for example every week. After eight weeks, the stem cells have differentiated into RPE cells. The presence of FGF2 is typically needed to maintain the stem cells in a pluripotent state, so removing its presence causes differentiation of the stem cells into RPE cells. In this example, the stem cells were exposed to the first cell culture medium (containing growth factor) for one week, and then cultured in the second cell culture medium (no growth factor) for seven weeks. In principle, 100% of the stem cells can become clinical grade RPE cells which can then be used to treat patients with AMD by subretinal injection or other transplantation processes.

Example 5

Xeno-Free Feeder-Free Differentiation of Clinical Grade Human Retinal Pigment Epithelium on Human Recombinant Laminin 521 for Treatment of Macular Degeneration Human embryonic stem cells were used that had been established in xeno-free feeder-free conditions onto the surface of a laminin-521 substrate. Human embryonic stem cells (line HS980) were pipetted onto a LN-521 substrate. The stem cells were then cultured in one of two different chemically defined xeno-free culture media (TeSR2, Stem Cell Technologies, or Nutristem, Stemgent). Both media contain FGF2, and no additional growth factors were added to these media.

Figure 25:
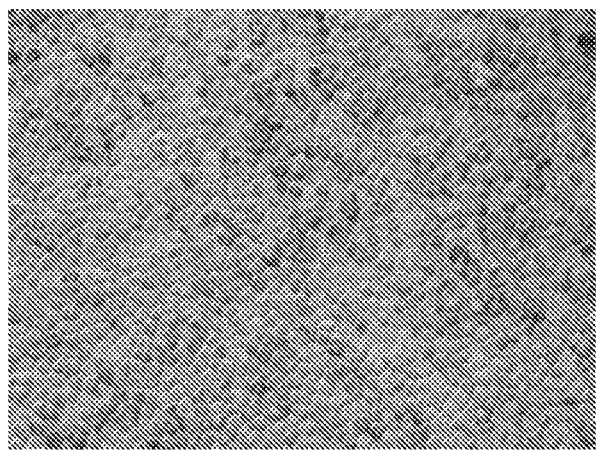
FIG. 25 is a picture of RPE cells at eight weeks, showing a cobblestone form.
Figure 26:
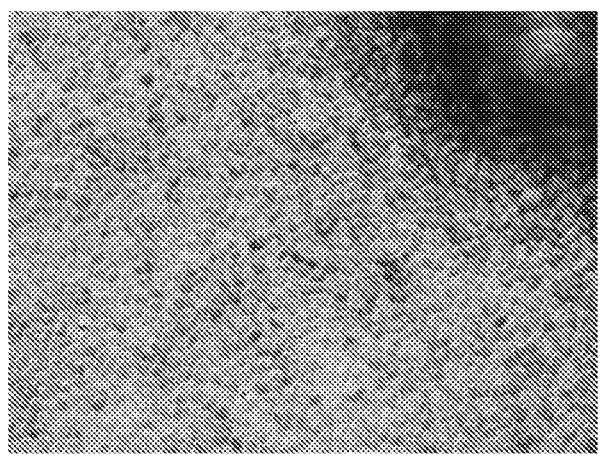
FIG. 26 is a second picture of RPE cells at eight weeks, showing a cobblestone form.

After one week, the stem cells were re-plated onto the surface of another LN-521 substrate. Next, the stem cells were exposed to a Nutristem XF medium which had been made without FGF2. The cells were maintained in those conditions, and eventually formed a monolayer with sometimes small pigmented aggregate. After six more weeks with weekly media changes of the Nutristem XF medium, the cells had differentiated to the cobblestone form typical of RPE, and there were more and more pigment in cells. After eight weeks, they have become typical RPE cells. FIG. 25 and FIG. 26 are photomicrographs showing the cobblestone form of RPE cells after eight weeks.

The RPE cells are chemically defined, and animal substance free without added chemicals or growth factors. The RPE cells grow as a monolayer instead of miscellaneous clumps or embryoid bodies that are not evenly differentiated populations. The clinical grade RPE cells can then be used to treat patients with AMD, such as by subretinal injection or other like treatments or processes.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

---

The invention claimed is:

1. A method of obtaining retinal pigment epithelium (RPE) cells, comprising:
   culturing one or more stem cells on a substrate comprising a laminin, wherein the laminin is an intact protein or a protein fragment, and wherein the laminin is laminin-521 or laminin-511;
   exposing the stem cells to a first cell culture medium that contains a growth factor, wherein the growth factor is basic fibroblast growth factor (FGF2), the first cell culture medium being completely chemically defined and xeno-free, wherein the growth factor maintains the stem cells in a pluripotent state;
   after a first time period, removing the first cell culture medium and exposing the stem cells to a second cell culture medium that does not contain the growth factor, the second cell culture medium being completely chemically defined and xeno-free, wherein removal of the growth factor causes differentiation of the stem cells to RPE cells.

2. The method of claim 1, wherein the laminin is an effective recombinant laminin.

3. The method of claim 1, wherein the substrate further comprises a cadherin.

4. The method of claim 3, wherein the cadherin is e-cadherin.

5. The method of claim 3, wherein the weight ratio of the laminin to the cadherin is from about 5:1 to about 15:1.

6. The method of claim 3, wherein the laminin is laminin-521 and the cadherin is e-cadherin.

7. The method of claim 6, wherein the weight ratio of laminin-521 to e-cadherin is from about 5:1 to about 15:1.

8. The method of claim 1, wherein the first cell culture medium contains the growth factor in an amount of greater than zero to 3.9 ng/ml.

9. The method of claim 1, wherein the growth factor not contained in the second cell culture is FGF2.

10. The method of claim 1, wherein the substrate, the first cell culture medium, and the second cell culture medium do not contain any substances of animal origin.

11. The method of claim 1, wherein the first time period is about one week.

12. The method of claim 1, wherein the periodic replacing of the second cell culture medium occurs every week, and the RPE cells are obtained after a total of about eight weeks.

13. The method of claim 1, wherein the stem cells are exposed to the first cell culture medium for about one week, and are exposed to the second cell culture medium for about seven weeks, to obtain the RPE cells.

14. A method of obtaining retinal pigment epithelium (RPE) cells, comprising:
   culturing one or more stem cells on a substrate comprising a laminin, wherein the laminin is an intact protein or a protein fragment, and wherein the laminin is laminin-521 or laminin-511;
   exposing the stem cells to a first cell culture medium that contains a growth factor, wherein the growth factor is basic fibroblast growth factor (FGF2), the first cell culture medium being completely chemically defined and xeno-free;

after a first time period, removing the first cell culture medium and exposing the stem cells to a second cell culture medium that does not contain the growth factor, the second cell culture medium being completely chemically defined and xeno-free; and periodically replacing the second cell culture medium, wherein differentiation of the stem cells into the RPE cells occurs on the substrate comprising the laminin.

15. The method of claim 1, wherein the FGF2 is in the amount of at least about 3.9 ng/mL.

16. The method of claim 1, wherein the laminin is human laminin-511 or laminin-521.

17. The method of claim 1, wherein the RPE cells produced are suitable for use in treating a patient with macular degeneration.

* * * * *